(12) United States Patent
Rothbard et al.

(10) Patent No.: US 6,759,387 B2
(45) Date of Patent: *Jul. 6, 2004

(54) COMPOSITIONS AND METHODS FOR ENHANCING DRUG DELIVERY ACROSS AND INTO EPITHELIAL TISSUES

(75) Inventors: Jonathan B. Rothbard, Cupertino, CA (US); Paul A. Wender, Menlo Park, CA (US); P. Leo McGrane, Mountain View, CA (US); Lalitha V. S. Sista, Sunnyvale, CA (US); Thorsten A. Kirschberg, Mountain View, CA (US)

(73) Assignee: Cellgate, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/209,421

(22) Filed: Jul. 30, 2002

(65) Prior Publication Data

US 2003/0083256 A1 May 1, 2003

Related U.S. Application Data

(63) Continuation of application No. 09/648,400, filed on Aug. 24, 2000, now Pat. No. 6,593,292.
(60) Provisional application No. 60/150,510, filed on Aug. 24, 1999.

(51) Int. Cl.[7] .................. A61K 31/436; A61K 31/496; A61K 38/04; A61K 38/16
(52) U.S. Cl. ................. 514/2; 514/12; 514/13; 514/14; 514/15; 514/16; 514/17; 514/254.07; 514/291; 514/383; 514/399; 540/461; 544/366; 548/266.6; 548/342.5
(58) Field of Search ............... 424/1.69, 9.322, 424/9.323, 9.34, 9.341, 9.1, 9.411, 433, 434, 435, 436, 437, 428, 449; 514/2, 3, 11, 12, 13, 14, 15, 16, 17, 634, 635, 636, 159, 169, 291, 456, 252.13, 252.14, 252.19, 254.07, 166, 263, 383, 423, 457, 458, 25, 152, 198, 199, 200, 262, 269, 399; 520/300, 302, 303, 315, 317, 321, 324, 325, 326, 327, 328, 329, 330; 544/366; 564/225, 230, 236, 243; 540/461; 548/266.5, 342.5

(56) References Cited

U.S. PATENT DOCUMENTS 4,046,722 A 9/1977 Rowland .................... 530/362

(List continued on next page.)

FOREIGN PATENT DOCUMENTS

CA 2094658 10/1993

(List continued on next page.)

OTHER PUBLICATIONS

Arbuck, et al. "Taxol: Clinical Results and Current Issues in Development"; Chapter 14 in TAXOL®: *Science and Applications*, M. Suffness ed., CRC Press (New York), p. 379–415 (1995).

(List continued on next page.)

*Primary Examiner*—Jeffrey E. Russel
(74) *Attorney, Agent, or Firm*—Townsend and Townsend and Crew LLP

(57) ABSTRACT

This invention provides compositions and methods for enhancing delivery of drugs and other agents across epithelial tissues, including the skin, gastrointestinal tract, pulmonary epithelium, and the like. The compositions and methods are also useful for delivery across endothelial tissues, including the blood brain barrier. The compositions and methods employ a delivery enhancing transporter that has sufficient guanidino or amidino sidechain moieties to enhance delivery of a compound conjugated to the reagent across one or more layers of the tissue, compared to the non-conjugated compound. The delivery-enhancing polymers include, for example, poly-arginine molecules that are preferably between about 6 and 25 residues in length (SEQ ID NO:50).

31 Claims, 23 Drawing Sheets

U.S. PATENT DOCUMENTS

| | | | | |
|---|---|---|---|---|
| 4,532,207 | A | 7/1985 | Brewer et al. | 435/68 |
| 4,631,190 | A | 12/1986 | Shen et al. | 424/85 |
| 4,701,521 | A | 10/1987 | Ryser et al. | 530/322 |
| 4,847,240 | A | 7/1989 | Ryser et al. | 514/12 |
| 4,880,911 | A | 11/1989 | Brewer et al. | 530/351 |
| 5,028,707 | A | 7/1991 | Nichols et al. | 546/156 |
| 5,162,505 | A | 11/1992 | Dean et al. | 530/391.5 |
| 5,354,844 | A | 10/1994 | Beug et al. | 530/345 |
| 5,362,831 | A | 11/1994 | Mongelli et al. | 526/304 |
| 5,633,230 | A | 5/1997 | Twist et al. | 514/15 |
| 5,646,120 | A | 7/1997 | Sumner-Smith et al. | 514/14 |
| 5,674,849 | A | 10/1997 | Twist et al. | 514/15 |
| 5,716,614 | A | 2/1998 | Katz et al. | 424/94.3 |
| 5,783,178 | A | 7/1998 | Kabanov et al. | 424/78.31 |
| 5,789,531 | A | 8/1998 | Sumner-Smith et al. | 530/328 |
| 5,795,909 | A | 8/1998 | Shashoua | 514/449 |
| 5,804,604 | A | 9/1998 | Frankel et al. | 530/324 |
| 5,831,001 | A | 11/1998 | Twist et al. | 530/328 |
| 5,977,163 | A | 11/1999 | Li et al. | 514/449 |
| 6,077,835 | A | 6/2000 | Hanson et al. | 517/44 |
| 6,306,993 | B1 * | 10/2001 | Rothbard et al. | 526/304 |
| 6,593,292 | B1 * | 7/2003 | Rothbard et al. | 514/2 |

FOREIGN PATENT DOCUMENTS

| | | |
|---|---|---|
| DE | 744 988 | 2/1956 |
| EP | 0009498 | 4/1980 |
| EP | 0 599 303 | 6/1994 |
| JP | 10 095738 | 4/1998 |
| WO | WO 79/00515 | 8/1979 |
| WO | WO 91/09958 | 7/1991 |
| WO | WO 92/07871 | 5/1992 |
| WO | WO 93/04701 | 3/1993 |
| WO | WO 93/21941 | 11/1993 |
| WO | WO 94/04686 | 3/1994 |
| WO | WO 94/14464 | 7/1994 |
| WO | WO 95/11038 | 4/1995 |
| WO | WO 96/21036 | 7/1996 |
| WO | WO 97/33552 | 9/1997 |
| WO | WO 97/40854 | 11/1997 |
| WO | WO 98/52614 | 11/1998 |
| WO | WO 01/13957 | 3/2001 |

OTHER PUBLICATIONS

Balicki, et al. "Histone H2A Significantly Enhances In Vitro DNA Transfection"; *Molecular Medicine* vol. 3, No. 11 p. 782–787 (1997).

Boussif, et al. "A versatile vector for gene and oligonucleotide transfer into cells in culture and in vivo: Polyethylenimine"; *Proc. Natl. Acad. Sci. USA* vol. 92, p. 7297–7301 (Aug. 1995).

Burton, et al. "Basic polyelectrolytes and protein transport across the new–born pig intestine"; *Physiological Society* p. 27P–28P (Dec. 1970), vol. 211, No. 2.

Brugidou, et al. "The Retro–Inverso Form of a Homeobox–Derived Short Peptide is Rapidly Internalised by Cultured Neurones: A New Basis For An Efficient Intracellular Delivery System"; *Biochemical and Biophysical Research Communications* vol. 214, No. 2 p. 685–693 (Sep. 1995).

Buschle, et al. "Transloading of tumor antigen–derived peptides into antigen–presenting cells"; *PNAS* vol. 94, p. 3256–3261 (Apr. 1997).

Chen, et al. "Galactosylated Histone–Mediated Gene Transfer and Expression"; *Human Gene Therapy* vol. 5, p. 429–435 (1994).

Cooke, et al. "Nitric Oxide Synthase: Role in the Genesis of Vascular Disease"; *Annu. Rev. Med.* vol. 48, p. 489–509 (1997).

Dattilo, et al. "Inducible Nitric Oxide Synthase Expression in Human Vein Grafts"; *Am J Surg.* vol. 174, p. 177–180 (1997).

de Bont, et al. "Synthesis and Biological Activity of β–Glucuronyl Carbamate–Based Prodrugs of Paclitaxel as Potential Candidates for ADEPT"; *Bioorganic & Medicinal Chemistry* vol. 5, No. 2 p. 405–414 (1997).

Derossi, et al. "The Third Helix of the Antennapedia Homeodomain Translocates through Biological Membranes"; *The Journal of Biological Chemistry* vol. 269, No. 14 p. 10444–10450 (1994).

Elferink, "Changes of Plasma Membrane Permeability in Neutrophils Treated With Polycations"; *Inflammation* vol. 15, No. 2 p. 103–115 (Apr. 1991).

Emi, et al. "Gene Transfer Mediated by Polyarginine Requires a Formation of Big Carrier–Complex of DNA Aggregate"; *Biochemical and Biophysical Research Communications* vol. 231, p. 421–424 (1997).

Fawell, et al. "Tat–mediated delivery of heterologous proteins into cells"; *Proc. Natl. Acad. Sci. USA* vol. 91, p. 664–668 (Jan. 1994).

Fletcher, et al. "Partially Modified Retro–Inverso Peptides: Development, Synthesis, and Conformational Behavior"; *Chem. Rev.* vol. 96 p. 763–795 (1998).

Garg, et al. "Nitric Oxide–generating Vasodilators and 8–Bromo–Cyclic Guanosine Monophosphate Inhibit Mitogenesis and Proliferation of Cultured Rat Vascular Smooth Muscle Cells"; *J. Clin. Invest.* vol. 83, p. 1774–1777 (May 1989).

Georg, et al. "The Medicinal Chemistry of Taxol"; Chapter 13 in TAXOL®: *Science and Applications*, M. Suffness ed., CRC Press (New York), p. 317–375 (1995).

Golik, et al. "Synthesis and Antitumor Evaluation of Paclitaxel Phosphonooxymethyl Ethers: A Novel Class of Water Soluble Paclitaaxel Pro–Drugs" *Bioorganic & Medicinal Chemistry Letters* vol. 6, No. 15 p. 1837–1842 (1996).

Greenwald, et al. "Drug Delivery Systems: Water Soluble Taxol 2'–Poly(ethylene glycol) Ester Prodrugs–Design and in Vivo Effectiveness"; *J. Med. Chem.* 39(2):424–431 (Jan. 1996).

Kessler "Peptoids—A New Approach to the Development of Pharmaceuticals"; *Angew Chem. Int. Ed. Engl.* vol. 32, No. 4 p. 543–544 (1993).

Kingston "Natural Toxoids: Structure and Chemistry"; Chapter 12 in TAXOL®: *Science & Applications*, M. Suffness ed, CRC Press (New York), p. 287–315 (1995).

Lam, et al. "The "One–Bead–One–Compound" Combinatorial Library Method"; *Chem. Rev.* vol. 97, p. 411–448 (1997).

Lloyd–Jones, M.D., et al. "The Vascular Biology of Nitric Oxide and Its Role in Atherogenesis"; *Annu. Rev. Med.* vol. 47, p. 365–375 (1996).

Mauersberger, et al. "Untersuchungen zur Zytotoxizität von Poly–L–Arginin, Poly–L–Lysin and DEAE–Dextran bei L–Zellen und Mäuseembryofibroblasten"; *Exp. Path* vol. 18 p. 268–274 (1977).

Murphy, et al. "A combinatorial approach to the discovery of efficient cationic peptoid reagents for gene delivery"; *Proc. Natl. Acad. Sci. USA* vol. 95, p. 1517–1522 (Feb. 1998).

Natsume, et al. "Screening of Absorption Enhancers for Nasal Peptide and Protein Delivery"; *Proceed. Intern. Symp. Control. Rel. Bioact. Mater.* vol. 23, p. 481–482 (Jul. 1996).

Nicolaou, et al., "Design, synthesis and biological activity of protaxols"; *Nature* vol. 364, p. 464–466 (Jul. 1993).

Rodrigues, et al. "Synthesis and β–lactamase–mediated activation of a cephalosporin–taxol prodrug" *Chemistry and Biology* vol. 2, p. 223–227 (Apr. 1995).

Rose, "Preclinical Antitumor Activity of Taxanes"; Chapter 8 in TAXOL®; *Science & Applications*, M. Suffness ed., CRC Press (New York), p. 209–235 (1995).

Simon, et al. "Peptoids: A modular approach to drug discovery"; *Proc. Natl. Acad. Sci. USA* vol. 89 p. 9367–9371 (Oct. 1992).

Straubinger "Biopharmaceutics of Paxlitaxel (Taxol): Formulation, Activity, and Pharmacokinetics"; Chapter 9 in TAXOL® *Science and Applications*, M. Suffness ed., CRC Press (New York), p. 237–258 (1995).

Sumner–Smith, et al. "123: 79357m Antiherpetic activities of N–α–acetyl–nona–D–=arginine amide acetate"; *6001 Chemical Abstracts* vol. 123, No. 7 p. 606 (1995).

Thompson, et al; "Synthesis and Applications of Small Molecule Libraries"; *Chem. Rev.* 96:555–600 (1996).

Tsao, et al. "Nitric Oxide Regulates Monocyte Chemotactic Protein–1"; *Circulation* 96:, 934–940 (1997).

Uchida, et al. "Polycations Decrease the Transepithelial Resistance of Cultured Tracheal Epithelial Cells"; *Chest* vol. 101, No. 3, p. 33S (Mar. 1992).

Ueda, et al. "Synthesis and Antitumor Evaluation of 2'–Oxycarbonylpaclitaxels (Paclitaxel–2'–Carbonates)"; *Bioorganic & Medicinal Chemistry Letters* vol. 4 No. 15 p. 1861–1864 (Aug. 1994).

Ueda, et al. "Novel Water Soluble Phosphate Prodrugs of Taxol® Possessing In Vivo Antitumor Activity"; 3(8):1761–1766 (May 1993).

Vyas, et al. "Synthesis and Antitumor Evaluation of Water Soluble Taxol Phosphates"; *Bioorganic & Medicinal Chemistry Letters* vol. 3, No. 6 p. 1357–1360 (1993).

Vyas, et al. "Phosphatase–Activated Prodrugs of Paclitaxel";Chapter 9 in *Taxane Anticancer Agents* American Chemical Society p. 124 (1995).

Wolf, et al. "Dietary L–Arginine Supplementation Normalizes Platelet Aggregation in Hypercholesterolemic Humans", *JACC* vol. 29, No. 3 p. 479–485 (Mar. 1997).

Zuckermann, et al. "Efficient Method for the Preparation of Peptoids [Oligo(N–substituted glycines)] by Submonomer Solid–Phase Synthesis"; *Chemtracts–Macromolecular Chemistry* vol. 4 p. 80–83 (1993).

Aoyagi, et al. "Polymerization of Benzalkonium Chloride–Type Monomer and Application to Percutaneous Drug Absorption Enhancer"; *Journal of Controlled Release*, vol 13, No. 1, pp. 63–71 (Jul. 1990).

Babiuk, et al., "Cutaneous vaccination: the skin as an immunologically active tissue and the challenge of antigen delivery"; *Journal of Controlled Release* vol. 66 p. 199–214 (2000).

Colin, et al. "Liposomes enhance delivery and expression of an RGD–oligolysine gene transfer vector in human tracheal cells"; *Gene Therapy* vol. 5 pp. 1488–1498 (1998).

Coyle, e tal. "Role of Cationic Proteins in the Airway Hyperresponsiveness Due to Airway Inflammation"; *Am. Respir. Crit. Care Med.* vol. 150 pp. 563–571 (1994).

Gama, et al. "$Ca^{2+}$–sensing receptors in intestinal epithelium"; *American Journal of Physiology* vol. 273, No. 4, Part 1 pp. C1168–1175 (Oct. 1997).

Hosoya, et al. "Effect of Several Hydrophilic Polymers on the Permeation of Morphine and Salicyclic Acid through Excised Hairless Rat Skin"; Chem. Pharm. Bull. 46(5) 882–885 (1998).

Hulsmann, "Permeability of Human Isolated Airways Increases after Hydrogen Peroxide and Poly–L–arginine"; *Am. J. Respir. Crit. Care Med.* vol. 153 pp. 841–846 (1996).

Koji Kobayashi, "Composition for Transmucosally Absorbable Preparation"; Patent Abstracts of Japan, Publication No. 10095738, Publication Date Apr. 4, 1998.

Perr, et al. "Protamine Selectively Inhibits Collagen Synthesis by Human Intestinal Smooth Muscle Cells and Other Mesenchymal Cells"; *Journal of Cellular Physiology* 140:463–470 (1989).

Peterson, et al. "Polyamino Acid Enhancement of Bacterial Phagocytosis by Human Polymorphonuclear Leukocytes and Peritoneal Macrophages"; *Infection and Immunity* vol. 43, No. 2, pp. 561–566 (Feb. 1984).

Santana, et al., "Inflammatory responses induced by poly–L–arginine in rat lungs in vivo"; *Agents Actions* vol. 39, No. 3–4 pp. 104–110 (1993).

Tzan, et al. "Mammalian urinary bladder permeability is altered by cationic proteins modulation by divalent cations"; *American Journal of Physiology* vol. 267, No. 4, Part 1, pp. C1013–C1026 (1994).

Tzan, et al., "Modification of Epithelial Permeability by Cationic Polypeptides"; *American Journal of Physiology* vol. 265, No. 6, Part 1, pp. C1637–C1647 (1993).

Uchida, et. al., Cationic Proteins Increase the Permeability of Cultured Rabbit Trachael Epithelial Cells: Modification by Heparin and Extracellular Calcium: *Experimental Lung Research* vol. 22, No. 1, pp. 85–99 (1996).

Wei, et al. "synthesis of Oligoarginine–Oligonucleotide Conjugates and Oligoarginine–Bridge Oligonucleotide Pairs"; *Bioconjugate Chem.* vol. 5, pp. 468–474 (Sep./Oct. 1994).

* cited by examiner n = 5, 7, 9, 0 (control)

I

II

III

IV

A.

B.

n = 5 and 7 n = 1, 2
R = H, Ac

Synthetic Schemes for FK 506 Conjugates

Ref. Willner et al; Bioconjugate Chemistry, 1993, 4, 521-527

Synthetic Schemes for FK 506 Conjugates (contd.)

COMPOSITIONS AND METHODS FOR ENHANCING DRUG DELIVERY ACROSS AND INTO EPITHELIAL TISSUES

CROSS-REFERENCE TO RELATED APPLICATIONS

This application is a continuation of U.S. patent application Ser. No. 09/648,400, filed Aug. 24, 2000 now U.S. Pat. No. 6,593,292 which application claims priority to U.S. Provisional Application No. 60/150,510, filed Aug. 24, 1999, each of which are incorporated by reference in their entirety for all purposes.

BACKGROUND OF THE INVENTION

1. Field of the Invention

This invention pertains to the field of compositions and methods that enhance the delivery of drugs and other compounds across the dermal and epithelial membranes, including, for example, skin, the gastrointestinal epithelium and the bronchial epithelium.

2. Background

Transdermal or transmucosal drug delivery is an attractive route of drug delivery for several reasons. Gastrointestinal drug degradation and the hepatic first-pass effect are avoided. In addition, transdermal and transmucosal drug delivery is well-suited to controlled, sustained delivery (see, e.g., Elias, In *Percutaneous Absorption: Mechanisms-Methodology-Drug Delivery*, Bronaugh & Maibach, Eds., pp 1–12, Marcel Dekker, New York, 1989.). For many applications, traditional methods of administering drugs are not optimal because of the very large initial concentration of the drug. Transdermal delivery could allow a more uniform, slower rate of delivery of a drug. Moreover, patient compliance is encouraged because such delivery methods are easy to use, comfortable, convenient and non-invasive.

These advantages of transdernal and transmucosal delivery have not led to many clinical applications because of the low permeability of epithelial membranes, the skin in particular, to drugs. The difficulties in delivering drugs across the skin result from the barrier property of skin. Skin is a structurally complex thick membrane that represents the body's border to the external hostile environment. The skin is composed of the epidermis, the dermis, the hypodermis, and the adenexal structures (epidermal appendages). The epidermis, the outermost epithelial tissue of the skin, is itself composed of several layers—the stratum corneum, the stratum granulosum, the stratum spinosum, and the stratum basale.

Compounds that move from the environment into and through intact skin must first penetrate the stratum corneum, the outermost layer of skin, which is compact and highly keratinized. The stratum corneum is composed of several layers of keratin-filled skin cells that are tightly bound together by a "glue" composed of cholesterol and fatty acids. The thickness of the stratum corneum varies depending upon body location. It is the presence of stratum corneum that results in the impermeability of the skin to pharmaceutical agents. The stratum corneum is formed naturally by cells migrating from the basal layer toward the skin surface where they are eventually sloughed off. As the cells progress toward the surface, they become progressively more dehydrated and keratinized. The penetration across the stratum corneum layer is generally the rate-limiting step of drug permeation across skin. See, e.g., Flynn, G. L., In *Percutaneous Absorption: Mechanisms-Methodology-Drug Delivery*, supra. at pages 27–53.

After penetration through the stratum corneum layer, systemically acting drug molecules then must pass into and through the epidermis, the dermis, and finally through the capillary walls of the bloodstream. The epidermis, which lies under the stratum corneum, is composed of three layers. The outermost of these layers is the stratum granulosum, which lies adjacent to the stratum corneum, is composed of cells that are differentiated from basal cells and keratinocytes, which make up the underlying layers having acquired additional keratin and a more flattened shape. The cells of this layer of the epidermis, which contain granules that are composed largely of the protein filaggrin. This protein is believed to bind to the keratin filaments to form the keratin complex. The cells also synthesize lipids that function as a "cement" to hold the cells together. The epidermis, in particular the stratum granulosum, contains enzymes such as aminopeptidases.

The next-outermost layer of the epidermis is the stratum spinosum, the principal cells of which are keratinocytes, which are derived from basal cells that comprise the basal cell layer. Langerhans cells, which are also found in the stratum spinosum, are antigen-presenting cells and thus are involved in the mounting of an immune response against antigens that pass into the skin. The cells of this layer are generally involved in contact sensitivity dermatitis.

The innermost epidermal layer is the stratum basale, or basal cell layer, which consists of one cell layer of cuboidal cells that are attached by hemi-desmosomes to a thin basement membrane which separates the basal cell layer from the underlying dermis. The cells of the basal layer are relatively undifferentiated, proliferating cells that serve as a progenitor of the outer layers of the epidermis. The basal cell layer includes, in addition to the basal cells, melanocytes.

The dermis is found under the epidermis, which is separated from the dermis by a basement membrane that consists of interlocking rete ridges and dermal papillae. The dermis itself is composed of two layers, the papillary dermis and the reticular dermis. The dermis consists of fibroblasts, histiocytes, endothelial cells, perivascular macrophages and dendritic cells, mast cells, smooth muscle cells, and cells of peripheral nerves and their end-organ receptors. The dermis also includes fibrous materials such as collagen and reticulin, as well as a ground substance (principally glycosaminoglycans, including hyaluronic acid, chondroitin sulfate, and dermatan sulfate).

Several methods have been proposed to enhance transdermal transport of drugs. For example, chemical enhancers (Burnette, R. R. In *Developmental Issues and Research Initiatives*; Hadgraft J., Ed., Marcel Dekker: 1989; pp. 247–288), iontophoresis, and others have been used. However, in spite of the more than thirty years of research that has gone into delivery of drugs across the skin in particular, fewer than a dozen drugs are now available for transdermal administration in, for example, skin patches.

Transport of drugs and other molecules across the blood-brain barrier is also problematic. The brain capillaries that make up the blood-brain barrier are composed of endothelial cells that form tight junctions between themselves (Goldstein et al., *Scientific American* 255:74–83 (1986); Pardridge, W. M., *Endocrin. Rev.* 7: 314–330 (1986)). The endothelial cells and the tight intercellular junctions that join the cells form a barrier against the passive movement of many molecules from the blood to the brain. The endothelial cells of the blood-brain barrier have few pinocytotic vesicles, which in other tissues can allow somewhat unselective transport across the capillary wall. Nor is the blood-brain barrier interrupted by continuous gaps or channels that run through the cells, thus allowing for unrestrained passage of drugs and other molecules.

Thus, a need exists for improved reagents and methods for enhancing delivery of compounds, including drugs, across epithelial tissues and endothelial tissues such as the skin and the blood-brain barrier. The present invention fulfills this and other needs.

SUMMARY OF THE INVENTION

The present invention provides methods for enhancing delivery of a compound into and across one or more layers of an animal epithelial or endothelial tissue. The methods involve contacting tissue with a conjugate that includes the compound and a delivery-enhancing transporter. The delivery-enhancing transporters, which are also provided by the invention, have sufficient guanidino or amidino moieties to increase delivery of the conjugate into and across one or more intact epithelial or endothelial tissue layers compared to delivery of the compound in the absence of the delivery-enhancing transporter. Typically, the delivery-enhancing transporters have from 6 to 25 guanidino or amidino moieties, and more preferably between 7 and 15 guanidino moieties.

The delivery-enhancing transporters and methods of the invention are useful for delivering drugs, diagnostic agents, and other compounds of interest across epithelial tissues such as the skin and mucous membranes. Delivery across the blood-brain barrier is also enhanced by the conjugates and methods of the invention. The methods and compositions of the invention can be used not only to deliver the compounds to the particular site of administration, but also provide systemic delivery.

In some embodiments, the delivery-enhancing transporter comprises 7–15 arginine residues (SEQ ID NO:49) or analogs of arginine. The delivery-enhancing transporter can have at least one arginine that is a D-arginine and in some embodiments, all arginines are D-arginine. The delivery enhancing transporter can consist essentially of 5 to 50 amino acids, at least 50 percent of which are arginine. In some embodiments, at least 70% of the amino acids are arginines or arginine analogs. In some embodiments, the delivery-enhancing transporter comprises at least 5 contiguous arginines (SEQ ID NO:1) or arginine analogs.

The compound to be delivered can be connected to the delivery enhancing transporter by a linker. In some embodiments, the linker is a releasable linker which releases the compound, in biologically active form, from the delivery-enhancing transporter after the compound has passed into and through one or more layers of the epithelial and/or endothelial tissue. In some embodiments, the compound is released from the linker by solvent-mediated cleavage. The conjugate is, in some embodiments, substantially stable at acidic pH but the compound is substantially released from the delivery-enhancing transporter at physiological pH. In some embodiments, the half-life of the conjugate is between 5 minutes and 24 hours upon contact with the skin or other epithelial or endothelial tissue. For example, the half-life can be between 30 minutes and 2 hours upon contact with the skin or other epithelial or endothelial tissue.

Examples of conjugate structures of the invention include those having structures such as 3, 4, or 5, as follows:

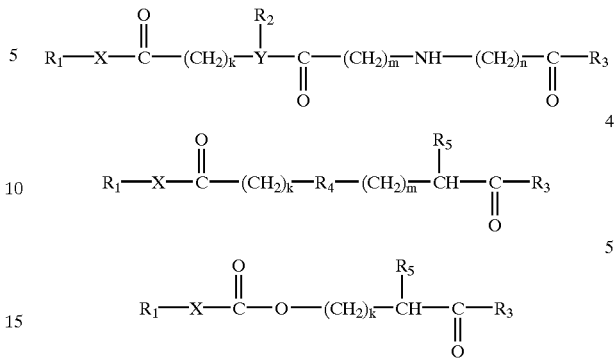

where $R_1$—X comprises the compound; X is a functional group on the compound to which the linker is attached; Y is N or C; $R_2$ is hydrogen, alkyl, aryl, acyl, or allyl; $R_3$ comprises the delivery-enhancing transporter; $R_4$ is substituted or unsubstituted S, O, N or C; $R_5$ is OH, SH or $NHR_6$; $R_6$ is hydrogen, alkyl, aryl, acyl or allyl; k and m are each independently selected from 1 and 2; and n is 1 to 10. Preferably, X is selected from the group consisting of N, O, S, and $CR_7R_8$, wherein $R_7$ and $R_8$ are each independently selected from the group consisting of H and alkyl. In some embodiments, $R_4$ is S; $R_5$ is $NHR_6$; and $R_6$ is hydrogen, methyl, allyl, butyl or phenyl. In some embodiments, $R_2$ is benzyl; k, m, and n are each 1, and X is O. In some embodiments, the conjugate comprises structure 3 and $R_2$ is selected to obtain a conjugate half-life of between 5 minutes and 24 hours. In some embodiments, $R_2$ is selected to obtain a conjugate half-life of between 5 minutes and 24 hours. In some embodiments, the conjugate comprises structure 4; $R_4$ is S; $R_5$ is $NHR_6$; and $R_6$ is hydrogen, methyl, allyl, butyl or phenyl. In some embodiments, the conjugate comprises structure 4; $R_5$ is $NHR_6$; $R_6$ is hydrogen, methyl, allyl, butyl or phenyl; and k and m are each 1. One example of a conjugate is:

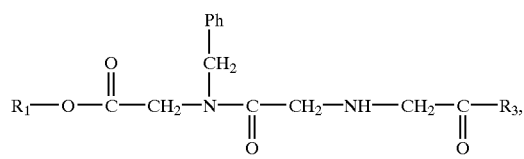

where Ph is phenyl.

The invention also provides conjugates in which the release of the linker from the biological agent involves a first, rate-limiting intramolecular reaction, followed by a faster intramolecular reaction that results in release of the linker. The rate-limiting reaction can, by appropriate choice of substituents of the linker, be made to be stable at a pH that is higher or lower than physiological pH. However, once the conjugate has passed into and across one or more layers of an epithelial or endothelial tissue, the linker will be cleaved from the agent. An example of a compound that has this type of linker is structure 6, as follows:

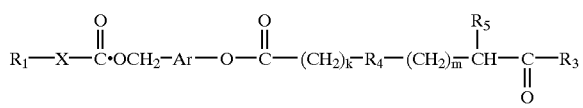

wherein R$_1$—X comprises the compound to be delivered across one or more layers of an epithelial and/or endothelial tissue; X is a functional group on the compound to which the linker is attached; Ar is an aryl group having the attached radicals arranged in an ortho or para configuration, which aryl group can be substituted or unsubstituted; R$_3$ comprises the delivery-enhancing transporter; R$_4$ is substituted or unsubstituted S, O, N or C; R$_5$ is OH, SH or NHR$_6$; R$_6$ is hydrogen, alkyl, aryl, acyl or allyl; and k and m are each independently selected from 1 and 2. In some embodiments, X is selected from the group consisting of N, O, S, and CR$_7$R$_8$, wherein R$_7$ and R$_8$ are each independently selected from the group consisting of H and alkyl. In some embodiments, R$_4$ is S; R$_5$ is NHR$_6$; and R$_6$ is hydrogen, methyl, allyl, butyl or phenyl. In some embodiments, the conjugate comprises:

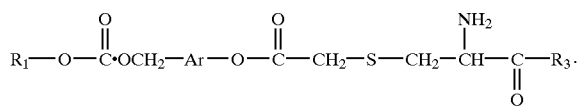

In preferred embodiments, the compositions of the invention comprise a linker susceptible to solvent-mediated cleavage. For example, a preferred linker is substantially stable at acidic pH but is substantially cleaved at physiological pH.

Additional embodiments of the invention provide transdermal drug formulations. These formulations include a therapeutically effective amount of a therapeutic agent, a delivery-enhancing transporter that includes sufficient guanidino or amidino sidechain moieties to increase delivery of the conjugate across one or more layers of an animal epithelial tissue compared to the trans-epithelial tissue delivery of the biologically active agent in non-conjugated form; and a vehicle suited to transdermal drug administration.

BRIEF DESCRIPTION OF THE FIGURES

FIG. 5A shows an example of a disulfide linkage. FIG. 5B shows a photocleavable linker which is cleaved upon exposure to electromagnetic radiation. FIG. 5C shows a modified lysyl residue used as a cleavable linker. FIG. 5D shows a conjugate in which the delivery-enhancing transporter T is linked to the 2'-oxygen of the anticancer agent, paclitaxel. The linking moiety includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. FIG. 5E a linkage of a delivery-enhancing transporter to a biologically active agent, e.g., paclitaxel, by an aminoalkyl carboxylic acid; a linker amino group is joined to a delivery-enhancing transporter by an amide linkage and to a paclitaxel moiety by an ester linkage. FIGS. 5F and G show chemical structures and conventional numbering of constituent backbone atoms for paclitaxel and "TAXOTERE™" (R'=H, R"=BOC). FIG. 5G shows the general chemical structure and ring atom numbering for taxoid compounds.

DETAILED DESCRIPTION

Definitions

Figure 1:
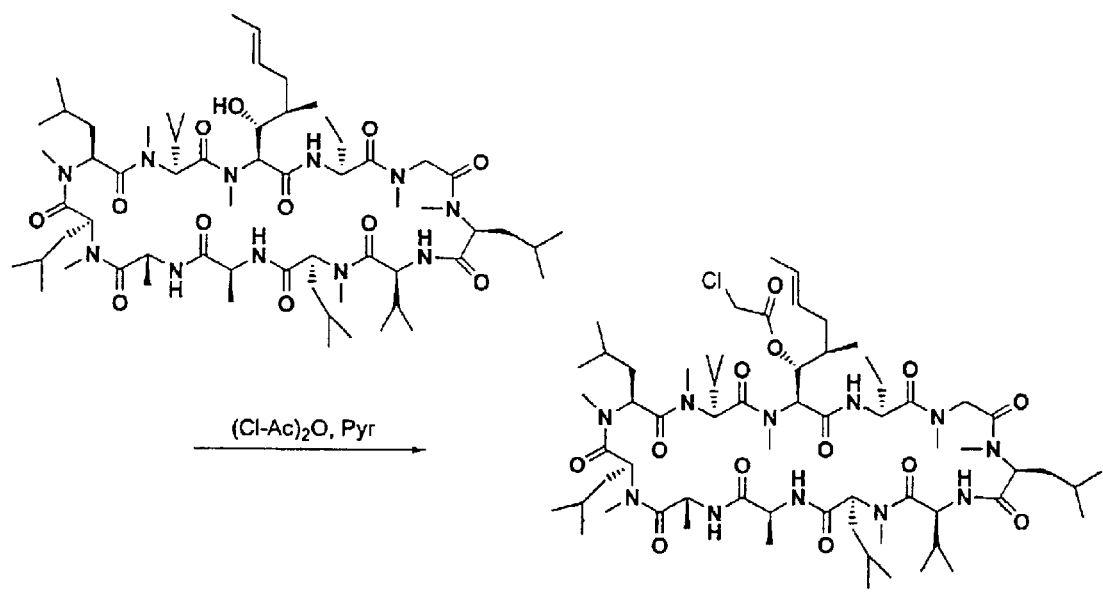
FIG. 1 shows a reaction scheme for the preparation of an α-chloroacetyl cyclosporin A derivative.

An "epithelial tissue" is the basic tissue that covers surface areas of the surface, spaces, and cavities of the body. Epithelial tissues are composed primarily of epithelial cells that are attached to one another and rest on an extracellular matrix (basement membrane) that is typically produced by the cells. Epithelial tissues include three general types based on cell shape: squamous, cuboidal, and columnar epithelium. Squamous epithelium, which lines lungs and blood vessels, is made up of flat cells. Cuboidal epithelium lines kidney tubules and is composed of cube shaped cells, while columnar epithelium cells line the digestive tract and have a columnar appearance. Epithelial tissues can also be classified based on the number of cell layers in the tissue. For example, a simple epithelial tissue is composed of a single layer of cells, each of which sits on the basement membrane. A "stratified" epithelial tissue is composed of several cells stacked upon one another; not all cells contact the basement membrane. A "pseudostratified" epithelial tissue has cells that, although all contact the basement membrane, appear to be stratified because the nuclei are at various levels.

The term "trans-epithelial" delivery or administration refers to the delivery or administration of agents by permeation through one or more layers of a body surface or tissue, such as intact skin or a mucous membrane, by topical administration. Thus, the term is intended to include both transdermal (e.g., percutaneous adsorption) and transmucosal administration. Delivery can be to a deeper layer of the tissue, for example, and/or delivery to the bloodstream.

"Delivery enhancement, "penetration enhancement" or "permeation enhancement" as used herein relates to an increase in amount and/or rate of delivery of a compound that is delivered into and across one or more layers of an epithelial or endothelial tissue. An enhancement of delivery can be observed by measuring the rate and/or amount of the compound that passes through one or more layers of animal or human skin or other tissue. Delivery enhancement also can involve an increase in the depth into the tissue to which the compound is delivered, and/or the extent of delivery to one or more cell types of the epithelial or other tissue (e.g., increased delivery to fibroblasts, immune cells, and endothelial cells of the skin or other tissue). Such measurements are readily obtained by, for example, using a diffusion cell apparatus as described in U.S. Pat. No. 5,891,462.

The amount or rate of delivery of an agent across and/or into skin or other epithelial or endothelial membrane is sometimes quantitated in terms of the amount of compound passing through a predetermined area of skin or other tissue, which is a defined area of intact unbroken living skin or mucosal tissue. That area will usually be in the range of about 5 $cm^2$ to about 100 $cm^2$, more usually in the range of about 10 $cm^2$ to about 100 $cm^2$, still more usually in the range of about 20 $cm^2$ to about 60 $cm^2$.

The terms "guanidyl," guanidinyl" and "guanidino" are used interchangeably to refer to a moiety having the formula —HN═C(NH$_2$)NH (unprotonated form). As an example, arginine contains a guanidyl (guanidino) moiety, and is also referred to as 2-amino-5-guanidinovaleric acid or α-amino-δ-guanidinovaleric acid. "Guanidium" refers to the positively charged conjugate acid form. The term "guanidino moiety" includes, for example, guanidine, guanidinium, guanidine derivatives such as (RNHC(NH)NHR'), monosubstituted guanidines, monoguanides, biguanides, biguanide derivatives such as (RNHC(NH)NHC(NH)NHR'), and the like. In addition, the term "guanidino moiety" encompasses any one or more of a guanide alone or a combination of different guanides.

"Amidinyl" and "amidino" refer to a moiety having the formula —C(=NH)(NH$_2$). "Amidinium" refers to the positively charged conjugate acid form.

The term "trans-barrier concentration" or "trans-tissue concentration" refers to the concentration of a compound present on the side of one or more layers of an epithelial or endothelial barrier tissue that is opposite or "trans" to the side of the tissue to which a particular composition has been added. For example, when a compound is applied to the skin, the amount of the compound measured subsequently across one or more layers of the skin is the trans-barrier concentration of the compound.

"Biologically active agent" or "biologically active substance" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

The term "macromolecule" as used herein refers to large molecules (MW greater than 1000 daltons) exemplified by, but not limited to, peptides, proteins, oligonucleotides and polynucleotides of biological or synthetic origin.

"Small organic molecule" refers to a carbon-containing agent having a molecular weight (MW) of less than or equal to 1000 daltons.

The terms "non-polypeptide agent" and "non-polypeptide therapeutic agent" refer to the portion of a conjugate that does not include the delivery-enhancing transporter, and that is a biologically active agent other than a polypeptide. An example of a non-polypeptide agent is an anti-sense oligonucleotide, which can be conjugated to a polyarginine peptide to form a conjugate for enhanced delivery into and across one or more layers of an epithelial or endothelial tissue.

A "subunit," as used herein, is a monomeric unit that are joined to form a larger polymeric compound. The set of amino acids are an example of subunits. Each amino acid shares a common backbone (—C—C—N—), and the different amino acids differ in their sidechains. The backbone is repeated in a polypeptide. A subunit represents the shortest repeating pattern of elements in a polymer backbone. For example, two amino acids of a peptide are not considered a peptide because two amino acids would not have the shortest repeating pattern of elements in the polymer backbone.

The term "polymer" refers to a linear chain of two or more identical or non-identical subunits joined by covalent bonds. A peptide is an example of a polymer; peptides can be composed of identical or non-identical amino acid subunits that are joined by peptide linkages (amide bonds).

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine). Homopolymer peptides are represented by a one-letter amino acid symbol-followed-by the number of consecutive occurrences of that amino acid in the peptide- (e.g., R7 represents a heptamer that consists of L-arginine residues; SEQ ID NO:3).

The term "protein" as used herein refers to a com-pound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

Description of the Preferred Embodiments

The present invention provides compositions and methods that enhance the transfer of compounds, including drugs and other biologically active compounds, into and across one or more layers of an animal epithelial or endothelial tissue. The methods involve contacting the tissue with a conjugate that includes the compound of interest linked to a delivery-enhancing transporter. The delivery enhancing transporters provided by the invention are molecules that include sufficient guanidino or amidino moieties to increase delivery of the conjugate into and across one or more intact epithelial and endothelial tissue layers. The methods and compositions are useful for trans-epithelial and trans-endothelial delivery of drugs and other biologically active molecules, and also for delivery of imaging and diagnostic molecules. The methods and compositions of the invention are particularly useful for delivery of compounds that require trans-epithelial or trans-endothelial transport to exhibit their biological effects, and that by themselves (without conjugation to a delivery-enhancing transporters or some other modification), are unable, or only poorly able, to cross such tissues and thus exhibit biological activity.

The delivery-enhancing transporters and methods of the invention provide significant advantages over previously available methods for obtaining trans-epithelial and trans-endothelial tissue delivery of compounds of interest. The transporters make possible the delivery of drugs and other agents across tissues that were previously impenetrable to the drug. For example, while delivery of drugs across skin was previously nearly impossible for all but a few compounds, the methods of the invention can deliver compounds not only into cells of a first layer of an epithelial tissue such as skin, but also across one or more layers of the skin. The blood brain barrier is also resistant to transport of drugs and other diagnostic and therapeutic reagents; the methods and transporters of the invention provide means to obtain such transport.

The delivery-enhancing transporters increase delivery of the conjugate into and across one or more intact epithelial or endothelial tissue layers compared to delivery of the compound in the absence of the delivery-enhancing transporter. The delivery-enhancing transporters can, in some embodiments, increase delivery of the conjugate significantly over that obtained using the tat protein of HIV-1 (Frankel et al. (1991) PCT Pub. No. WO 91/09958). Delivery is also increased significantly over the use of shorter fragments of the tat protein containing the tat basic region (residues 49–57) having the sequence RKKRRQRRR; SEQ ID NO:28) (Barsoum e at. (1994) WO 94/04686 and Fawell Ct at. (1994) *Proc. Nat'l. Acad. Sci.* USA 91: 664–668). Preferably, delivery obtained using the transporters of the invention is increased more than 2-fold, still more preferably six-fold, still more preferably ten-fold, and still more preferably twenty-fold, over that obtained with tat residues 49–57.

Similarly, the delivery-enhancing transporters of the invention can provide increased delivery compared to a 16 amino acid peptide-cholesterol conjugate derived from the Antennapedia homeodomain that is rapidly internalized by cultured neurons (Brugidou et al. (1995) *Biochem. Biophys. Res. Commun.* 214: 685–93). This region, residues 43–58 at minimum, has the amino acid sequence RQIKIWFQNR-RMKWKK (SEQ ID NO:29). The Herpes simplex protein VP22, like tat and the Antennapedia domain, was previously known to enhance transport into cells, but was not known to enhance transport into and across endothelial and epithelial membranes (Elliot and O'Hare (1997) *Cell* 88: 223–33; Dilber et al. (1999) *Gene Ther.* 6:12–21; Phelan et al. (1998) *Nature Biotechnol.* 16: 440–3). In presently preferred embodiments, the delivery-enhancing transporters provide significantly increased delivery compared to the Antennapedia homeodomain and to the VP22 protein.

Structure of Delivery-Enhancing Transporters

The delivery-enhancing transporters of the invention are molecules that have sufficient guanidino and/or amidino moieties to increase delivery of a compound to which the delivery-enhancing transporter is attached into and across one or more layers of an epithelial tissue (e.g., skin or mucous membrane) or an endothelial tissue (e.g., the blood-brain barrier). The delivery-enhancing transporters generally include a backbone structure to which is attached the guanidino and/or amidino sidechain moieties. In some embodiments, the backbone is a polymer that consists of subunits (e.g., repeating monomer units), at least some of which subunits contain a guanidino or amidino moiety.

A. Guanidino and/or Amidino Moieties

The delivery-enhancing transporters typically display at least 5 guanidino and/or amidino moieties, and more preferably 7 or more such moieties. Preferably, the delivery-enhancing transporters have 25 or fewer guanidino and/or amidino moieties, and often have 15 or fewer of such moieties. In some embodiments, the delivery-enhancing transporter consists essentially of 50 or fewer subunits, and can consist essentially of 25 or fewer, 20 or fewer, or 15 or fewer subunits. The delivery-enhancing transporter can be as short as 5 subunits, in which case all subunits include a guanidino or amidino sidechain moiety. The delivery-enhancing transporters can have, for example, at least 6 subunits, and in some embodiments have at least 7 or 10 subunits. Generally, at least 50% of the subunits contain a guanidino or amidino sidechain moiety. More preferably, at least 70% of the subunits, and sometimes at least 90% of the subunits in the delivery-enhancing transporter contain a guanidino or amidino sidechain moiety.

Some or all of the guanidino and/or amidino moieties in the delivery-enhancing transporters can be contiguous. For example, the delivery-enhancing transporters can include from 6 to 25 contiguous guanidino and/or amidino-containing subunits. Seven or more contiguous guanidino and/or amidino-containing subunits are present in some embodiments. In some embodiments, each subunit that contains a guanidino moiety is contiguous, as exemplified by a polymer containing at least six contiguous arginine residues.

The delivery-enhancing transporters are exemplified by peptides. Arginine residues or analogs of arginine can constitute the subunits that have a guanidino moiety. Such an arginine-containing peptide can be composed of either all D-, all L- or mixed D- and L-amino acids, and can include additional amino acids, amino acid analogs, or other molecules between the arginine residues. Optionally, the delivery-enhancing transporter can also include a non-arginine residue to which a compound to be delivered is attached, either directly or through a linker. The use of at least one D-arginine in the delivery-enhancing transporters can enhance biological stability of the transporter during transit of the conjugate to its biological target. In some cases the delivery-enhancing transporters are at least about 50% D-arginine residues, and for even greater stability transporters in which all of the subunits are D-arginine residues are used. If the delivery enhancing transporter molecule is a peptide, the transporter is not attached to an amino acid sequence to which the amino acids that make up the delivery enhancing transporter molecule are attached in a naturally occurring protein.

Preferably, the delivery-enhancing transporter is linear. In a preferred embodiment, an agent to be delivered into and across one or more layers of an epithelial tissue is attached to a terminal end of the delivery-enhancing transporter. In some embodiments, the agent is linked to a single transport polymer to form a conjugate. In other embodiments, the conjugate can include more than one delivery-enhancing transporter linked to an agent, or multiple agents linked to a single delivery-enhancing transporter.

More generally, it is preferred that each subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

The guanidino or amidino moieties extend away from the backbone by virtue of being linked to the backbone by a sidechain linker. The sidechain atoms are preferably provided as methylene carbon atoms, although one or more other atoms such as oxygen, sulfur or nitrogen can also be present. For example, a linker that attaches a guanidino moiety to a backbone can be shown as:

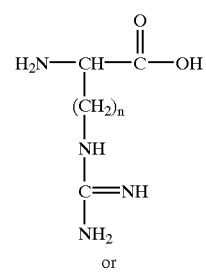

1 or

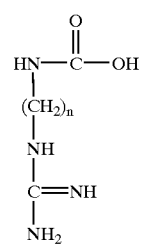

2

In these formulae, n is preferably at least 2, and is preferably between 2 and 7. In some embodiments, n is 3 (arginine for structure 1). In other embodiments, n is between 4 and 6; most preferably n is 5 or 6. Although the sidechain in the exemplified formulae is shown as being attached to a peptide backbone (i.e., a repeating amide to which the sidechain is attached to the carbon atom that is α to the carbonyl group, subunit 1) and a peptoid backbone (i.e., a repeating amide to which the sidechain is attached to the nitrogen atom that is β to the carbonyl group, subunit 2), other non-peptide backbones are also suitable, as discussed in more detail herein. Thus, similar sidechain linkers can be attached to nonpeptide backbones (e.g., peptoid backbones).

In some embodiments, the delivery-enhancing transporters are composed of linked subunits, at least some of which include a guanidino and/or amidino moiety. Examples of suitable subunits having guanidino and/or amidino moieties are described below.

Amino acids. In some embodiments, the delivery-enhancing transporters are composed of D or L amino acid residues. The amino acids can be naturally occurring or non-naturally occurring amino acids. Arginine (α-amino-δ-guanidinovaleric acid) and α-amino-ε-amidino-hexanoic acid (isosteric amidino analog) are examples of suitable guanidino- and amidino-containing amino acid subunits. The guanidinium group in arginine has a pKa of about 12.5. In some preferred embodiments the transporters are comprised of at least six contiguous arginine residues.

Other amino acids, such as α-amino-β-guanidino-propionic acid, α-amino-γ-guanidino-butyric acid, or α-amino-ε-guanidino-caproic acid (containing 2, 3 or 5 sidechain linker atoms, respectively, between the backbone chain and the central guanidinium carbon) can also be used.

D-amino acids can also be used in the delivery enhancing transporters. Compositions containing exclusively D-amino acids have the advantage of decreased enzymatic degradation. However, they can also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included within the conjugate to promote release of the agent in cells or organelles.

Other Subunits. Subunits other than amino acids can also be selected for use in forming transport polymers. Such subunits can include, but are not limited to, hydroxy amino acids, N-methyl-amino acids amino aldehydes, and the like, which result in polymers with reduced peptide bonds. Other subunit types can be used, depending on the nature of the selected backbone, as discussed in the next section.

B. Backbones

The guanidino and/or amidino moieties that are included in the delivery-enhancing transporters are generally attached to a linear backbone. The backbone can comprise a variety of atom types, including carbon, nitrogen, oxygen, sulfur and phosphorus, with the majority of the backbone chain atoms typically consisting of carbon. A plurality of sidechain moieties that include a terminal guanidino or amidino group are attached to the backbone. Although spacing between adjacent sidechain moieties is typically consistent, the delivery-enhancing transporters used in the invention can also include variable spacing between sidechain moieties along the backbone.

A more detailed backbone list includes N-substituted amide (CONR replaces CONH linkages), esters ($CO_2$), keto-methylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), trans-alkene (CR=CH), fluoroalkene (CF=CH), dimethylene ($CH_2CH_2$), thioether ($CH_2S$), hydroxyethylene ($CH(OH)CH_2$), methyleneoxy ($CH_2O$), tetrazole ($CN_4$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted amides), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

As mentioned above, in a peptoid backbone, the sidechain is attached to the backbone nitrogen atoms rather than the carbon atoms. (See e.g., Kessler (1993) *Angew. Chem. Int. Ed. Engl.* 32:543; Zuckerman et al. (1992) *Chemtracts-Macromol. Chem.* 4:80; and Simon et al. (1992) *Proc. Nat'l. Acad. Sci. USA* 89:9367.) An example of a suitable peptoid backbone is poly-(N-substituted)glycine (poly-NSG). Synthesis of peptoids is described in, for example, U.S. Pat. No. 5,877,278. As the term is used herein, transporters that have a peptoid backbone are considered "non-peptide" transporters, because the transporters are not composed of amino acids having naturally occurring sidechain locations. Non-peptoid backbones, including peptoid backbones, provide enhanced biological stability (for example, resistance to enzymatic degradation in vivo).

C. Synthesis of Delivery-enhancing Transporters

Delivery-enhancing transporters are constructed by any method known in the art. Exemplary peptide polymers can be produced synthetically, preferably using a peptide synthesizer (e.g., an Applied Biosystems Model 433) or can be synthesized recombinantly by methods well known in the art. Recombinant synthesis is generally used when the delivery enhancing transporter is a peptide which is fused to a polypeptide or protein of interest.

N-methyl and hydroxy-amino acids can be substituted for conventional amino acids in solid phase peptide synthesis. However, production of delivery-enhancing transporters with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al. (1998) *Chem. Rev.* 98:763, Simon et al. (1992) *Proc. Nat'l. Acad. Sci. USA* 89:9367, and references cited therein.

The delivery-enhancing transporters of the invention can be flanked by one or more non-guanidino/non-amidino subunits (such as glycine, alanine, and cysteine, for example), or a linker (such as an aminocaproic acid group), that do not significantly affect the rate of trans-tissue layer transport of the corresponding delivery-enhancing transporter-containing conjugates. Also, any free amino terminal group can be capped with a blocking group, such as an acetyl or benzyl group, to prevent ubiquitination in vivo.

Where the transporter is a peptoid polymer, one synthetic method involves the following steps: 1) a peptoid polyamine is treated with a base and pyrazole-1-carboxamidine to provide a mixture; 2) the mixture is heated and then allowed to cool; 3) the cooled mixture is acidified; and 4) the acidified mixture is purified. Preferably the base used in step 1 is a carbonate, such as sodium carbonate, and heating step 2 involves heating the mixture to approximately 50° C. for between about 24 hours and about 48 hours. The purification step preferably involves chromatography (e.g., reverse-phase HPLC).

D. Attachment of Transport Polymers To Biologically Active Agents

The agent to be transported can be linked to the delivery-enhancing transporter according to a number of embodiments. In one embodiment, the agent is linked to a single delivery-enhancing transporter, either via linkage to a terminal end of the delivery-enhancing transporter or to an internal subunit within the reagent via a suitable linking group.

In a second embodiment, the agent is attached to more than one delivery-enhancing transporter, in the same manner as above. This embodiment is somewhat less preferred, since it can lead to crosslinking of adjacent cells.

In a third embodiment, the conjugate contains two agent moieties attached to each terminal end of the delivery-enhancing transporter. For this embodiment, it is presently preferred that the agent has a molecular weight of less than 10 kDa.

With regard to the first and third embodiments just mentioned, the agent is generally not attached to one any of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogeneous mixtures.

According to an important aspect of the present invention, it has been found by the applicants that attachment of a single delivery-enhancing transporter to any of a variety of types of biologically active agents is sufficient to substantially enhance the rate of uptake of an agent into and across one or more layers of epithelial and endothelial tissues, even without requiring the presence of a large hydrophobic moiety in the conjugate. In fact, attaching a large hydrophobic moiety can significantly impede or prevent cross-layer transport due to adhesion of the hydrophobic moiety to the lipid bilayer of cells that make up the epithelial or endothelial tissue. Accordingly, the present invention includes conjugates that do not contain substantially hydrophobic moieties, such as lipid and fatty acid molecules.

Delivery-enhancing transporters of the invention can be attached covalently to biologically active agents by chemical or recombinant methods.

1. Chemical Linkages

Biologically active agents such as small organic molecules and macromolecules can be linked to delivery-enhancing transporters of the invention via a number of methods known in the art (see, for example, Wong, S. S., Ed., *Chemistry of Protein Conjugation and Cross-Linking*, CRC Press, Inc., Boca Raton, Fla. (1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the biologically active agent to the transport polymer. Groups which are not known to be part of an active site of the biologically active agent are preferred, particularly if the polypeptide or any portion thereof is to remain attached to the substance after delivery.

Polymers, such as peptides produced as described in PCT application US98/10571 (Publication No. WO 9852614), are generally produced with an amino terminal protecting group, such as FMOC. For biologically active agents which can survive the conditions used to cleave the polypeptide from the synthesis resin and deprotect the sidechains, the FMOC may be cleaved from the N-terminus of the completed resin-bound polypeptide so that the agent can be linked to the free N-terminal amine. In such cases, the agent to be attached is typically activated by methods well known in the art to produce an active ester or active carbonate moiety effective to form an amide or carbamate linkage, respectively, with the polymer amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N-NO$_2$, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

2. Fusion Polypeptides

Delivery-enhancing transporters of the invention can be attached to biologically active polypeptide agents by recombinant means by constructing vectors for fusion proteins comprising the polypeptide of interest and the delivery-enhancing transporter, according to methods well known in the art. Generally, the delivery-enhancing transporter component will be attached at the C-terminus or N-terminus of the polypeptide of interest, optionally via a short peptide linker.

3. Releasable Linkers

The biologically active agents are, in presently preferred embodiments, attached to the delivery-enhancing transporter using a linkage that is specifically cleavable or releasable. The use of such linkages is particularly important for biologically active agents that are inactive until the attached delivery-enhancing transporter is released. In some cases, such conjugates that consist of a drug molecule that is attached to a delivery-enhancing transporter can be referred to as prodrugs, in that the release of the delivery-enhancing transporter from the drug results in conversion of the drug from an inactive to an active form. As used herein, "cleaved" or "cleavage" of a conjugate or linker refers to release of a biological agent from a transporter molecule, thereby releasing an active biological agent. "Specifically cleavable" or "specifically releasable" refers to the linkage between the transporter and the agent being cleaved, rather than the transporter being degraded (e.g., by proteolytic degradation).

In some embodiments, the linkage is a readily cleavable linkage, meaning that it is susceptible to cleavage under conditions found in vivo. Thus, upon passing into and through one or more layers of an epithelial and/or endothelial tissue, the agent is released from the delivery-enhancing transporter. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The linkage can be selected so it is cleavable by an enzymatic activity that is known to be present in one or more layers of an epithelial or endothelial tissue. For example, the stratum granulosum of skin has a relatively high concentration of N-peptidase activity.

A specifically cleavable linker can be engineered onto a transporter molecule. For example, amino acids that constitute a protease recognition site, or other such specifically recognized enzymatic cleavage site, can be used to link the transporter to the agent. Alternatively, chemical or other types of linkers that are cleavable by, for example, exposure to light or other stimulus can be used to link the transporter to the agent of interest.

A conjugate in which an agent to be delivered and a delivery-enhancing transporter are linked by a specifically cleavable or specifically releasable linker will have a half-life. The term "half-life" in this context refers to the amount of time required after applying the conjugate to an epithelial or endothelial membrane for one half of the amount of conjugate to become dissociated to release the free agent. The half-life for some embodiments is typically between 5 minutes and 24 hours, and more preferably is between 30 minutes and 2 hours. The half-life of a conjugate can be "tuned" or modified, according to the invention, as described below.

In some embodiments, the cleavage rate of the linkers is pH dependent. For example, a linker can form a stable linkage between an agent and a delivery-enhancing transporter at an acidic pH (e.g., pH 6.5 or less, more preferably about 6 or less, and still more preferably about 5.5 or less). However, when the conjugate is placed at physiological pH (e.g., pH 7 or greater, preferably about pH 7.4), the linker will undergo cleavage to release the agent. Such pH sensitivity can be obtained by, for example, including a functional group that, when protonated (i.e., at an acidic pH), does not act as a nucleophile. At a higher (e.g., physiological) pH, the functional group is no longer protonated and thus can act as a nucleophile. Examples of suitable functional groups include, for example, N and S. One can use such functional groups to fine-tune the pH at which self-cleavage occurs.

The cleavable linker can be self-immolating. Such linkers contain a nucleophile (e.g., oxygen, nitrogen or sulfur) distal to the agent and a cleavable group (e.g., ester, carbonate, carbamate, thiocarbamate) proximal to the agent. Intramolecular attack of the nucleophile on the cleavable group either directly or indirectly releases the agent. In general, the nucleophile is 5 to 6 atoms distal from the cleaved group, thereby forming a 5–6 member ring as a product of immolation.

Such linkers include those having a structure 3, 4, or 5, as follows:

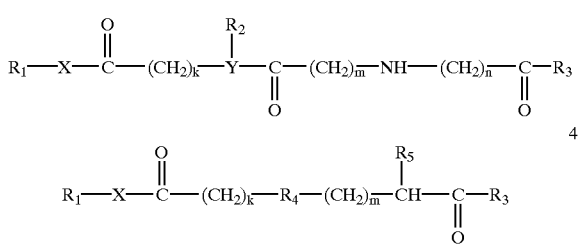

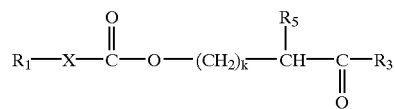

wherein:

$R_1$—X comprises the agent to be delivered;

X is a functional group on the agent, to which functional group the linker is attached;

Y is N or C;

$R_2$ is hydrogen, alkyl, aryl, acyl, or allyl;

$R_3$ comprises the delivery-enhancing transporter;

$R_4$ is substituted or unsubstituted S, O, N or C;

$R_5$ is OH, SH or $NHR_6$;

$R_6$ is hydrogen, alkyl, aryl, acyl or allyl;

k and m are each independently selected from 1 and 2; and n is 1 to 10.

The agent to be delivered (e.g., a drug or diagnostic agent) generally includes a functional group (designated as X in the formulae above) by which the linker is attached to the delivery-enhancing transporter. Examples of suitable functional groups for X include, for example, N, O, S, and $CR_7R_8$, wherein $R_7$ and $R_8$ are each independently selected from the group consisting of H and alkyl. If X is O, for example, release of the agent from the delivery-enhancing transporter and linker will yield the agent in its free alcohol form; if X is N, the free amine will result. Similarly, if X is S, release of the linker will yield the agent in the thiol form.

For a linker having the structure 3, one can adjust the half-life of a conjugate that includes the linker by the choice of the $R_2$ substituent. By using an $R_2$ of increased or decreased size, one can obtain a conjugate that has a longer or shorter half-life, respectively. $R_2$ is preferably methyl, ethyl, propyl, butyl, allyl, benzyl or phenyl. Similar modulation of half-life can be accomplished in an analogous manner with other linkers (e.g., $R_5$ on structure 4).

Structure 3 also provides an example of how the linker structure can affect the pH sensitivity of a conjugate. The backbone amino group is protonated at acidic pH (e.g., pH 5.5), and thus is stable in that the amine does not function as a strong nucleophile. Upon raising the pH to physiological pH (e.g., pH 7.4), however, the amine is no longer protonated and thus can act as a nucleophile. The resulting nucleophilic attack by the amine upon the carbonyl adjacent to the agent of interest then results in release of the agent from the linker and delivery-enhancing transporter. Again, this rationale also applies to other linker structures. In an example of a preferred linker of structure 3, $R_2$ is benzyl; k, m, and n are each 1, and X is O.

An example of a suitable linker of structure 4 has $R_5$ as $NHR_6$; $R_6$ selected from hydrogen, methyl, allyl, butyl or phenyl; and k and m each being 1.

Another example of a self-immolating linker is represented by structure 5 as shown above. In presently preferred conjugates that include linkers of this structure, $R_4$ is S and $R_5$ is $NHR_6$, wherein $R_6$ is hydrogen, methyl, allyl, butyl or phenyl; and k is 2.

For example, a presently preferred conjugate comprises the structure:

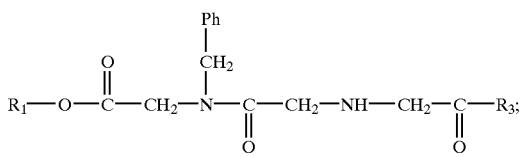

wherein Ph is phenyl.

The invention also provides linkers in which cleavage occurs in two stages. The first stage of cleavage is rate-limiting and can also be fine-tuned for pH sensitivity and half-life. Once this initial rearrangement has occurred, the second stage of the intramolecular reaction occurs relatively quickly. An example of a conjugate having this type of linker is represented as structure 6:

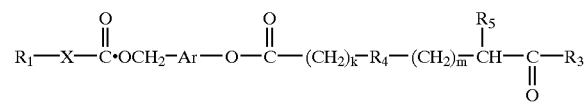

wherein:
$R_1$—X is the agent to be delivered;
X is a functional group on the agent, to which functional group the linker is attached;
Ar is an aryl group having the attached radicals arranged in an ortho or para configuration, which aryl group can be substituted or unsubstituted;
$R_3$ is the delivery-enhancing transporter;
$R_4$ is substituted or unsubstituted S, O, N or C;
$R_5$ is OH, SH or $NHR_6$;
$R_6$ is hydrogen, alkyl, aryl, acyl or allyl; and
k and m are each independently selected from 1 and 2.

Examples of preferred conjugates of structure 6 include those in which $R_4$ is S, $R_5$ is $NHR_6$, and $R_6$ is hydrogen, methyl, allyl, butyl or phenyl. For example, a suitable conjugate of structure 6 is:

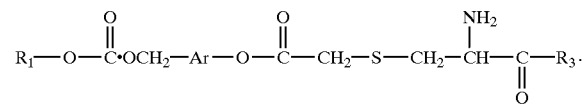

The self-immolating linkers typically undergo intramolecular cleavage with a half-life between about 10 minutes and about 24 hours in water at a pH of approximately 7.4. Preferably, the cleavage half-life is between about 20 minutes and about 4 hours in water at a pH of approximately 7.4. More preferably, the cleavage half-life is between about 30 minutes and about 2 hours in water at a pH of approximately 7.4.

In another preferred embodiment, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer. This embodiment is illustrated by various small molecule conjugates discussed below and in PCT application US98/10571 (Publication No. WO 9852614).

Figure 5A:
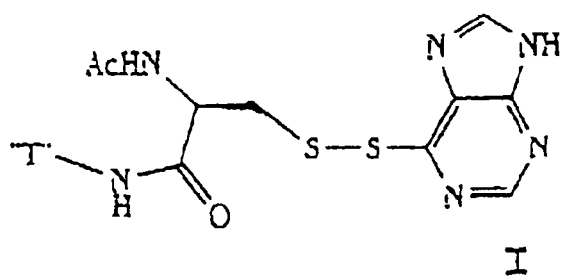
FIGS. 5A–H show various types of cleavable linkers that can be used to link a delivery-enhancing transporter to a biologically active agent or other molecule of interest.

In one approach, the conjugate can include a disulfide linkage, as illustrated in FIG. 5A (see also, PCT application US98/10571 (Publication No. WO 9852614)), which shows a conjugate (I) containing a transport polymer T which is linked to a cytotoxic agent, 6-mercaptopurine, by an N-acetyl-protected cysteine group which serves as a linker. Thus, the cytotoxic agent is attached by a disulfide bond to the 6-mercapto group, and the transport polymer is bound to the cysteine carbonyl moiety via an amide linkage. Cleavage of the disulfide bond by reduction or disulfide exchange results in release of the free cytotoxic agent.

A method for synthesizing a disulfide-containing conjugate is provided in Example 9A of PCT application US98/10571. The product contains a heptamer of Arg residues (SEQ ID NO:3) which is linked to 6-mercaptopurine by an N-acetyl-Cys-Ala-Ala linker, where the Ala residues are included as an additional spacer to render the disulfide more accessible to thiols and reducing agents for cleavage within a cell. The linker in this example also illustrates the use of amide bonds, which can be cleaved enzymatically within a cell.

Figure 5B:
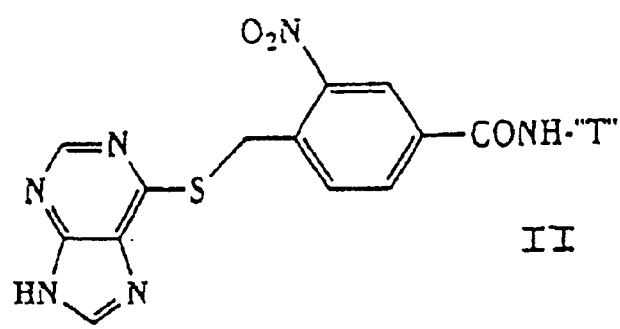

In another approach, the conjugate includes a photocleavable linker which is cleaved upon exposure to electromagnetic radiation. An exemplary linkage is illustrated in FIG. 5B, which shows a conjugate (II) containing a transport polymer T which is linked to 6-mercaptopurine via a meta-nitrobenzoate linking moiety. Polymer T is linked to the nitrobenzoate moiety by an amide linkage to the benzoate carbonyl group, and the cytotoxic agent is bound via its 6-mercapto group to the p-methylene group. The compound can be formed by reacting 6-mercaptopurine with p-bromomethyl-m-nitrobenzoic acid in the presence of $NaOCH_3$/methanol with heating, followed by coupling of the benzoate carboxylic acid to a transport polymer, such as the amino group of a γ-aminobutyric acid linker attached to the polymer (see e.g., Example 9B of PCT application US98/10571). Photo-illumination of the conjugate causes release of the 6-mercaptopurine by virtue of the nitro group that is ortho to the mercaptomethyl moiety. This approach finds utility in phototherapy methods as are known in the art, particularly for localizing drug activation to a selected area of the body.

Figure 5C:
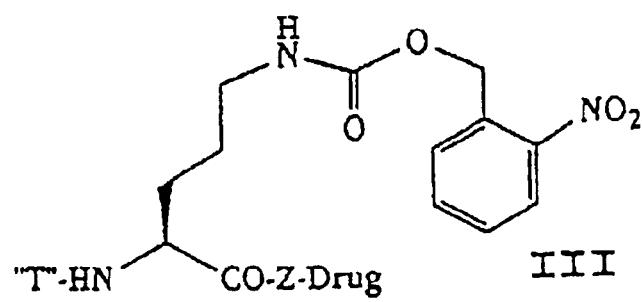

Preferably, the cleavable linker contains first and second cleavable groups that can cooperate to cleave the polymer from the biologically active agent, as illustrated by the following approaches. That is, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer:

FIG. 5C shows a conjugate (III) containing a transport polymer T linked to the anticancer agent, 5-fluorouracil (5FU). Here, the linkage is provided by a modified lysyl residue. The transport polymer is linked to the α-amino group, and the 5-fluorouracil is linked via the α-carbonyl. The lysyl ε-amino group has been modified to a carbamate ester of o-hydroxymethyl nitrobenzene, which comprises a first, photolabile cleavable group in the conjugate. Photo-illumination severs the nitrobenzene moiety from the conjugate, leaving a carbamate that also rapidly decomposes to give the free α-amino group, an effective nucleophile. Intramolecular reaction of the ε-amino group with the amide linkage to the 5-fluorouracil group leads to cyclization with release of the 5-fluorouracil group.

Figure 5D:
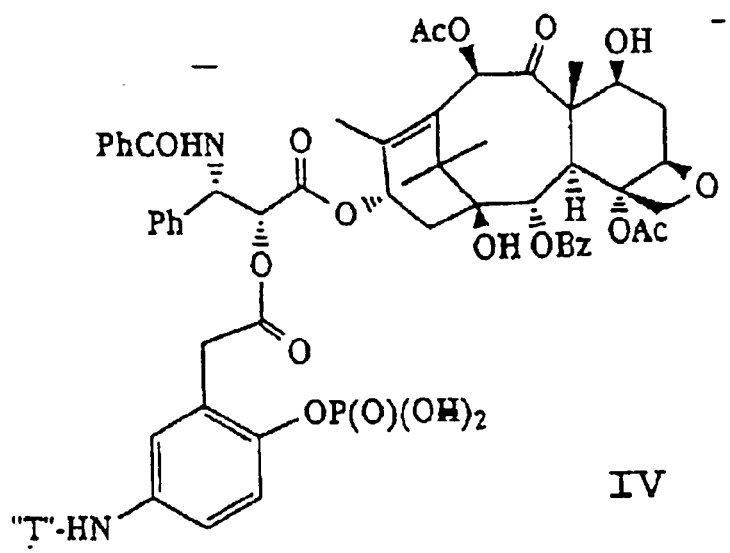

FIG. 5D illustrates a conjugate (IV) containing a delivery-enhancing transporter T linked to 2'-oxygen of the anticancer agent, paclitaxel. The linkage is provided by a linking moiety that includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. Enzymatic cleavage of the phosphate group from the conjugate affords a free phenol hydroxyl group. This nucleophilic group then reacts intramolecularly with the carboxylate ester to release free paclitaxel, fully capable of binding to its biological target. Example 9C of PCT application US98/10571 describes a synthetic protocol for preparing this type of conjugate.

Figure 5E:
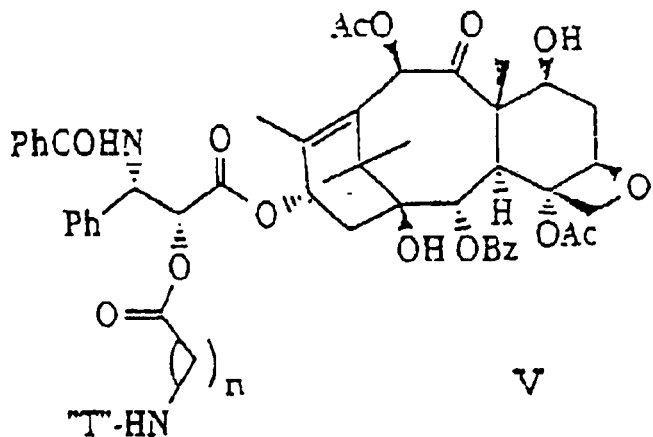

FIG. 5E illustrates yet another approach wherein a delivery-enhancing transporter is linked to a biologically active agent, e.g., paclitaxel, by an aminoalkyl carboxylic acid. Preferably, the linker amino group is linked to the linker carboxyl carbon by from 3 to 5 chain atoms (n=3 to 5), preferably either 3 or 4 chain atoms, which are preferably provided as methylene carbons. As seen in FIG. 5E, the linker amino group is joined to the delivery-enhancing transporter by an amide linkage, and is joined to the paclitaxel moiety by an ester linkage. Enzymatic cleavage of the amide linkage releases the delivery-enhancing transporter and produces a free nucleophilic amino group. The free amino group can then react intramolecularly with the ester group to release the linker from the paclitaxel.

Figure 6:
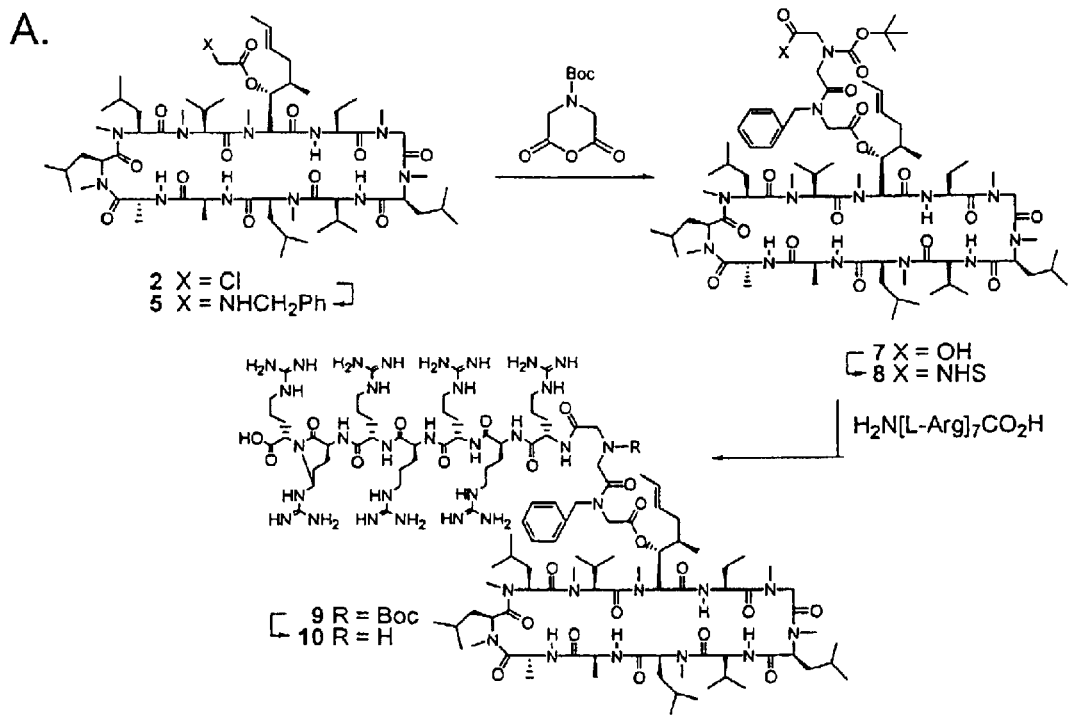
FIG. 6 displays a synthetic scheme for a chemical conjugate between a heptamer of L-arginine (SEQ ID NO:3) and cyclosporin A (panel A) and its pH dependent chemical release (SEQ ID NO:6) (panel B). The α-chloro ester (2) was treated with benzylamine in the presence of sodium iodide to effect substitution, giving the secondary amine (5). Amine (5) was treated with anhydride (6) and the resultant crude acid (7) was converted to its corresponding NHS ester (8). Ester (8) was then coupled with the amino terminus of hepta-L-arginine (SEQ ID NO:3), giving the N-Boc protected CsA conjugate (9). Finally, removal of the Boc protecting group with formic acid afforded the conjugate (10) as its octatrifluoroacetate salt after HPLC purification.
Figure 6:
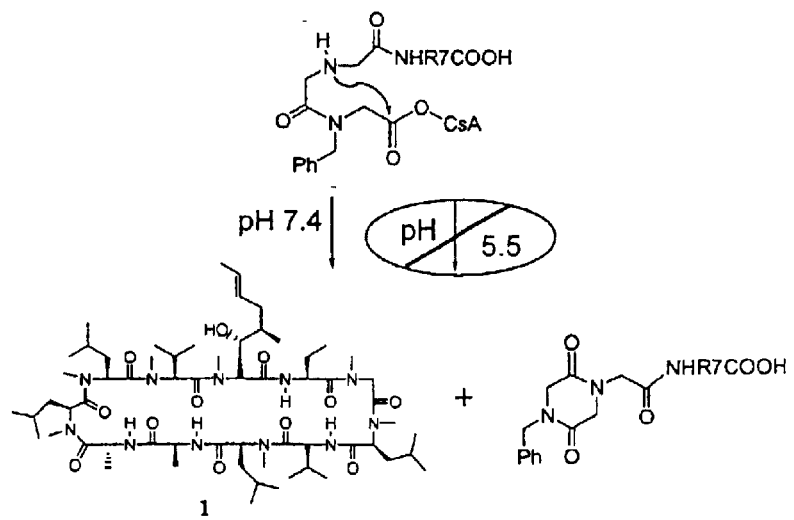

In another approach, the conjugate includes a linker that is labile at one pH but is stable at another pH. For example, FIG. 6 illustrates a method of synthesizing a conjugate with a linker that is cleaved at physiological pH but is stable at acidic pH. Preferably, the linker is cleaved in water at a pH of from about 6.6 to about 7.6. Preferably the linker is stable in water at a pH from about 4.5 to about 6.5.

Uses of Delivery-enhancing Transporters

The delivery-enhancing transporters find use in therapeutic, prophylactic and diagnostic applications. The delivery-enhancing transporters can carry a diagnostic or biologically active reagent into and across one or more layers of skin or other epithelial tissue (e.g., gastrointestinal, lung, and the like), or across endothelial tissues such as the blood brain barrier. This property makes the reagents useful for treating conditions by delivering agents that must penetrate across one or more tissue layers in order to exert their biological effect.

Compositions and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable pharmaceutical excipient as necessary can be carried out via any of the accepted modes of administration. Thus, administration can be, for example, intravenous, topical, subcutaneous, transcutaneous, intramuscular, oral, intra-joint, parenteral, peritoneal, intranasal, or by inhalation. Suitable sites of administration thus include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., *REMINGTON'S PHARMACEUTICAL SCIENCES,* 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences,* supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by the composition and stereochemistry of the backbone and sidechains of the delivery-enhancing transporters. For polypeptide delivery-enhancing transporters, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

A. Application to Skin

The delivery-enhancing transporters of the invention make possible the delivery of biologically active and diagnostic agents across the skin. Surprisingly, the transporters can deliver an agent across the stratum corneum, which previously had been a nearly impenetrable barrier to drug delivery. The stratum corneum, the outermost layer of the skin, is composed of several layers of dead, keratin-filled skin cells that are tightly bound together by a "glue" composed of cholesterol and fatty acids. Once the agents are delivered through the stratum corneum by the transporters of the invention, the agents can enter the viable epidermis, which is composed of the stratum granulosum, stratum lucidum and stratum germinativum which, along with the stratum corneum, make up the epidermis. Delivery in some embodiments of the invention is through the epidermis and into the dermis, including one or both of the papillary dermis and the reticular dermis.

This ability to obtain penetration of one or more layers of the skin can greatly enhance the efficacy of compounds such as antibacterials, antifungals, antivirals, antiproliferatives, immunosuppressives, vitamins, analgesics, hormones, and the like. Numerous such compounds are known to those of skill in the art (see, e.g., Hardman and Limbird, *Goodman & Gilman's The Pharmacological Basis of Therapeutics*, McGraw-Hill, New York, 1996).

In some embodiments, the agent is delivered into a blood vessel that is present in the epithelial tissue, thus providing a means for delivery of the agent systemically. Delivery can be either intrafollicular or interfollicular, or both. Pretreatment of the skin is not required for delivery of the conjugates.

In other embodiments, the delivery-enhancing transporters are useful for delivering cosmetics and agents that can treat skin conditions. Target cells in the skin that are of interest include, for example, fibroblasts, epithelial cells and immune cells. For example, the transporters provide the ability to deliver compounds such as antiinflammatory agents to immune cells found in the dermis.

Glucocorticoids (adrenocorticoid steroids) are among the compounds for which delivery across skin can be enhanced by the delivery-enhancing transporters of the invention. Conjugated glucocorticoids of the invention are useful for treating inflammatory skin diseases, for example. Exemplary glucocorticoids include, e.g., hydrocortisone, prenisone (deltasone) and predrisonlone (hydeltasol). Examples of particular conditions include eczema (including atopic dermatitis, contact dermatitis, allergic dermatitis), bullous disease, collagen vascular diseases, sarcoidosis, Sweet's disease, pyoderma gangrenosum, Type I reactive leprosy, capillary hemangiomas, lichen planus, exfoliative dermatitis, erythema nodosum, hormonal abnormalities (including acne and hirsutism), as well as toxic epidermal necrolysis, erythema multiforme, cutaneous T-cell lymphoma, discoid lupus erythematosus, and the like.

Retinoids are another example of a biologically active agent for which one can use the delivery-enhancing transporters of the invention to enhance delivery into and across one or more layers of the skin or other epithelial or endothelial tissue. Retinoids that are presently in use include, for example retinol, tretinoin, isotretinoin, etretinate, acitretin, and arotinoid. Conditions that are treatable using retinoids conjugated to the delivery-enhancing transporters of the invention include, but are not limited to, acne, keratinization disorders, skin cancer, precancerous conditions, psoriasis, cutaneous aging, discoid lupus erythematosus, scleromyxedema, verrucous epidermal nevus, subcorneal pustular dermatosis, Reiter's syndrome, warts, lichen planus, acanthosis nigricans, sarcoidosis, Grover's disease, porokeratosis, and the like.

Cytotoxic and immunosuppressive drugs constitute an additional class of drugs for which the delivery-enhancing transporters of the invention are useful. These agents are commonly used to treat hyperproliferative diseases such as psoriasis, as well as for immune diseases such as bullous dermatoses and leukocytoclastic vasculitis. Examples of such compounds that one can conjugate to the delivery-enhancing transporters of the invention include, but are not limited to, antimetabolites and alkylating agents. Useful biological agents include, e.g., methotrexate, azathioprine, fluorouracil, hydroxyurea, 6-thioquanine, mycophenolate, chlorambucil, vinicristine, vinblasrine, dactinomycin, cyclophosphamide, mechloroethamine hydrochloride, carmustine, taxol, tacrolimus, vinblastine, dapsone and sulfasalazine. Immunosuppressive drugs such as cyclosporin and Ascomycins, such as FK506 (tacrolimus), and rapamycin (e.g., U.S. Pat. No. 5,912,253) and analogs of such compounds are of particular interest (e.g., Mollinson et al., *Current Pharm. Design* 4(5):367–380 (1998); U.S. Pat. Nos. 5,612,350; 5,599,927; 5,604,294;5,990,131; 5,561,140; 5,859,031; 5,925,649; 5,994,299; 6,004,973 and 5,508,397). Cyclosporins include cyclosporin A, B, C, D, G and M. See, e.g., U.S. Pat. Nos. 6,007,840; and 6,004,973. For example, such compounds are useful in treating psoriasis, eczema (including atopic dermatitis, contact dermatitis, allergic dermatitis) and alopecia areata.

The delivery-enhancing transporters can be conjugated to agents that are useful for treating conditions such as lupus erythematosus (both discoid and systemic), cutaneous dermatomyositis, porphyria cutanea tarda and polymorphous light eruption. Agents useful for treating such conditions include, for example, quinine, chloroquine, hydroxychloroquine, and quinacrine.

The delivery-enhancing transporters of the invention are also useful for transdermal delivery of antiinfective agents. For example, antibacterial, antifungal and antiviral agents can be conjugated to the delivery-enhancing transporters. Antibacterial agents are useful for treating conditions such as acne, cutaneous infections, and the like. Antifungal agents can be used to treat tinea corporis, tinea pedis, onychomycosis, candidiasis, tinea versicolor, and the like. Because of the delivery-enhancing properties of the conjugates, these conjugates are useful for treating both localized and widespread infections. Antifungal agents are also useful for treating onychomycosis. Examples of antifungal agents include, but are not limited to, azole antifungals such as itraconazole, myconazole and fluconazole. Examples of antiviral agents include, but are not limited to, acyclovir, famciclovir, and valacyclovir. Such agents are useful for treating viral diseases, e.g., herpes.

Another example of a biologically active agent for which enhancement of delivery by conjugation to the delivery-enhancing transporters of the invention is desirable are the antihistamines. These agents are useful for treating conditions such as pruritus due to urticaria, atopic dermatitis, contact dermatitis, psoriasis, and many others. Examples of such reagents include, for example, terfenadine, astemizole, lorotadine, cetirizine, acrivastine, temelastine, cimetidine, ranitidine, famotidine, nizatidine, and the like. Tricyclic antidepressants can also be delivered using the delivery-enhancing transporters of the invention.

Topical antipsoriasis drugs are also of interest. Agents such as corticosteroids, calcipotriene, and anthralin can be conjugated to the delivery-enhancing transporters of the invention and applied to skin.

The delivery-enhancing transporters of the invention are also useful for enhancing delivery of photochemotherapeutic agents into and across one or more layers of skin and other epithelial tissues. Such compounds include, for example, the psoralens, and the like. Sunscreen components are also of interest; these include p-aminobenzoic acid esters, cinnamates and salicylates, as well as benzophenones, anthranilates, and avobenzone.

Pain relief agents and local anesthetics constitute another class of compounds for which conjugation to the delivery-enhancing transporters of the invention can enhance treatment. Lidocaine, bupibacaine, novocaine, procaine, tetracaine, benzocaine, cocaine, and the opiates, are among the compounds that one can conjugate to the delivery-enhancing transporters of the invention.

Other biological agents of interest include, for example, minoxidil, keratolytic agents, destructive agents such as podophyllin, hydroquinone, capsaicin, masoprocol, colchicine, and gold.

B. Gastrointestinal Administration

The delivery-enhancing transporters of the invention are also useful for delivery of conjugated drugs by gastrointestinal administration. Gastrointestinal administration can be used for both systemically active drugs, and for drugs that act in the gastrointestinal epithelium.

Among the gastrointestinal conditions that are treatable using appropriate reagents conjugated to the delivery-enhancing transporters are Crohn's disease (e.g., cyclosporin and FK506), ulcerative colitis, gastrointestinal ulcers, peptic ulcer disease, imbalance of salt and water absorption (can lead to constipation, diarrhea, or malnutrition), abnormal proliferative diseases, and the like. Ulcer treatments include, for example, drugs that reduce gastric acid secretion, such as $H_2$ histamine inhibitors (e.g., cymetidine and ranitidine) and inhibitors of the proton-potassium ATPase (e.g., lansoprazle amd omeprazle), and antibiotics directed at *Helicobacter pylori*.

Antibiotics are among the biologically active agents that are useful when conjugated to the delivery-enhancing transporters of the invention, particularly those that act on invasive bacteria, such as Shigella, Salmonella, and Yersinia. Such compounds include, for example, norfloxacin, ciprofloxacin, trimethoprim, sulfamethyloxazole, and the like.

Anti-neoplastic agents can also be conjugated to the delivery-enhancing transporters of the invention and administered by the gastrointestinal route. These include, for example, cisplatin, methotrexate, taxol, fluorouracil, mercaptopurine, donorubicin, bleomycin, and the like.

C. Respiratory Tract Administration

The delivery-enhancing transporters of the invention can also used to enhance administration of drugs through the respiratory tract. The respiratory tract, which includes the nasal mucosa, hypopharynx, and large and small airway structures, provides a large mucosal surface for drug absorption. The enhanced penetration of the conjugated agents into and across one or more layers of the epithelial tissue that is provided by the delivery-enhancing transporters of the invention results in amplification of the advantages that respiratory tract delivery has over other delivery methods. For example, lower doses of an agent are often needed to obtain a desired effect, a local therapeutic effect can occur more rapidly, and systemic therapeutic blood levels of the agent are obtained quickly. Rapid onset of pharmacological activity can result from respiratory tract administration. Moreover, respiratory tract administration generally has relatively few side effects.

The transporters of the invention can be used to deliver biological agents that are useful for treatment of pulmonary conditions. Examples of conditions treatable by nasal administration include, for example, asthma. These compounds include antiinflammatory agents, such as corticosteroids, cromolyn, and nedocromil, bronchodialators such as $\beta 2$-selective adronergic drugs and theophylline, and immunosuppressive drugs (e.g., cyclosporin and FK506). Other conditions include, for example, allergic rhinitis (which can be treated with glucocorticoids), and chronic obstructive pulmonary disease (emphysema). Other drugs that act on the pulmonary tissues and can be delivered using the transporters of the invention include beta-agonists, mast cell stabilizers, antibiotics, antifungal and antiviral agents, surfactants, vasoactive drugs, sedatives and hormones.

Respiratory tract administration is useful not only for treatment of pulmonary conditions, but also for delivery of drugs to distant target organs via the circulatory system. A wide variety of such drugs and diagnostic agents can be administered through the respiratory tract after conjugation to the delivery-enhancing transporters of the invention.

D. Delivery of Agents across the Blood Brain Barrier

The delivery-enhancing transporters are also useful for delivering biologically active and diagnostic agents across the blood brain barrier. The agents are useful for treating ischemia (e.g., using an anti-apoptotic drug), as well as for delivering neurotransmitters and other agents for treating various conditions such as schizophrenia, Parkinson's disease, pain (e.g., morphine, the opiates). The 5-hydroxytryptamine receptor antagonist is useful for treating conditions such as rmigraine headaches and anxiety.

E. Diagnostic imaging and contrast agents

The delivery-enhancing transporters of the invention are also useful for delivery of diagnostic imaging and contrast agents into and across one or more layers of an epithelial and/or endothelial tissue. Examples of diagnostic agents include substances that are labeled with radioactivity, such as $^{99}$ mTc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell (including, but not limited to, ($\beta$-galactosidase, green fluorescent protein, luciferase, and the like. A wide variety of labels may be employed, such as radionuclides, fluors, enzymes, enzyme substrates, enzyme cofactors, enzyme inhibitors, ligands (particularly haptens), etc.

Biologically-Active and Diagnostic Molecules Useful with the Delivery-enhancing Transporters The delivery-enhancing transporters can be conjugated to a wide variety of biologically active agents and molecules that have diagnostic use.

A. Small Organic Molecules

Small organic molecule therapeutic agents can be advantageously attached to linear polymeric compositions as described herein, to facilitate or enhance transport across one or more layers of an epithelial or endothelial tissue. For example, delivery of highly charged agents, such as levodopa (L-3,4-dihydroxy-phenylalanine; L-DOPA) may benefit by linkage to delivery-enhancing transporters as described herein. Peptoid and peptidomimetic agents are also contemplated (e.g., Langston (1997) *DDT* 2:255; Giannis et al. (1997) *Advances Drug Res.* 29:1). Also, the invention is advantageous for delivering small organic molecules that have poor solubilities in aqueous liquids, such as serum and aqueous saline. Thus, compounds whose therapeutic efficacies are limited by their low solubilities can be administered in greater dosages according to the present invention, and can be more efficacious on a molar basis in conjugate form, relative to the non-conjugate form, due to higher uptake levels by cells.

Since a significant portion of the topological surface of a small molecule is often involved, and therefore required, for biological activity, the small molecule portion of the conjugate in particular cases may need to be severed from the attached delivery-enhancing transporter and linker moiety (if any) for the small molecule agent to exert biological activity after crossing the target epithelial tissue. For such situations, the conjugate preferably includes a cleavable linker for releasing free drug after passing through an epithelial tissue.

FIG. 5D and FIG. 5E are illustrative of another aspect of the invention, comprising taxane- and taxoid anticancer conjugates which have enhanced trans-epithelial tissue transport rates relative to corresponding non-conjugated forms. The conjugates are particularly useful for inhibiting growth of cancer cells. Taxanes and taxoids are believed to manifest their anticancer effects by promoting polymerization of microtubules (and inhibiting depolymerization) to an extent that is deleterious to cell function, inhibiting cell replication and ultimately leading to cell death.

Figure 5F:
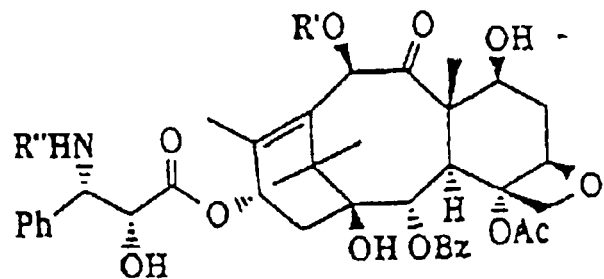
Figure 5G:
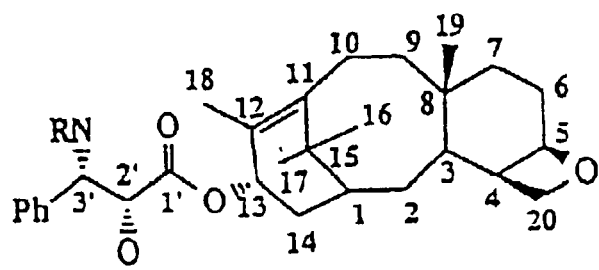
Figure 5H:
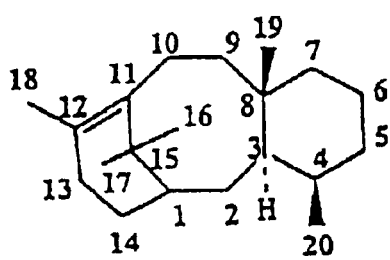

The term "taxane" refers to paclitaxel (FIG. 5F, R'=acetyl, R"=benzyl) also known under the trademark "TAXOL") and naturally occurring, synthetic, or bioengineered analogs having a backbone core that contains the A, B, C and D rings of paclitaxel, as illustrated in FIG. 5G. FIG. 5F also indicates the structure of "TAXOTERE™" (R'=H, R"=BOC), which is a somewhat more soluble synthetic analog of paclitaxel sold by Rhone-Poulenc. "Taxoid" refers to naturally occurring, synthetic or bioengineered analogs of paclitaxel that contain the basic A, B and C rings of paclitaxel, as shown in FIG. 5H. Substantial synthetic and biological information is available on syntheses and activities of a variety of taxane and taxoid compounds, as reviewed in Suffness (1995) *Taxol: Science and Applications*, CRC Press, New York, N.Y., pp. 237–239, particularly in Chapters 12 to 14, as well as in the subsequent paclitaxel literature. Furthermore, a host of cell lines are available for predicting anticancer activities of these compounds against certain cancer types, as described, for example, in Suffness at Chapters 8 and 13.

The delivery-enhancing transporter is conjugated to the taxane or taxoid moiety via any suitable site of attachment in the taxane or taxoid. Conveniently, the transport polymer is linked via a C2'-oxygen atom, C7-oxygen atom, using linking strategies as above. Conjugation of a transport polymer via a C7-oxygen leads to taxane conjugates that have anticancer and antitumor activity despite conjugation at that position. Accordingly, the linker can be cleavable or non-cleavable. Conjugation via the C2'-oxygen significantly reduces anticancer activity, so that a cleavable linker is preferred for conjugation to this site. Other sites of attachment can also be used, such as C10.

It will be appreciated that the taxane and taxoid conjugates of the invention have improved water solubility relative to taxol ($\approx$0.25 μg/mL) and taxotere (6–7 μg/mL). Therefore, large amounts of solubilizing agents such as "CREMOPHOR EL" (polyoxyethylated castor oil), polysorbate 80 (polyoxyethylene sorbitan monooleate, also known as "TWEEN 80"), and ethanol are not required, so that side-effects typically associated with these solubilizing agents, such as anaphylaxis, dyspnea, hypotension, and flushing, can be reduced.

B. Metals

Metals can be transported into and across one or more layers of epithelial and endothelial tissues using chelating agents such as texaphyrin or diethylene triamine pentacetic acid (DTPA), conjugated to a delivery-enhancing transporter of the invention, as illustrated by Example. These conjugates are useful for delivering metal ions for imaging or therapy. Exemplary metal ions include Eu, Lu, Pr, Gd, Tc99m, Ga67, In111, Y90, Cu67, and Co57. Preliminary membrane-transport studies with conjugate candidates can be performed using cell-based assays such as described in the Example section below. For example, using europium ions, cellular uptake can be monitored by time-resolved fluorescence measurements. For metal ions that are cytotoxic, uptake can be monitored by cytotoxicity.

C. Macromolecules

The enhanced transport methods of the invention are particularly suited for enhancing transport into and across one or more layers of an epithelial or endothelial tissue for a number of macromolecules, including, but not limited to proteins, nucleic acids, polysaccharides, and analogs thereof. Exemplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Analogs include charged and preferably uncharged backbone analogs, such as phosphonates (preferably methyl phosphonates), phosphoramidates (N3' or N5'), thiophosphates, uncharged morpholino-based polymers, and protein nucleic acids (PNAs). Such molecules can be used in a variety of therapeutic regimens, including enzyme replacement therapy, gene therapy, and anti-sense therapy, for example.

By way of example, protein nucleic acids (PNA) are analogs of DNA in which the backbone is structurally homomorphous with a deoxyribose backbone. The backbone consists of N-(2-aminoethyl)glycine units to which the nucleobases are attached. PNAs containing all four natural nucleobases hybridize to complementary oligonucleotides obeying Watson-Crick base-pairing rules, and is a true DNA mimic in terms of base pair recognition (Egholm et al. (1993) *Nature* 365:566–568. The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport polymer of the invention.

Figure 7:
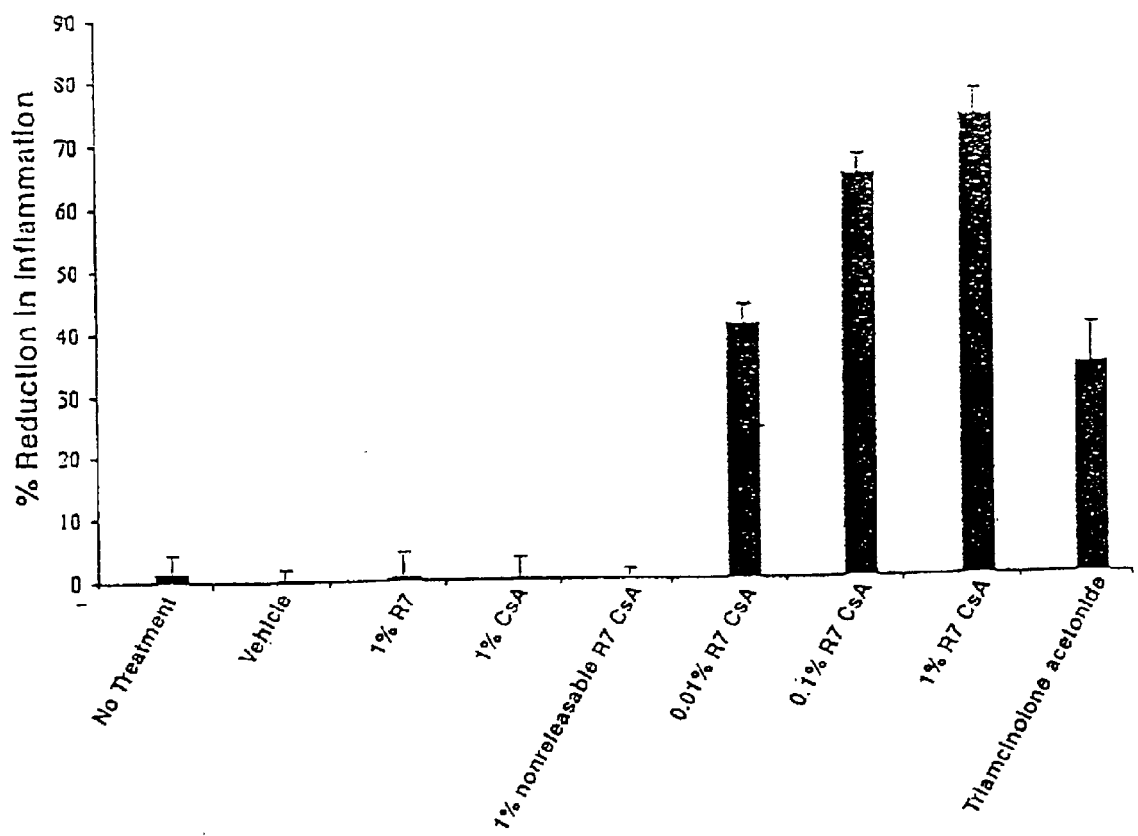
FIG. 7 displays inhibition of inflammation in murine contact dermatitis by releasable R7 CsA. Balb/c (6–7 weeks) mice were painted on the abdomen with 100 μl of 0.7% DNFB in acetone olive oil (95:5). Three days later both ears of the animals were restimulated with 0.5% DNFB in acetone. Mice were treated one, five, and twenty hours after restimulation with either vehicle alone, 1% R7 (SEQ ID NO:3) peptide alone, 1% CsA, 1% nonreleasable R7 CsA, 0.01%/0.1%/1.0% releasable R7 CsA, and the fluorinated steroid positive control 0.1% triamcinolone acetonide. Ear inflammation was measured 24 hours after restimulation using a spring loaded caliper. The percent reduction of inflammation was calculated using the following formula (t−n)/(μ−n), where t=thickness of the treated ear, n=the thickness of a normal untreated ear, and u=thickness of an inflamed ear without any treatment. N=20 animals in each group.

Examples of anti-sense oligonucleotides whose transport into and across epithelial and endothelial tissues can be enhanced using the methods of the invention are described, for example, in U.S. Pat. No. 5,594,122. Such oligonucleotides are targeted to treat human immunodeficiency virus (HIV). Conjugation of a transport polymer to an anti-sense oligonucleotide can be effected, for example, by forming an amide linkage between the peptide and the 5'-terminus of the oligonucleotide through a succinate linker, according to well-established methods. The use of PNA conjugates is further illustrated in Example 11 of PCT Application PCT/US98/10571. FIG. 7 of that application shows results obtained with a conjugate of the invention containing a PNA sequence for inhibiting secretion of gamma-interferon (γ-IFN) by T cells, as detailed in Example 11. As can be seen, the anti-sense PNA conjugate was effective to block γ-IFN secretion when the conjugate was present at levels above about 10 µM. In contrast, no inhibition was seen with the sense-PNA conjugate or the non-conjugated antisense PNA alone.

Another class of macromolecules that can be transported across one or more layers of an epithelial or endothelial tissue is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetylglucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuromuscular dysfunction associated with triose phosphate isomerase deficiency.

In addition, and according to an important aspect of the invention, protein antigens may be delivered to the cytosolic compartment of antigen-presenting cells (APCs), where they are degraded into peptides. The peptides are then transported into the endoplasmic reticulum, where they associate with nascent HLA class I molecules and are displayed on the cell surface. Such "activated" APCs can serve as inducers of class I restricted antigen-specific cytotoxic T-lymphocytes (CTLs), which then proceed to recognize and destroy cells displaying the particular antigen. APCs that are able to carry out this process include, but are not limited to, certain macrophages, B cells and dendritic cells. In one embodiment, the protein antigen is a tumor antigen for eliciting or promoting an immune response against tumor cells. The transport of isolated or soluble proteins into the cytosol of APC with subsequent activation of CTL is exceptional, since, with few exceptions, injection of isolated or soluble proteins does not result either in activation of APC or induction of CTLs. Thus, antigens that are conjugated to the transport enhancing compositions of the present invention may serve to stimulate a cellular immune response in vitro or in vivo.

In another embodiment, the invention is useful for delivering immunospecific antibodies or antibody fragments to the cytosol to interfere with deleterious biological processes such as microbial infection. Recent experiments have shown that intracellular antibodies can be effective antiviral agents in plant and mammalian cells (e.g., Tavladoraki et al. (1993) *Nature* 366:469; and Shaheen et al. (1996) *J. Virol.* 70:3392. These methods have typically used single-chain variable region fragments (scFv), in which the antibody heavy and light chains are synthesized as a single polypeptide. The variable heavy and light chains are usually separated by a flexible linker peptide (e.g., of 15 amino acids) to yield a 28 kDa molecule that retains the high affinity ligand binding site. The principal obstacle to wide application of this technology has been efficiency of uptake into infected cells. But by attaching transport polymers to scFv fragments, the degree of cellular uptake can be increased, allowing the immunospecific fragments to bind and disable important microbial components, such as HIV Rev, HIV reverse transcriptase, and integrase proteins.

D. Peptides

Peptides to be delivered by the enhanced transport methods described herein include, but should not be limited to, effector polypeptides, receptor fragments, and the like. Examples include peptides having phosphorylation sites used by proteins mediating intra-cellular signals. Examples of such proteins include, but are not limited to, protein kinase C, RAF-1, p21Ras, NF-κB, C-JUN, and cytoplasmic tails of membrane receptors such as IL-4 receptor, CD28, CTLA-4, V7, and MHC Class I and Class II antigens.

When the delivery-enhancing transporter is also a peptide, synthesis can be achieved either using an automated peptide synthesizer or by recombinant methods in which a polynucleotide encoding a fusion peptide is produced, as mentioned above.

EXAMPLES

The following examples are offered to illustrate, but not to limit the present invention.

Example 1

Penetration of Biotinylated Polymers of D-arginine into the Skin of Nude Mice

This Example demonstrates that poly-arginine heptamers can deliver conjugated biotin into and across layers of the skin, both follicularly and interfollicularly, and into the dermis.

Methods

Biotinylated peptides were synthesized using solid phase techniques and commercially available Fmoc amino acids, resins, and reagents (PE Biosystems, Foster City Calif., and Bachem Torrence, Calif.) on a Applied Biosystems 433 peptide synthesizer. Fastmoc cycles were used with O-(7-azabenzotriazol-1-yl)-1,1,3,3-tetramethyluronium hexfluorophosphate (HATU) substituted for HBTU/HOBt as the coupling reagent. Prior to the addition of biotin to the amino terminus of the peptide, amino caproic acid (aca) was conjugated and acted as a spacer. The peptides were cleaved from the resin using 96% trifluoroacetic acid, 2% triisopropyl silane, and 2% phenol for between 1 and 12 hours. The longer reaction times were necessary to completely remove the Pbf protecting groups from the polymers of arginine. The peptides subsequently were filtered from the resin, precipitated using diethyl ether, purified using HPLC reverse phase columns (Alltech Altima, Chicago, Ill.) and characterized using either electrospray or matrix assisted laser desorption mass spectrometry (Perceptive Biosystems, Boston, Mass.).

Varying concentrations (1 mM–10 μM) of a heptamer of D-arginine with biotin covalently attached to the amino terminus using an amino caproic acid spacer (bio r7), dissolved in phosphate buffered saline (PBS), were applied to the back of anesthetized nude mice. Samples (100 μl) were applied as a liquid without excipient, prevented from dispersing by a Vaseline™ barrier, and allowed to penetrate for fifteen minutes. At the end of this period the animal was sacrificed, the relevant sections of skin were excised, embedded in mounting medium (OCT), and frozen. Frozen sections (5 microns) were cut using a cryostat, collected on slides, and stained with fluorescently labeled streptavidin (Vector Laboratories, Burlingame, Calif.). The slides were fixed in acetone at 4° C. for ten minutes, air dried, soaked in PBS for five minutes, blocked with normal goat serun for five minutes, and washed with PBS for five minutes. The section was stained by incubation with fluorescently labeled streptavidin at 30 μg/ml for thirty minutes, washed with PBS, counterstained with propidium iodide (1 μg/ml) for two minutes, and the section was mounted with Vectashield™ mounting media. Slides were analyzed by fluorescent microscopy. Parallel studies were done using streptavidin-horse radish peroxidase rather than fluorescein-streptavidin. The biotinylated peptide was visualized by treatment of the sections with the horseradish peroxidase substrate diaminobenzadine, and visualization with light microscopy.

Results

Biotinylated arginine heptamer crossed into and across the epidermis and into the dermis. The cytosol and nuclei of all cells in the field were fluorescent, indicating penetration into virtually every cell of the nude mouse skin in the section. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone.

Example 2

Penetration of Biotinylated Polymers of D-arginine into the Skin of Normal Balb/C Mice Varying concentrations (1 mM–100 μM) of a heptamer of D-arginine with biotin covalently attached to the amino terminus using an amino caproic acid spacer (bio r7), dissolved in PBS, were applied to a skin of the groin of an anesthetized Balb/C mice. Sample (100 μl) was applied as a liquid within excipient and prevented from dispersing by a Vaseline™ barrier and allowed to penetrate for thirty minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

As with the skin from nude mice, biotinylated arginine heptamer crossed into and across the epidermis and into the dermis. The cytosol and nuclei of all cells in the field were fluorescent, indicating penetration into virtually every cell of the nude mouse skin in the section. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone.

Example 3

Penetration of Biotinylated Polymers of D-arginine into Normal Human Skin Grafted onto Nude Mice Varying concentrations (1 mM–100 μM) of a heptamer of D-arginine with biotin covalently attached to the amino terminus using an amino caproic acid spacer (bio r7), dissolved in PBS, were applied to human foreskin grafts on the back of SCID mice (see, e.g., Deng et al. (1997) *Nature Biotechnol.* 15: 1388–1391; Khavari et al. (1997) *Adv. Clin. Res.* 15:27–35; Choate and Khavari (1997) *Human Gene Therapy* 8:895–901). Samples (100 μl) were applied as a liquid within excipient and prevented from dispersing by a Vaseline™ barrier and allowed to penetrate for fifteen minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

As with the skin from nude and normal mice, biotinylated arginine heptamer crossed into and across the epidermis and into the dermis of the human skin. The cytosol and nuclei of all cells in the field were fluorescent, indicating penetration into and through the epidermis and dermis. Intense staining was seen at both 20× and 40×magnification. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone, and very little staining was observed with the biotinylated arginine pentamer conjugate, either at low or high magnification.

Example 4

Increased Penetration of Biotinylated Polymers of D-arginine into Skin of Nude Mouse Using Plastic Wrap or a Lotion Excipient Varying concentrations (1 mM–100 μM) of a heptamer of D-arginine with biotin covalently attached to the amino terminus using an amino caproic acid spacer (bio r7), dissolved in PBS, and mixed with an equal volume of Lubriderm™. The lotion mixture was then applied to the back of nude mice and allowed to penetrate for thirty, sixty, and 120 minutes. Alternatively, sample (100 μl) was applied as a liquid without excipient and prevented from evaporating by wrapping plastic wrap over the sample sealed with Vaseline™. The samples were allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

Both lotion and plastic wrap resulted in increased uptake compared with staining without excipient. Lotion was more effective than plastic wrap in enhancing uptake of the conjugate. Biotinylated arginine pentamers crossed into and across several skin layers, reaching both the cytosol and nuclei of epidermal cell layers, both follicular and interfollicular. In addition, positive cells were apparent in papillary and reticular dermis.

Example 5

Penetration of Cyclosporin Conjugated to a Biotinylated Pentamer, Heptamer, and Nonamer of D-arginine into the Skin of Nude Mice Methods A. Linking Cyclosporin to Delivery-enhancing Transporters 1. Preparation of the α-chloroacetyl Cyclosporin A derivative.

The α-chloroacetyl cyclosporin A derivative was prepared as shown in FIG. 1. Cyclosporin A (152.7 mg, 127 μmol) and chloroacetic acid anhydride (221.7 mg; 1300 μmol) were placed into a dry flask under $N_2$-atmosphere. Pyridine (1.0 mL) was added and the solution was heated to 50° C. (oil bath). After 16 hours the reaction was cooled to room temperature and quenched with water (4.0 mL). The resulting suspension was extracted with diethylether (Σ15 mL). The combined organic layers were dried over $MgSO_4$. Filtration and evaporation of solvents in vacuo delivered a yellow oil, which was purified by flash chromatography on silica gel (eluent: EtOAc/hexanes: 40%–80%) yielding 136 mg (106.4 μmol, 83%) of the desired product.

2. Coupling to Transporter molecules

Figure 2:
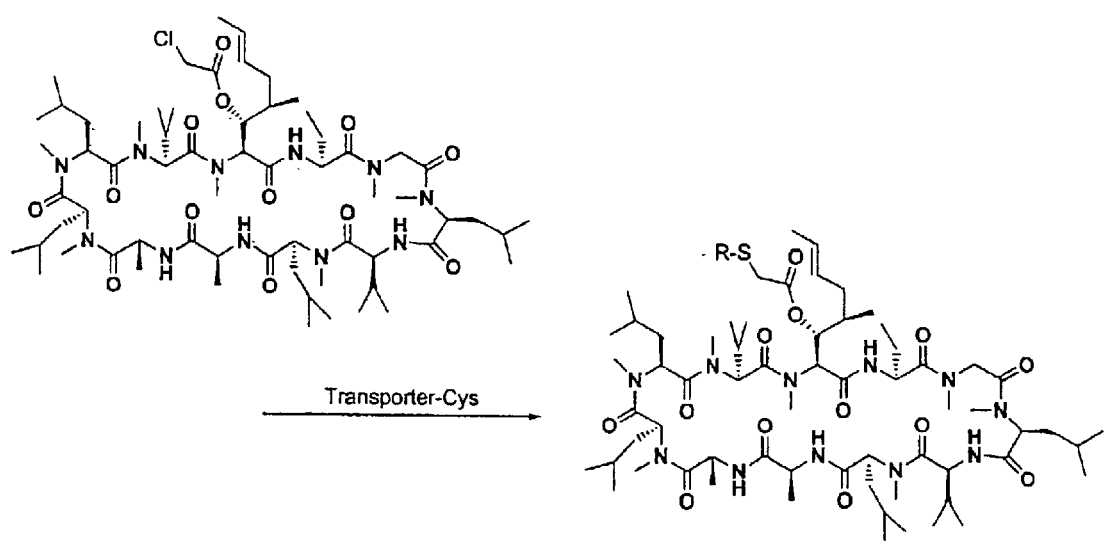
FIG. 2 shows a general procedure for the coupling, of cysteine-containing peptides to the α-chloro acetyl cyclosporin A derivative.

A general procedure for the coupling of cysteine containing peptides to the α-chloro acetyl Cyclosporin A derivative is shown in FIG. 2.

a. Labeled Peptides

Figure 3:
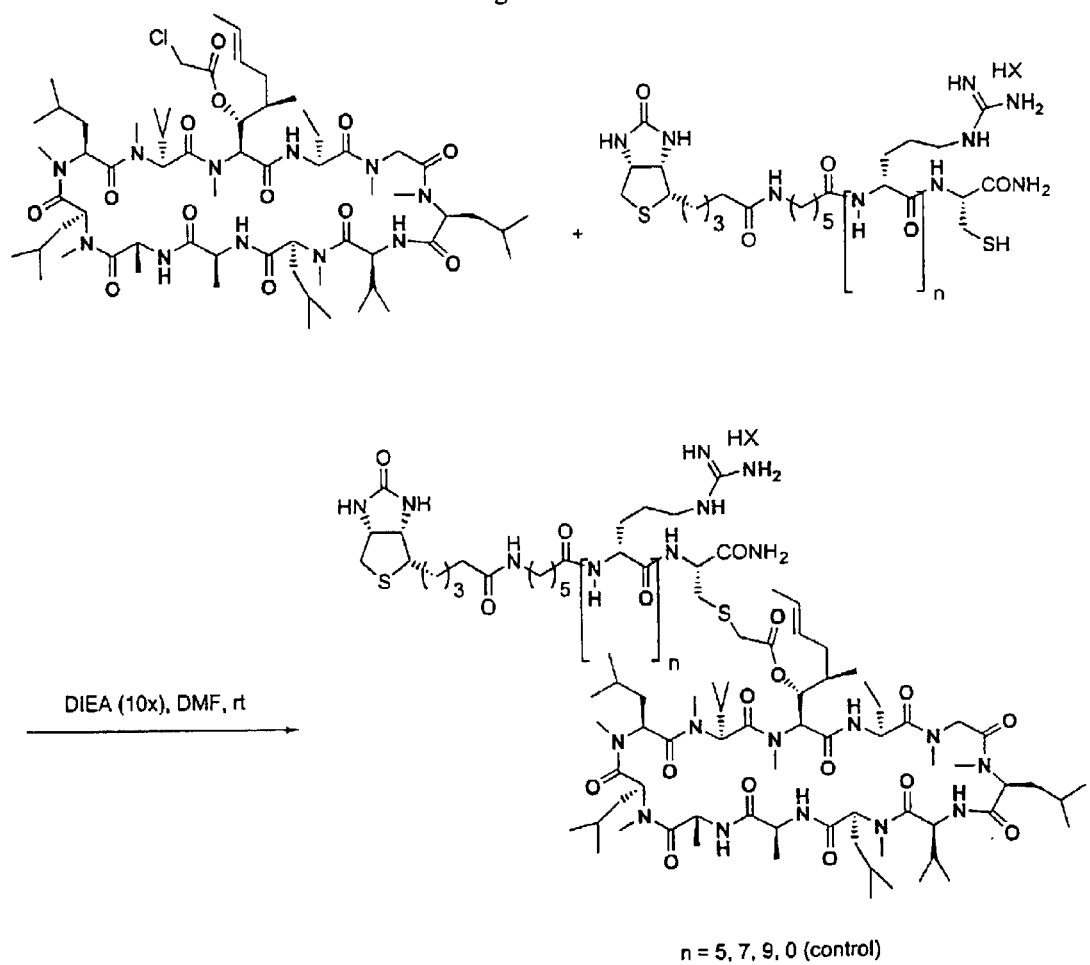
FIG. 3 shows a reaction scheme for the coupling of the cyclosporin A derivative to a biotin-labeled peptide (SEQ ID NOS:46–48).

The cyclosporin A derivative and the labeled peptide (1 equivalent) were dissolved in DMF (~10 mmol of Cyclosporin A derivative/mL DMF) under an $N_2$-atmosphere. Diisopropylethylamine (10 equivalents) was added and stirring at room temperature was continued until all starting material was consumed (usually after 16 hours) (FIG. 3). The solvents were removed in vacuo and the crude reaction product was dissolved in water and purified by reversed phase high pressure liquid chromatography (RP-HPLC) (eluent: water/MeCN *TFA). The products were obtained in the following yields:

B-aca-r5-Ala-Ala-Cys-O-acyl-Cyclosporin A: 47%
B-aca-r7-Cys-O-acyl-Cyclosporin A: 43%
B-aca-r9-Cys-O-acyl-Cyclosporin A: 34%
B-aca-Cys-O-acyl-Cyclosporin A: 55% b. Unlabeled Peptides

Figure 4:
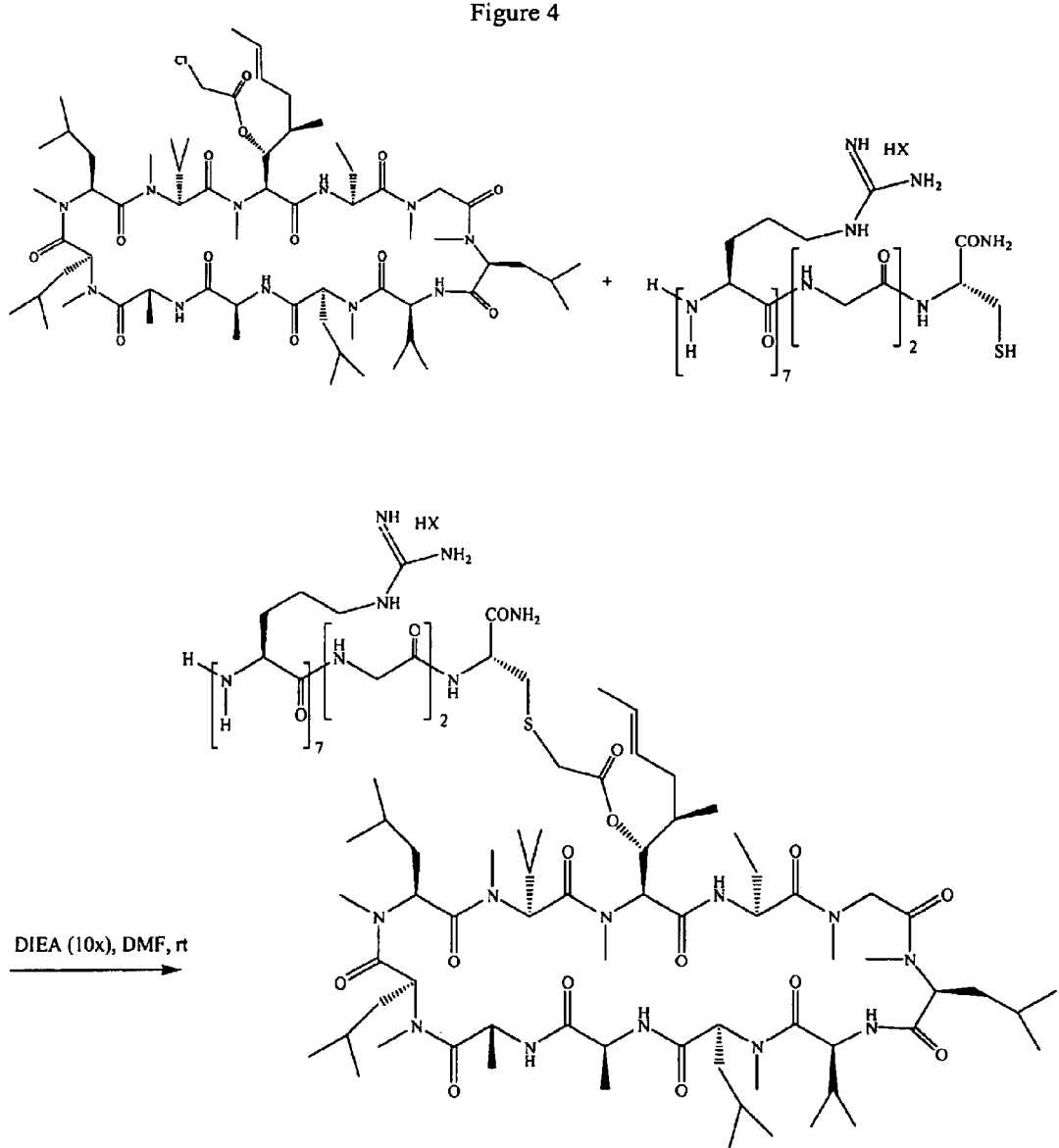
FIG. 4 shows a reaction scheme for coupling of a cyclosporin A derivative to an unlabeled peptide (SEQ ID NO:7).

The peptide (34.7 mg, 15.3 μmol) and the Cyclosporin A derivative (19.6 mg, 15.3 μmol) were dissolved in DMF (1.0 mL) under an $N_2$-atmosphere (FIG. 4). Disopropylethylamine (19.7 mg, 153 μmol) was added and stirring at room temperature was continued. After 12 hours the solvent was removed in vacuo. The crude material was dissolved in water and purified by RP-HPLC (eluent: water/MeCN *TFA) yielding the pure product (24.1 mg, 6.8 mmol, 44%).

B. Analysis of Transport Across Skin

Varying concentrations (1 mM–100 μM) of cyclosporin conjugated to either biotinylated pentamer, heptamer, or nonamers of D-arginine (bio r5, r7, or r9), dissolved in PBS, were applied to the back of nude mice. Samples (100 μl) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy Results The conjugates of cyclosporin with biotinylated heptamers and nonamers of D-arginine effectively entered into and across the epidermis and into the dermis of the skin of nude mice. In contrast, very little uptake was seen using a conjugate between a pentamer of arginine and cyclosporin, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 6

Demonstration That a D-arginine Heptamer Can Penetrate Human Skin

Human and murine skin differ significantly in a number of ways, with human epidermis being considerably thicker. To determine if the D-arginine heptamers/cyclosporin A (r7 CsA) conjugate could also penetrate human skin, biotin r7 CsA was applied to full thickness human skin grafted onto the back of a SCID mouse. As in murine skin, conjugated cyclosporin A penetrated human epidermis and dermis. Fluorescence was observed in both the cytosol and the nuclei of cells in tissue exposed to biotinylated peptides alone, but in sections stained with biotin r7 CsA the majority of fluorescence was cytosolic, consistent with r7 CsA binding to cyclosporin A's known cytoplasmic targets.

Example 7

Demonstration That Cyclosporin A-transporter Conjugates Enter T Cells in the Dermis Methods Inhibition of IL-2 secretion by releasable R7-CsA conjugate. Jurkat cells ($5 \times 10^4$) were incubated with varying concentrations of a nonreleasable or releasable R7-CsA conjugate or CsA overnight at 37° C. to allow for the release of the active form of CsA prior to stimulation with PMA and ionomycin. T cells subsequently were stimulated to produce IL-2 by addition of 10 ng/ml PMA (Sigma, St. Louis, Mo.) and 1 μM ionomycin (CalBiochem, San Diego, Calif.). Cultures were incubated overnight at 37° C. and supematants were collected and IL-2 was measured using a fluorescent ELISA. Briefly, plates were coated with 4 μg/ml anti-human IL-2 antibody (BD Pharmingen, San Diego, Calif.), blocked with PBS containing 10% FBS for 1 hour at room temperature, washed, and supernatants added and incubated for 1 hour. Media was removed and biotinylated anti-human IL-2 (1.6 μg/ml), was added for one hour. The plates were washed, and then europium labeled streptavidin (0.04 ng/ml) was added for one hour. After another wash, enhancement solution was added and the resulting fluorescence was measured using a Wallac plate reader (Wallac, Turku, Finland).

Results

To determine whether biotinylated D-arginine heptamer-cyclosporin (r7 CsA) conjugate would reach infiltrating T cells within inflamed skin in vivo, biotin r7 CsA was applied to the site of inflammation on the back of a mouse with experimentally induced contact dermatitis. Inflamed skin was stained with rhodamine labeled goat anti-mouse CD3 to localize T-cells and with fluorescein labeled streptavidin to localize the biotin r7 CsA. Biotin r7 CsA was found in all CD3[+] T cells in the tissue in addition to a variety of other cells that probably represent other inflammatory cells as well as resident fibroblasts. These data indicate that biotin r7 CsA penetrates inflamed skin to reach key target T lymphocytes.

Example 8

Figure 10:
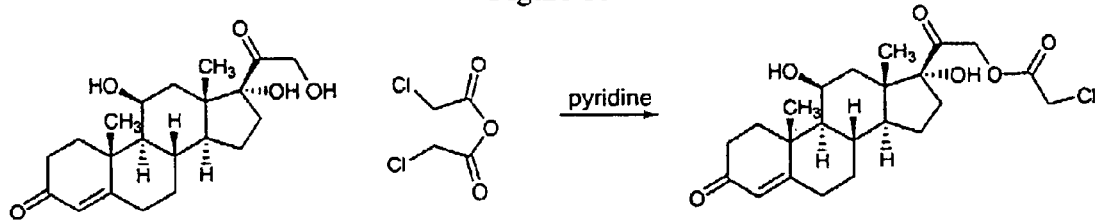
FIG. 10 shows a reaction for the acylation of hydrocortisone with chloroacetic anhydride.

Synthesis, in vitro and in vivo Activity of a Releasable Conjugate of a Short Oligomer of Arginine and CsA Modification of the 2° alcohol of Cyclosporin A results in significant loss of its biological activity. See, e.g., R. E. Handschumacher, et al., *Science* 226, 544–7 (1984). Consequently, to ensure release of free Cyclosporin A from its conjugate after transport into cells, Cyclosporin A was conjugated to an oligo-arginine transporter through a pH sensitive linker as shown in FIG. 10. The resultant conjugate is stable at acidic pH but at pH>7 it undergoes an intramolecular cyclization involving addition of the free amine to the carbonyl adjacent to Cyclosporin A (FIG. 6), which results in the release of unmodified Cyclosporin A.

Another modification in the design of the releasable conjugate was the use of L-arginine (R), and not D-arginine (r) in the transporter. While the oligo-D-arginine transporters were used for the histological experiments to ensure maximal stability of the conjugate and therefore accuracy in determining its location through fluorescence, oligomers of L-arginine were incorporated into the design of the releasable conjugate to minimize its biological half-life. Consistent with its design, the resultant releasable conjugate was shown to be stable at acidic pH, but labile at physiological pH in the absence of serum. This releasable Cyclosporin A conjugate's half-life in pH 7.4 PBS was 90 minutes.

Results

The releasable guanidino-heptamer conjugate of Cyclosporin A was shown to be biologically active by inhibiting IL-2 secretion by the human T cell line, Jurkat, stimulated with PMA and ionomycin in vitro. See R. Wiskocil, et al., *J. Immunol* 134, 1599–603 (1985). The conjugate was added 12 hours prior to the addition of PMA/ionomycin and dose dependent inhibition was observed by the releasable R7 CsA conjugate. This inhibition was not observed with a nonreleasable analog (FIG. 6) that differed from the releasable conjugate by retention of the t-Boc protecting group, which prevented cyclization and resultant release of the active drug. The $EC_{50}$ of the releasable R7 cyclosporin conjugate was approximately two fold higher than CsA dissolved in alcohol and added at the same time as the releasable conjugate.

The releasable R7 CsA conjugate was assayed in viva for functional activity using a murine model of contact dermatitis. Treatment with the 1% releasable R7 CSA conjugate resulted in 73.9%±4.0 reduction in ear inflammation (FIG. 7). No reduction in inflammation was seen in the untreated ear, indicating that the effect seen in the treated ear was local and not systemic. Less inhibition was observed in the ears of mice treated with 0.1 and 0.01% R7-CsA (64.8%±4.0 and 40.9%±3.3 respectively), demonstrating that the effect was titratable. Treatment with the fluorinated corticosteroid positive control resulted in reduction in ear swelling (34.1%±6.3), but significantly less than that observed for 0.1% releasable R7 CsA (FIG. 7). No reduction of inflammation was observed in any of the mice treated with unmodified Cyclosporin A, vehicle alone, R7 (SEQ ID NO:3), or nonreleasable R7 CsA.

Example 9

The Penetration of Copper and Gadolinium-DTPA-r7 Complexes into the Skin of Nude Mice Methods
1. Preparation of Metal Complexes
Step 1-Preparation of Copper-diethylenetriaminepentaacetic Acid Complex (Cu-DTPA)

Figure 8:
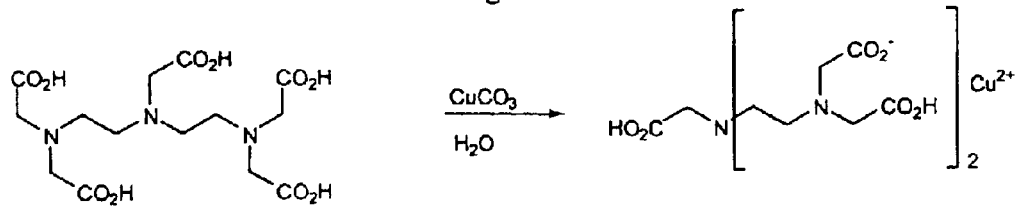
FIG. 8 shows a procedure for the preparation of a copper-diethylenetriaminepentaacetic acid complex (Cu-DTPA).
Figure 9:
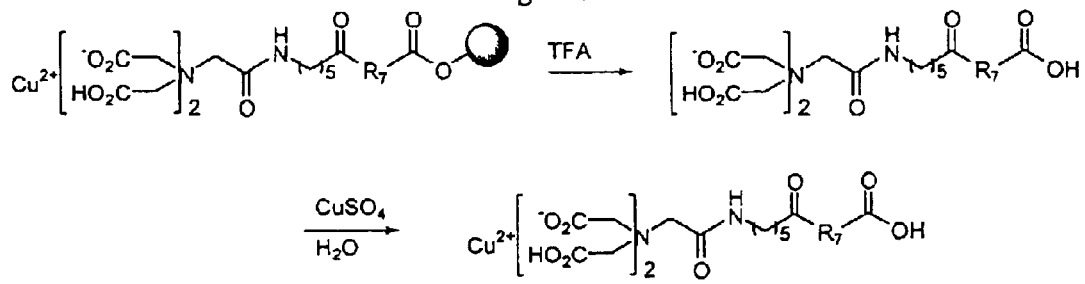
FIG. 9 shows a procedure for linking the Cu-DTPA to a transporter (SEQ ID NOS:33–35) through an aminocaproic acid.

Copper carbonate (10 mmol) and diethylenetriaminpentacetic acid (10 mmol) were dissolved in water (150 mL) (FIG. 8). After 18 h, the solution was centrifuged to removed any solids. The blue solution was decanted and lyophilized to provide a blue powder (yields>90%).
Step 2-Preparation of DTPA Transporter The Cu-DTPA was linked to a transporter through an aminocaproic acid spacer using a PE Applied Biosystems Peptide Synthesizer (ABI 433A) (FIG. 9). The material was cleaved from the resin by treatment with trifluoroacetic acid (TFA) (40 mL), triisopropyl silane (100 μL) and phenol (100 μL) for 18 h. The resin was filtered off and the peptide was precipitated by addition of diethyl ether (80 mL). The solution was centrifliged and the solvent decanted off. The crude solid was purified by reverse-phase HPLC using a water/acetonitrile gradient. Treatment with TFA resulted in loss of $Cu^{2+}$ ion which needed to be reinserted.

DTPA-aca-R7-CO2H (SEQ ID NO:31) (10 mg, 0.0063 mmol) and copper sulfate (1.6 mg, 0.0063 mmol) were dissolved in water (1 mL). Let gently stir for 18 h and lyophilized to provide product as a white powder (10 mg).
2. Analysis of Transport Across Skin Metal diethylenetriaminepentaacetic acid (DTPA) complexes were formed by mixing equimolar amounts of metal salts with DTPA in water for 18 hours. At the end of this time, the solutions were centrifuged, frozen and lyophilized. The dried powder was characterized by mass spectrometry and used in solid phase peptide synthesis. The metal-DTPA complexes were attached to polymers of D- or L-arginine that were still attached to solid-phase resin used in peptide synthesis. The metal-DTPA complexes were attached using an aminocaproic acid spacer. The solid phase peptide synthesis techniques were described in Example 1, with the exception that cleavage of the peptide-DTPA-metal complex in trifluoroacetic acid released the metal. The metal is replaced after HPLC purification and lyophilization of the peptide-DTPA complex. Replacement of the metal involved incubation of equimolar amounts of the metal salt with the peptide-aminocaproic acid-DTPA complex and subsequent lyophilization.

Varying concentrations (1 μM to 1 mM) of the Cu-DTPA-aca-r7 complex were applied to the abdominal region of nude mice for 15, 30 and 45 minutes. As controls, an equimolar amount of the Cu-DTPA complex was spotted onto the abdominal region. At the end of the incubation period, the samples were simply wiped off and intense blue color was apparent on the skin where the Cu-DTPA-aca-r7 complex was spotted and not where the Cu-DTPA alone was spotted. In the case of the application of 1 mM, visible blue dye was seen for three days, decreasing with time, but being apparent for the full period.

Varying concentrations (1 μM to 1 mM) of the Gd-DTPA-aca-r7 complex are injected into the tail vein of BALB/c mice in 100 μl. Distribution of the Gd is observed in real time using magnetic resonance imaging. Distribution of the dye is apparent throughout the bloodstream, entering liver, spleen, kidney, and heart. When injected into the carotid artery of rabbits, the dye is seen to cross the blood brain barrier.

Example 10

Penetration of Hydrocortisone Conjugated to a Biotinylated Pentamer, Heptamer, and Nonamer of D-arginine into the Skin of Nude Mice Methods A. Linking of Hydrocortisone to Delivery-enhancing Transporters Step 1-Acylation of Hydrocortisone with Chloroacetic Anhydride.

A solution of hydrocortisone (200 mg, 0.55 mmol) and chloroacetic anhydride (113 mg, 0.66 mmol) in pyridine (5 mL) was stirred at room temperature for 2 h (FIG. 10). The solvent was evaporated off and the crude product was chromatographed on silica using 50% hexanes/ethyl acetate as the eluent. Product isolated a whites solid (139 mg, 58%).

Step 2-Linking to Transporter

Figure 11:
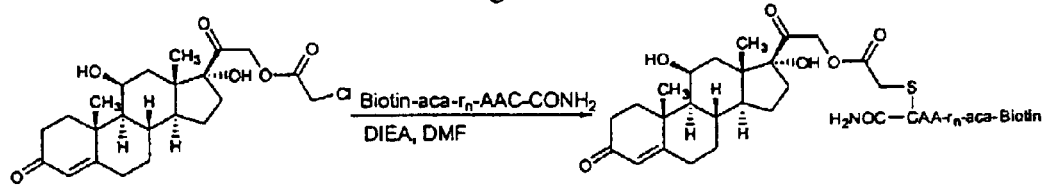
FIG. 11 shows a reaction for linking the acylated hydrocortisone to a transporter.

A solution of the chloroacetic ester of hydrocortisone (0.0137 mmol), a transporter containing a cysteine residue (0.0137) and diisopropylethylamine (DIEA) (0.0274 mmol) in dimethylformamide (DMF) (1 mL) was stirred at room temperature for 18 h (FIG. 11). The material was purified via reverse-phase HPLC using a water/acetonitrile gradient and lyophilized to provide a white powder.

r5 coniugate-12 mg obtained (29% isolated yield)

r7 conjugate-22 mg obtained (55% isolated yield)

R7 conjugate (SEQ ID NO:36)-13 mg obtained (33% isolated yield)

B. Analysis of Transport Across Skin

Varying concentrations (1 mM–100 $\mu$M) of hydrocortisone conjugated to either biotinylated pentamer, heptamer, or nonamers of D-arginine (bio r5, r7, or r9), dissolved in PBS, were applied to the back of nude mice. Samples (100 $\mu$l) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

The conjugates of hydrocortisone with biotinylated heptamers of D-arginine effectively entered into and across the epidermis and into the dermis of the skin of nude mice. In contrast, very little uptake was seen using a conjugate between a pentamer of arginine and hydrocortisone, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 11

Figure 12:
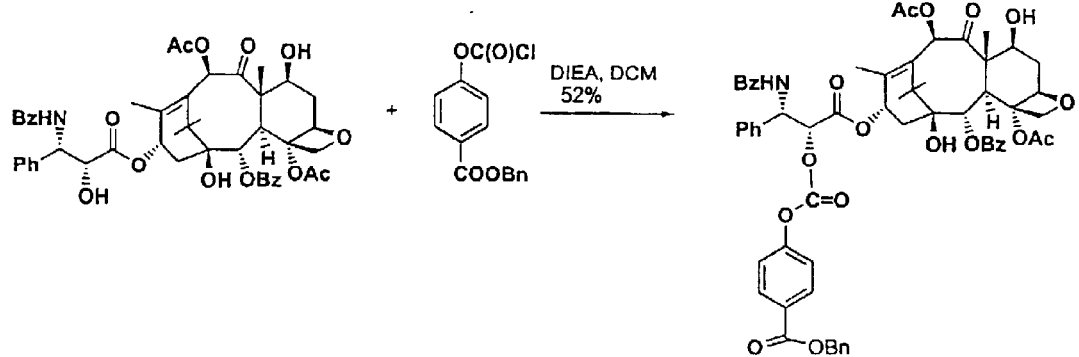
FIG. 12 shows a reaction for preparation of C-2' derivatives of taxol.

Penetration of Taxol Conjugated to a Biotinylated Pentamer, Heptamer, and Nonamer of D-arginine into the Skin of Nude Mice Methods 1. Conjugation of C-2' Activated Taxol Derivatives to Biotin-labeled Peptides Synthesis of C-2' Derivatives Taxol (48.7 mg, 57.1 $\mu$mol) was dissolved in $CH_2Cl_2$ (3.0 mL) under an $N_2$-atmosphere. The solution was cooled to 0° C. A stock solution of the chloroformate of benzyl-(p-hydroxy benzoate) (200 mmol, in 2.0 mL $CH_2Cl_2$—freshly prepared from benzyl-(p-hydroxy benzoate) and diphosgene) was added at 0° C. and stirring at that temperature was continued for 5 hours, after which the solution was warmed to room temperature (FIG. 12). Stirring was continued for additional 10 hours. The solvents were removed in vacuo and the crude material was purified by flash chromatography on silica gel (eluent: EtOAc/hexanes 30%–70%) yielding the desired taxol C-2' carbonate (36.3 mg, 32.8 $\mu$mol, 57.4%).

Coupling to biotin-labeled peptides.

Figure 13:
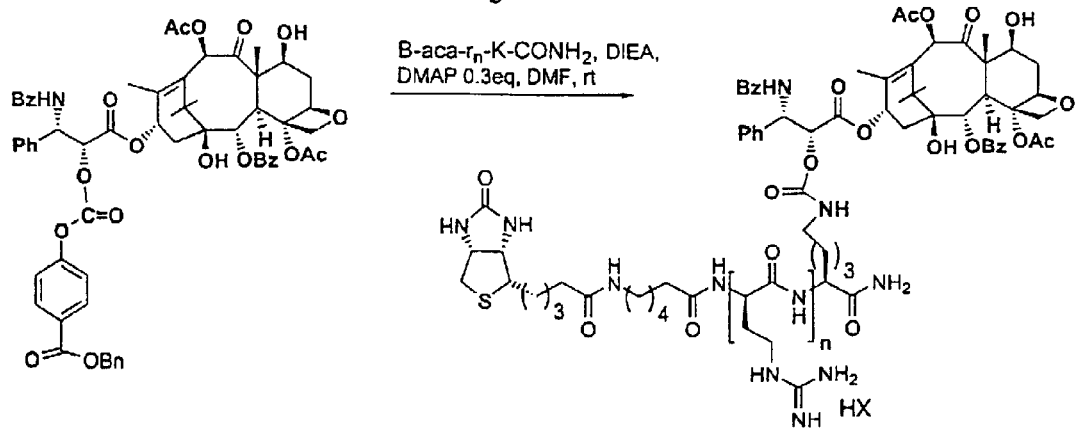
FIG. 13 shows a schematic of a reaction for coupling of a taxol derivative to a biotin-labeled peptide.

A procedure for coupling to biotin-labeled peptides is shown in FIG. 13. The taxol derivative and the biotin labeled peptide (1.2 equivalents) were dissolved in DMF (~10 $\mu$mol/mL DMF) under an $N_2$-atmosphere. Stock solutions of diisopropylethylamine (1.2 equivalents in DMF) and DMAP (0.3 equivalents in DMF) were added and stirring at room temperature was continued until all starting material was consumed. After 16 hours the solvent was removed in vacuo. The crude reaction mixture was dissolved in water and purified by RP-HPLC (eluent: water/MeCN*TFA) yielding the conjugates in the indicated yields:

B-aca-r5-K-taxol: 3.6 mg, 1.32 mmol, 20%.

B-aca-r7-K-taxol: 9.8 mg, 3.01 mmol, 44%.

B-aca-r9-K-taxol: 19.4 mg, 5.1 mmol, 67%.

Figure 14:
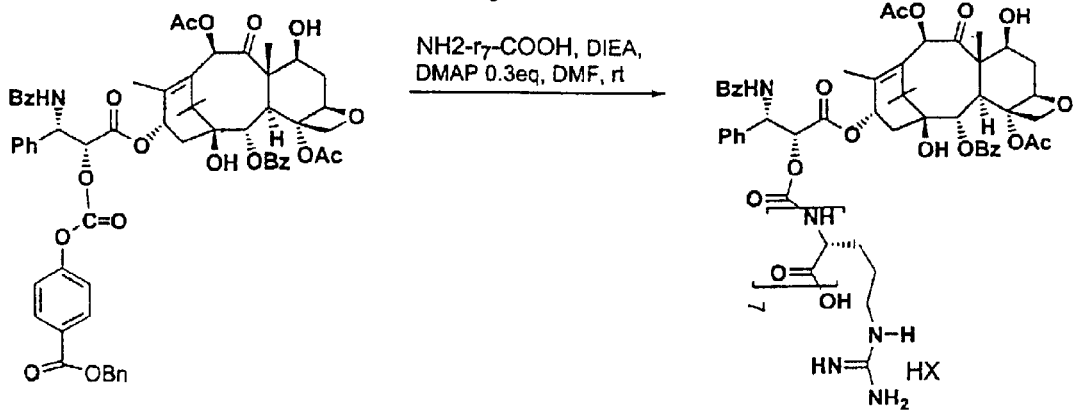
FIG. 14 shows a reaction for coupling of an unlabeled peptide to a C-2' derivative of taxol.

Unlabeled C-2' carbamates:

The taxol derivative (12.4 mg, 11.2 $\mu$mol) and the unlabeled peptide (27.1 mg, 13.4 $\mu$mol) were dissolved in DMF (1.5 mL) under an $N_2$-atmosphere (FIG. 14). Diisopropylethylamine (1.7 mg, 13.4 $\mu$mol) was added as a stock solution in DMF, followed by DMAP (0.68 mg, 5.6 $\mu$mol) as a stock solution in DMF. Stirring at room temperature was continued until all starting material was consumed. After 16 hours the solvent was removed in vacuo. The crude material was dissolved in water and purified by RP-HPLC (eluent: water/MeCN*TFA) yielding the desired product (16.5 mg, 5.9 $\mu$mol, 53%).

Other C-2' Conjugates

Figure 15A:
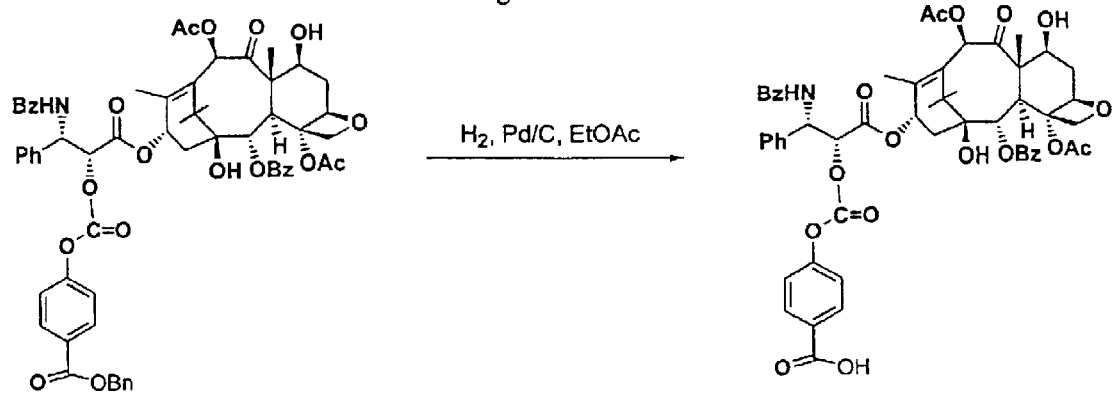
FIGS. 15A–C shows a reaction scheme for the formation of other C-2' taxol-peptide conjugates (SEQ ID NOS:3, 37 and 38).

The taxol derivative (8.7 mg, 7.85 $\mu$mol) was dissolved in EtOAc (2.0 mL). Pd/C (10%, 4.0 mg) was added and the reaction flask was purged with $H_2$ five times (FIG. 15A). Stirring under an atmosphere of hydrogen was continued for 7 hours. The Pd/C was filtered and the solvent was removed in vacuo. The crude material (6.7 mg, 6.58 $\mu$mol, 84%) obtained in this way was pure and was used in the next step without further purification.

Figure 15B:
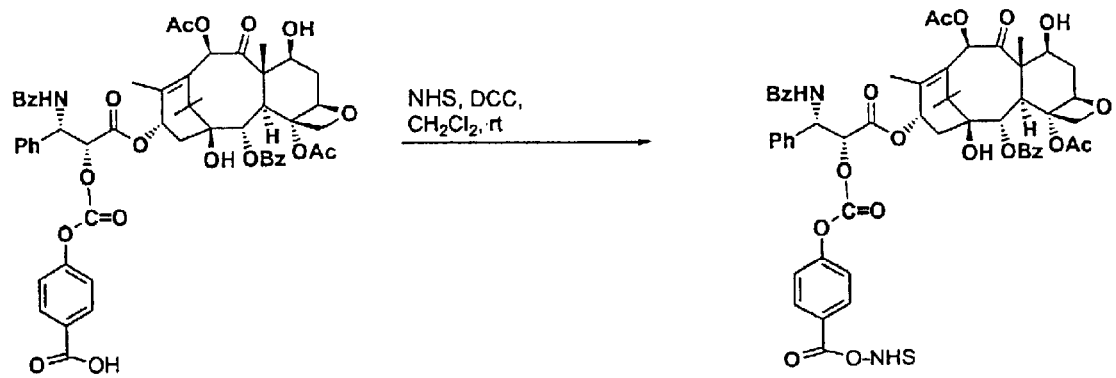

The free acid taxol derivative (18.0 mg, 17.7 $\mu$mol) was dissolved in $CH_2Cl_2$ (2.0 mL). Dicyclohexylcarbodiimide (4.3 mg, 21.3 $\mu$mol) was added as a stock solution in $CH_2Cl_2$ (0.1 mL). N-Hydroxysuccinimide (2.0 mg, 17.7 $\mu$mol) was added as a stock solution in DMF (0.1 mL) (FIG. 15B). Stirring at room temperature was continued for 14 hours. The solvent was removed in vacuo and the resultant crude material was purified by flash chromatography on silica gel (eluent: EtOAc/hexanes 40%–80%) yielding the desired product (13.6 mg, 12.2 $\mu$mol, 69%).

Figure 15C:
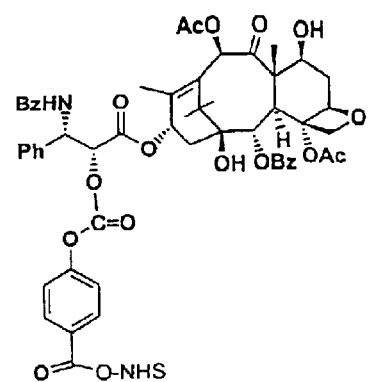
Figure 15C:
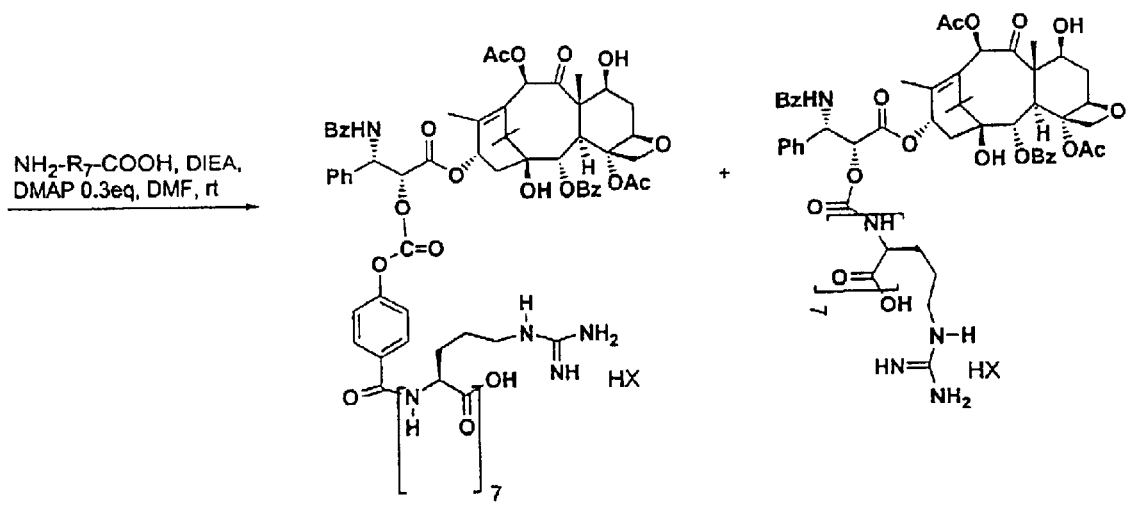

The activated taxol derivative (14.0 mg, 12.6 μmol) and the peptide (30.6 mg, 15.1 μmol) were dissolved in DMF (3.0 mL) under an $N_2$-atmosphere (FIG. 15C). Diisopropylethylamine (1.94 mg, 15.1 μmol) was added as a stock solution in DMF (0.1 mL), followed by DMAP (0.76 mg, 6.3 μmol) as a stock solution in DMF 0.1 mL). Stirring at room temperature was continued until all the starting material was consumed. After 20 hours the solvent was removed in vacuo. The crude material was dissolved in water and purified by RP-HPLC (eluent: water/MeCN*TFA) yielding the two depicted taxol conjugates in a ration of 1:6 (carbonate vs carbamate, respectively).

2. Analysis of Transport Across Skin

Varying concentrations (1 mM–100 μM) of taxol conjugated to either biotinylated pentamer, heptamer, or nonamers of D-arginine (bio r5, r7, or r9), dissolved in PBS, were applied to the back of nude mice. Samples (100 μl) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

The conjugates of taxol with biotinylated heptamers and nonamers of D-arginine effectively entered into and across the epidermis and into the dermis of the skin of nude mice. In contrast, very little uptake was seen using a conjugate between a pentamer of arginine and taxol, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 12

Conjugate of Taxol and Delivery-enhancing Transporter with pH-Releasable Linker

Figure 16:
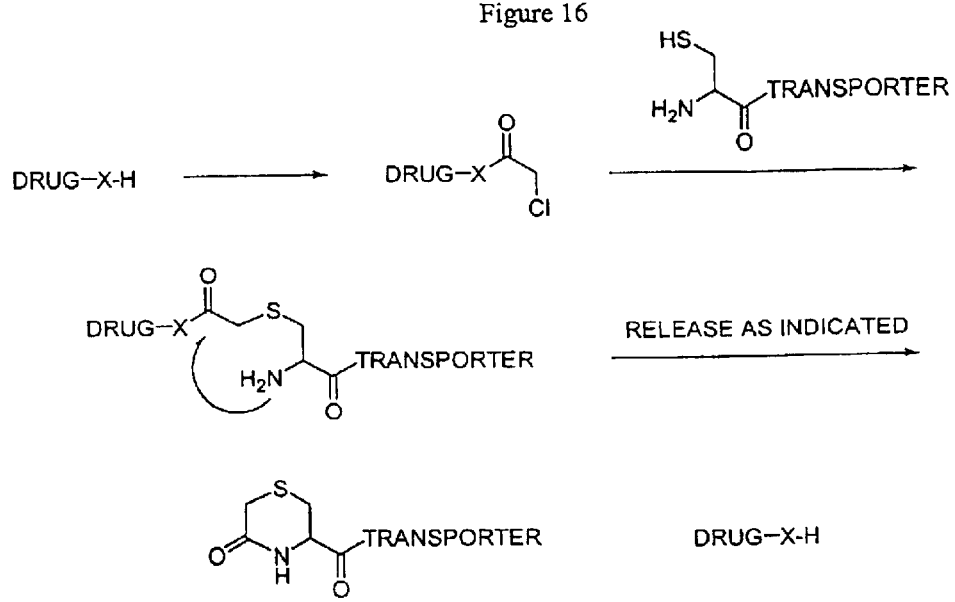
FIG. 16 shows a general strategy for synthesis of a conjugate in which a drug or other biological agent is linked to a delivery-enhancing transporter by a pH-releasable linker.

This Example demonstrates the use of a general strategy for synthesizing prodrugs that have a delivery-enhancing transporter linked to a drug by a linker that releases the drug from the delivery-enhancing transporter upon exposure to physiological pH. In general, a suitable site on the drug is derivatized to carry an α-chloroacetyl residue. Next, the chlorine is displaced with the thiol of a cysteine residue that carries an unprotected amine. This scheme is shown in FIG. 16.

Methods

Synthesis of Taxol-2'-chloroacetyl

Figure 17:
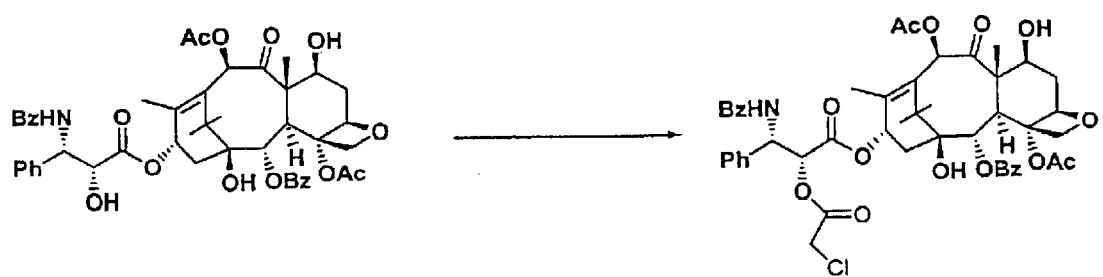
FIG. 17 shows a schematic diagram of a protocol for synthesizing a taxol 2'-chloroacetyl derivative.

Taxol (89.5 mg, 104.9 μmol) was dissolved in $CH_2Cl_2$ (3.5 mL). The solution was cooled to 0° C. under an $N_2$-atmosphere. α-Chloroacetic anhydride (19.7 mg, 115.4 μmol) was added, followed by DIEA (14.8 mg, 115.4 μmol). The solution was allowed to warm to room temperature. After thin layer chromatography (tlc) analysis indicated complete consumption of starting material, the solvent was removed in vacuo and the crude material was purified by flash chromatography on silica gel (eluent: EtOAC/Hex 20%–50%) yielding the desired material (99.8 mg, quantitative) (FIG. 17).

$^1$H-NMR (CDCl$_3$): δ=8.13 (d, J=7.57 Hz, 2H), 7.72 (d, J=7.57 Hz, 2H), 7.62–7.40 (m, 11H), 6.93 (d, J=9.14 Hz, 1H), 6.29–6.23 (m, 2H), 6.01 (d, J=7.14 Hz, 1H), 5.66 (d, J=6.80 Hz, 1H), 5.55 (d, J=2.24 Hz, 1H), 4.96 (d, J=8.79 Hz, 1H), 4.43 (m, 1H), 4.30 (d, J=8.29 Hz, 1H), 4.20–4.15 (m, 2H), 3.81 (d, J=6.71 Hz, 1H), 2.56–2.34 (m, 3H), 2.45 (s, 3H), 2.21 (s, 3H), 2.19 (m, 1H), 1.95–1.82 (m, 3H), 1.92 s, (3H), 1.67 (s, 3H), 1.22 (s, 3H), 1.13 (s, 3H) ppm.

$^{13}$C-NMR (CDCl$_3$): δ=203.6, 171.1, 169.7, 167.3, 167.0, 166.9, 166.3, 142.3, 136.4, 133.6, 133.5, 132.9, 132.0, 130.1, 129.2, 121.1, 128.7, 128.6, 127.0, 126.5, 84.3, 81.0, 79.0, 76.3, 75.4, 75.2, 75.0, 72.2, 72.0, 58.4, 52.7, 45.5, 43.1, 40.1, 35.5, 26.7, 22.6, 22.0, 20.7, 14.7, 9.5 ppm.

Linkage of Taxol to Delivery-Enhancing Transporter

Figure 18:
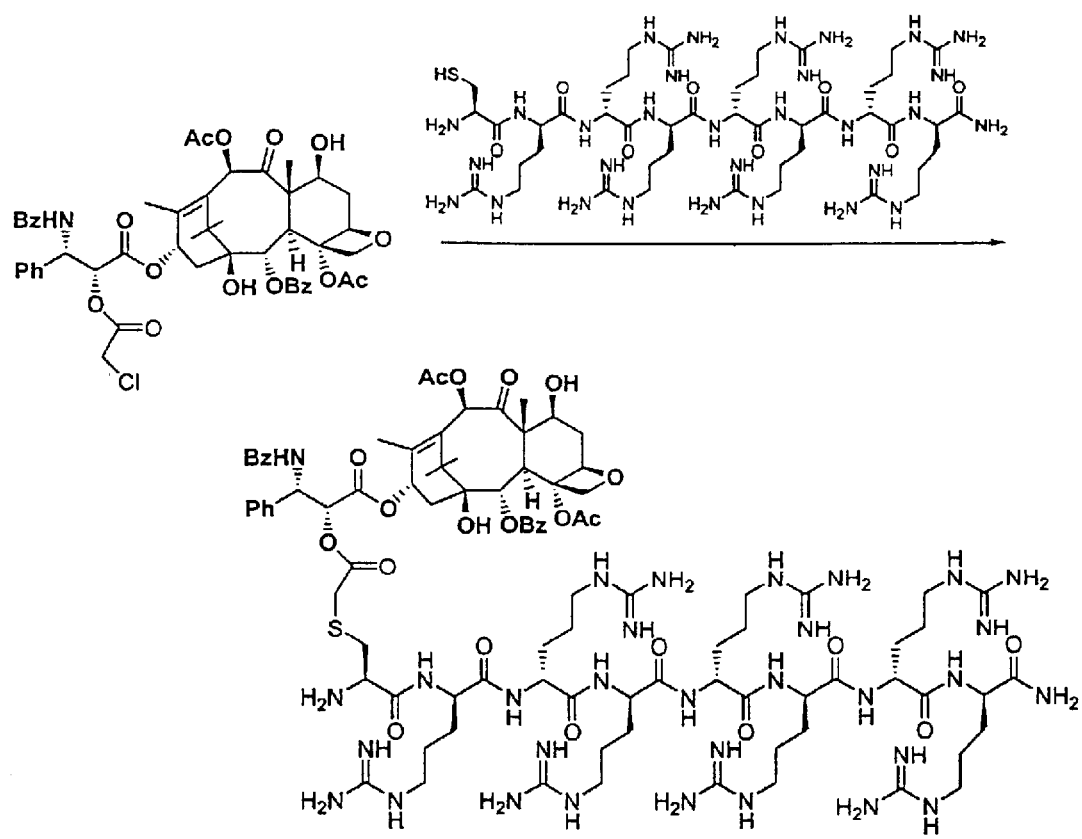
FIG. 18 shows a strategy by which a taxol 2'-chloroacetyl derivative is linked to an arginine heptamer delivery-enhancing transporter.

The peptide (47.6 mg, 22.4 μmol) was dissolved in DMF (1.0 mL) under an $N_2$-atmosphere. DIEA (2.8 mg, 22.4 μmol) was added. A solution of taxol-2'-chloroacetate (20.8 mg, 22.4 μmol) in DMF (1.0 mL) was added. Stirring at room temperature was continued for 6 hours. Water containing 0.1% TFA (1.0 mL) was added, the sample was frozen and the solvents were lyophilized. The crude material was purified by RP-HPLC (eluent: water/MeCN*0.1% TFA: 85%–15%). A schematic of this reaction is shown in FIG. 18.

Synthesis of Related Conjugates

Using the conjugation conditions outlined above, the three additional conjugates shown in were synthesized.

Cytotoxicity Assay

Figure 19:
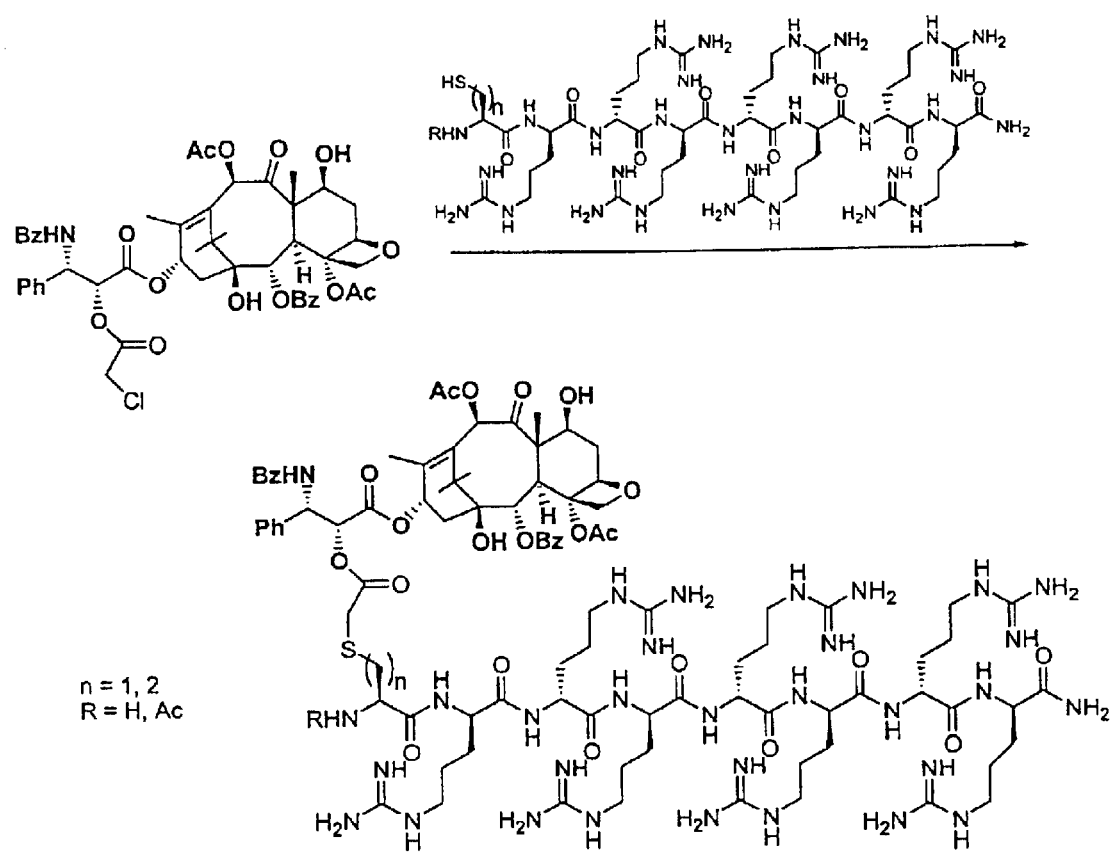
FIG. 19 shows three additional taxol-r7 conjugates that can be made using the reaction conditions illustrated in FIG. 18.
Figure 20:
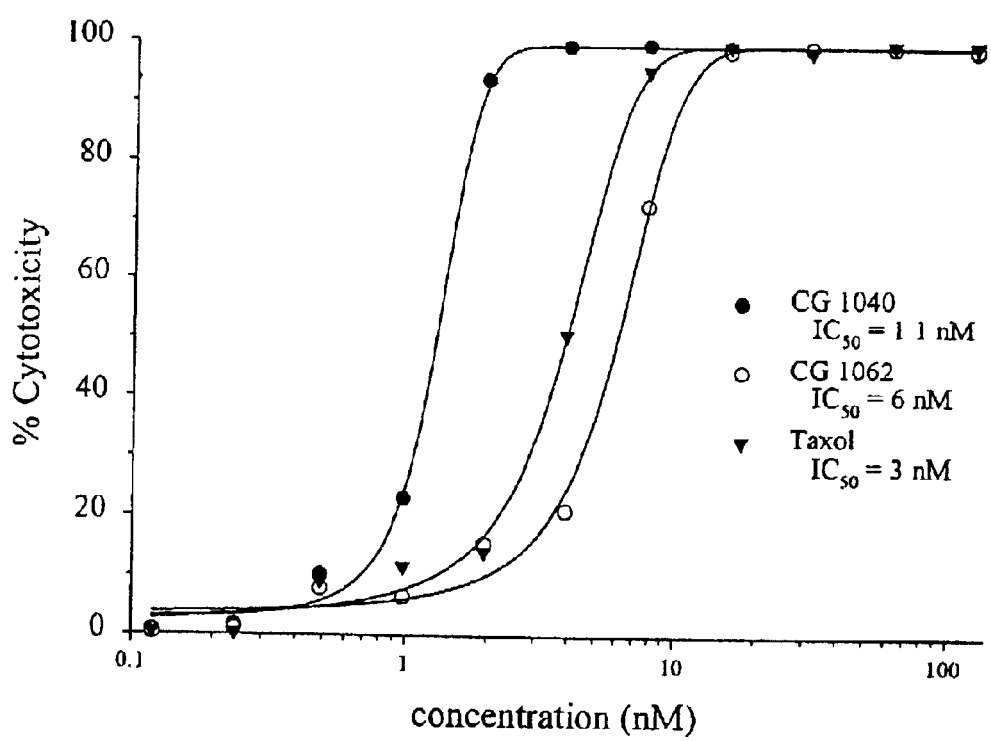
FIG. 20 shows the results of a 3 day MTT cytotoxicity assay using taxol and two different linkers.
Figure 21:
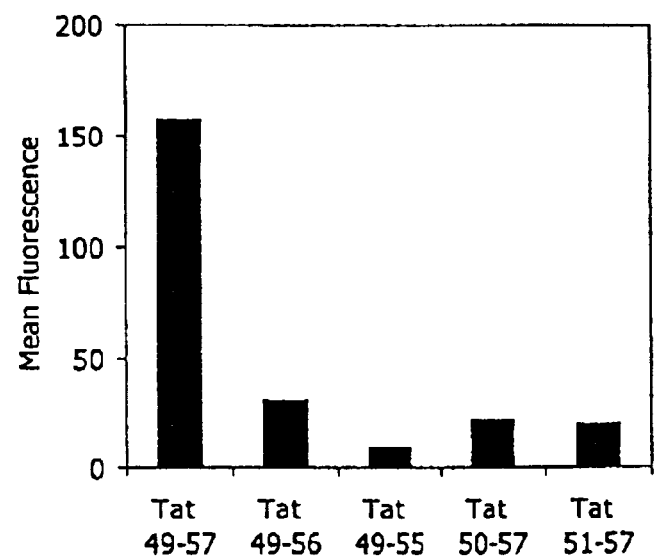
FIG. 21: FACS cellular uptake assay of truncated analogs of $Tat_{49-57}$(F1-ahx-RKKRRQRRR; SEQ ID NO:8): $Tat_{49-56}$ (F1-ahx-RKKRRQRR; SEQ ID NO:9), $Tat_{49-55}$ (F1-ahx-RKKRRQR; SEQ ID NO:10), $Tat_{50-57}$ (F1-ahx-KKRRQRRR; SEQ ID NO:11), and $Tat_{51-57}$ (F1-ahx-KRRQRRR; SEQ ID NO:12). Jurkat cells were incubated with varying concentrations (12.5 μM shown) of peptides for 15 mm at 23° C.

The taxol conjugates were tested for cytotoxicity in a 3-(4,5-dimethylthiazol-2-yl)-2,5-diphenyl-tetrazolium-bromide (MTT) dye reduction. Results, which are shown in FIG. 20, demonstrate that the taxol conjugated to r7 with a readily pH-releasable linker (CG 1062; R=Ac in the structure shown in FIG. 19) is significantly more cytotoxic than either taxol alone or taxol conjugated to r7 with a less-readily pH-releasable linker (CG 1040; R=H in the structure shown in FIG. 19).

Example 13

Structure-Function Relationships of Fluorescently-Labeled Peptides Derived from Tat$_{49-57}$ Methods General. Rink amide resin and Boc$_2$O were purchased from Novabiochem. Diisopropylcarbodiimide, bromoacetic acid, fluorescein isothiocyanate (FITC-NCS), ethylenediamine, 1,3-diaminopropane, 1,4-diaminobutane, 1,6-diaminohexane, trans-1,6-diaminocyclohexane, and pyrazole-1-carboxamidine were all purchased from Aldrich®. All solvents and other reagents were purchased from commercial sources and used without further purification. The mono-Boc amines were synthesized from the commercially available diamines using a literature procedure (10 equiv. of diamine and 1 equiv. of Boc$_2$O in chloroform followed by an aqueous work up to remove unreacted diamine) (34).

N-tert-butoxycarbonyl-1,6-trans-diaminocyclohexane. Mp 159–161° C.; $^1$H NMR (CDCl$_3$) δ4.35 (br s, 1H), 3.37 (br s, 1H), 2.61 (br s, 1H), 1.92–2.02 (m, 2H), 1.81–1.89 (m, 2H), 1.43 (s, 9H), 1.07–1.24 (m, 4H) ppm; $^{13}$C NMR (D$_6$-DMSO) δ154.9, 77.3, 49.7, 48.9, 35.1, 31.4, 28.3 ppm; ES-MS (M+1) calcd 215.17, found 215.22.

General Procedure for Peptide Synthesis. Tat$_{49-57}$ (RKKRRQRRR; SEQ ID NO:28), truncated and alanine-substituted peptides derived from Tat$_{49-57}$, Antennapedia$_{43-58}$ (RQIKIWFQNRRMKWKK;SEQ ID NO:29), and homopolymers of arginine (R5–R9; SEQ ID NOS:1–5) and d-arginine (r5–r9) were prepared with an automated peptide synthesizer (ABI433) using standard solid-phase Fmoc chemistry (35) with HATU as the peptide coupling reagent. The fluorescein moiety was attached via a aminohexanoic acid spacer by treating a resin-bound peptide (1.0 mmol) with fluorescein isothiocyanate (1.0 mmol) and DIEA (5 mmol) in DMF (10 mL) for 12 h. Cleavage from the resin was achieved using 95:5 TFA/triisopropylsilane. Removal of the solvent in vacuo gave a crude oil which was triturated with cold ether. The crude mixture thus obtained was centrifuged, the ether was removed by decantation, and the resulting orange solid was purified by reverse-phase HPLC ($H_2O/CH_3CN$ in 0.1% TFA). The products were isolated by lyophilization and characterized by electrospray mass spectrometry. Purity of the peptides was >95% as determined by analytical reverse-phase HPLC ($H_2O/CH_3CN$ in 0.1% TFA).

All peptides and peptoids synthesized contain an aminohexanoic (ahx) acid moiety attached to the N-terminal amino group with a fluorescein moiety (Fl) covalently linked to the amino group of the aminohexanoic acid spacer. The carboxyl terminus of every peptide and peptoid is a carboxamide.

Cellular Uptake Assay. The arginine homopolymers and guanidine-substituted peptoids were each dissolved in PBS buffer (pH 7.2) and their concentration was determined by absorption of fluorescein at 490 nm ($\epsilon$–67,000). The accuracy of this method for determining concentration was established by weighing selected samples and dissolving them in a known amount of PBS buffer. The concentrations determined by UV spectroscopy correlated with the amounts weighed out manually. Jurkat cells (human T cell line), murine B cells (CH27), or human PBL cells were grown in 10% fetal calf serum and DMEM and each of these were used for cellular uptake experiments. Varying amounts of arginine and oligomers of guanidine-substituted peptoids were added to approximately $3 \times 10^6$ cells in 2% FCS/PBS (combined total of 200 $\mu$L) and placed into microtiter plates (96 well) and incubated for varying amounts of time at 23° C. or 4° C. The microtiter plates were centrifuged and the cells were isolated, washed with cold PBS ($3 \times 250$ $\mu$L), incubated with 0.05% trypsin/0.53 mM EDTA at 37° C. for 5 min, washed with cold PBS, and resuspended in PBS containing 0.1% propidium iodide. The cells were analyzed using fluorescent flow cytometry (FACScan, Becton Dickinson) and cells staining with propidium iodide were excluded from the analysis. The data presented is the mean fluorescent signal for the 5000 cells collected.

Inhibition of Cellular Uptake with Sodium Azide. The assays were performed as previously described with the exception that the cells used were preincubated for 30 min with 0.5% sodium azide in 2% FCS/PBS buffer prior to the addition of fluorescent peptides and the cells were washed with 0.5% sodium azide in PBS buffer. All of the cellular uptake assays were run in parallel in the presence and absence of sodium azide.

Cellular Uptake Kinetics Assay. The assays were performed as previously described except the cells were incubated for 0.5, 1, 2, and 4 min at 4° C. in triplicate in 2% FCS/PBS (50 $\mu$l) in microtiter plates (96 well). The reactions were quenched by diluting the samples into 2% FCS/PBS (5 mL). The assays were then worked up and analyzed by fluorescent flow cytometry as previously described.

Results

To determine the structural requirements for the cellular uptake of short arginine-rich peptides, a series of fluorescently-labeled truncated analogues of $Tat_{49-57}$ were synthesized using standard solid-phase chemistry. See, e.g., Atherton, E. et al. SOLID-PHASE PEPTIDE SYNTHESIS (IRL: Ixford, Engl. 1989). A fluorescein moiety was attached via an aminohexanoic acid spacer on the amino termini. The ability of these fluorescently labeled peptides to enter Jurkat cells was then analyzed using fluorescent activated cell sorting (FACS). The peptide constructs tested were $Tat_{49-57}$ (Fl-ahx-RKKRRQRRR; SEQ ID NO:8): $Tat_{49-56}$ (Fl-ahx-RKKRRQRR; SEQ ID NO:9), $Tat_{49-55}$ (Fl-ahx-RKKRRQR; SEQ ID NO:10), $Tat_{50-57}$ (Fl-ahx-KKRRQRRR; SEQ ID NO:11), and $Tat_{51-57}$ (Fl-ahx-KRRQRRR; SEQ ID NO:12). Differentiation between cell surface binding and internalization was accomplished throughout by running a parallel set of assays in the presence and absence of sodium azide. Because sodium azide inhibits energy-dependent cellular uptake but not cell surface binding, the difference in fluorescence between the two assays provided the amount of fluorescence resulting from internalization.

Deletion of one arginine residue from either the amine terminus ($Tat_{50-57}$) or the carboxyl terminus ($Tat_{49-56}$) resulted in an 80% loss of intracellular fluorescence compared to the parent sequence ($Tat_{49-57}$). From the one amino acid truncated analogs, further deletion of R-56 from the carboxyl terminus ($Tat_{49-55}$) resulted in an additional 60% loss of intracellular fluorescence, while deletion of K-50 from the amine terminus ($Tat_{51-57}$) did not further diminish the amount of internalization. These results indicate that truncated analogs of $Tat_{49-57}$ are significantly less effective at the transcellular delivery of fluorescein into Jurkat cells, and that the arginine residues appear to contribute more to cellular uptake than the lysine residues.

Figure 22:
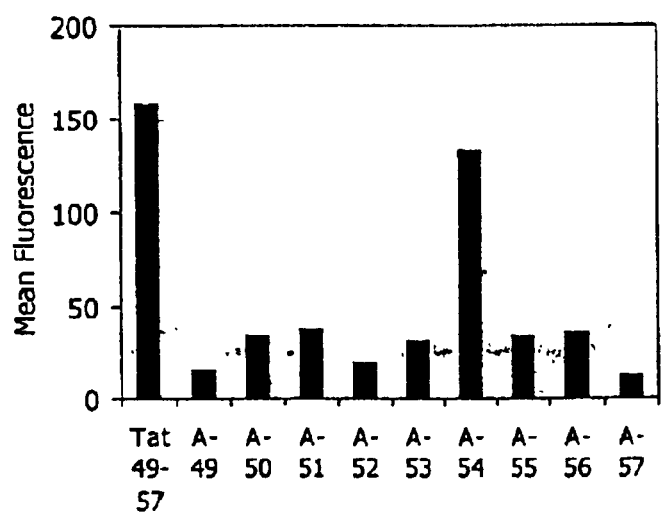
FIG. 22 shows FACS cellular uptake assay of alanine-substituted analogs of $Tat_{49-57}$(F1-ahx-AKKRRQRRR; SEQ ID NO:13), A-50 (F1-ahx-RAKRRQRRR; SEQ ID NO:14), A-51 (F1-ahx-RKARRQRRR; SEQ ID NO:15), A-52 (F1-ahx-RKKARQRRR; SEQ ID NO:16), A-53 (F1-ahx-RXKRAQRRR; SEQ ID NO:17), A-54 (F1-ahx-RT (KPRARRR; SEQ ID NO:18), A-55 (F1-ahx-RKKRRQARR; SEQ ID NO:19), A-56 (F1-ahx-RKKRRQRAR; SEQ ID NO:20), and A-57 (F1-ahx-RKKRRQRRA; SEQ ID NO:21). Jurkat cells were incubated with varying concentrations (12.5 μM shown) of peptides for 12 min at 23° C.

To determine the contribution of individual amino acid residues to cellular uptake, analogs containing alanine substitutions at each site of $Tat_{49-57}$ were synthesized and assayed by FACS analysis (FIG. 22). The following constructs were tested: A-49 (Fl-ahx-AKKRRQRRR; SEQ ID NO:13), A-50 (Fl-ahx-RAKRRQRRR; SEQ ID NO:14), A-51 (Fl-ahx-RKARRQRRR; SEQ ID NO:15), A-52 (Fl-ahx-RKKARQRRR; SEQ ID NO:16), A-53 (Fl-ahx-RKKRAQRRR; SEQ ID NO:17), A-54 (Fl-ahx-RKKRRARRR; SEQ ID NO:18), A-55 (Fl-ahx-RKKRRQARR; SEQ ID NO:19), A-56 (Fl-ahx-RKKRRQRAR; SEQ ID NO:20), and A-57 (Fl-ahx-RKKRRQRRA; SEQ ID NO:21). Substitution of the noncharged glutamine residue of $Tat_{49-57}$ with alanine (A-54) resulted in a modest decrease in cellular internalization. On the other hand, alanine substitution of each of the cationic residues individually produced a 70–90% loss of cellular uptake. In these cases, the replacement of lysine (A-50, A-51) or arginine (A-49, A-52, A-55, A-56, A-57) with alanine had similar effects in reducing uptake.

Figure 23:
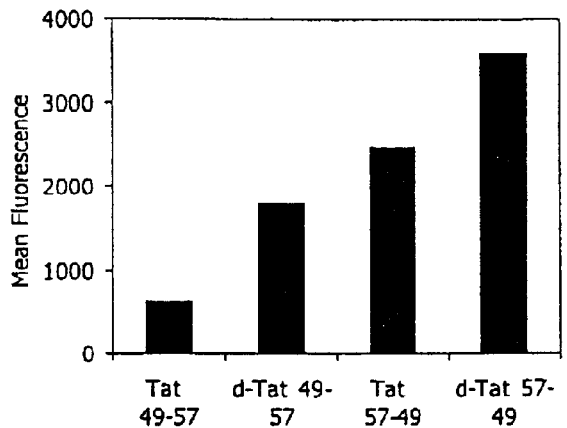
FIG. 23: FACS cellular uptake assay of d- and retro-isomers of $Tat_{49-57}$: d-$Tat_{49-57}$ (F1-ahx-rkkrrqrrr), $Tat_{57-49}$ (F1-ahx-RRRQRRKKR; SEQ ID NO:22), and d-$Tat_{57-49}$ (F1-ahx-rrrqrrkkr). Jurkat cells were incubated with varying concentrations (12.5 μM shown) of peptides for 15 min at 23° C.

To determine whether the chirality of the transporter peptide was important, the corresponding d-(d-$Tat_{49-57}$), retro-l-($Tat_{57-49}$), and retro-inverso isomers (d-$Tat_{57-49}$) were synthesized and assayed by FACS analysis (FIG. 23). Importantly, all three analogs were more effective at entering Jurkat cells then $Tat_{49-57}$. These results indicated that the chirality of the peptide backbone is not crucial for cellular uptake. Interestingly, the retro-l isomer ($Tats_{57-49}$) which has three arginine residues located at the amine terminus instead of one arginine and two lysines found in $Tat_{49-57}$ demonstrated enhanced cellular uptake. Thus, residues at the amine terminus appear to be important and that arginines are more effective than lysines for internalization. The improved cellular uptake of the unnatural d-peptides is most likely due to their increased stability to proteolysis in 2% FCS (fetal calf serum) used in the assays. When serum was excluded, the d- and l-peptides were equivalent as expected.

These initial results indicated that arginine content is primarily responsible for the cellular uptake of $Tat_{49-57}$.

Figure 24:
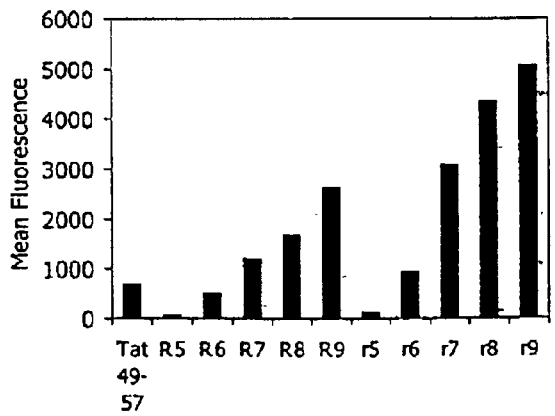
FIG. 24: FACS cellular uptake of a series of arginine oligomers and $Tat_{49-57}$: R5 (F1-ahx-RRRRR; SEQ ID NO:23), R6 (F1-ahx-RRRRRR; SEQ ID NO:24), R7 (F1-ahx-RRRRRRR; SEQ ID NO:25), R8 (F1-ahx-RRRRRRRR; SEQ ID NO:26), R9 (F1-ahx-RRRRRRRRR; SEQ ID NO:27), r5 (F1-ahx-rrrrr), r6 (F1-ahx-rrrrrr), r7 (F1-ahx-rrrrrrr), r8 (F1-ahx-rrrrrrrr), r9 (F1-ahx-rrrrrrrrr). Jurkat cells were incubated with varying concentrations (12.5 μM shown) of peptides for 4 min at 23° C.

Furthermore, these results were consistent with our previous results where we demonstrated that short oligomers of arginine were more effective at entering cells then the corresponding short oligomers of lysine, ornithine, and histidine. What had not been established was whether arginine homo-oligomers are more effective than $Tat_{49-57}$. To address this point, $Tat_{49-57}$ was compared to the l-arginine (R5–R9; SEQ ID NOS:1–5) and d-arginine (r5–r9) oligomers. Although $Tat_{49-57}$ contains eight cationic residues, its cellular internalization was between that of R6 (SEQ ID NO:2) and R7 (SEQ ID NO:3) (FIG. 24) demonstrating that the presence of six arginine residues is the most important factor for cellular uptake. Significantly, conjugates containing 7–9 arginine residues exhibited better uptake than $Tat_{49-57}$.

To quantitatively compare the ability of these arginine oligomers and $Tat_{49-57}$ to enter cells, Michaelis-Menton kinetic analyses were performed. The rates of cellular uptake were determined after incubation (3° C.) of the peptides in Jurkat cells for 30, 60, 120, and 240 seconds (Table 1). The resultant $K_m$ values revealed that r9 and R9 (SEQ ID NO:5) entered cells at rates approximately 100-fold and 20-fold faster than $Tat_{47-59}$ respectively. For comparison, $Antennapedia_{43-58}$ was also analyzed and was shown to enter cells approximately 2-fold faster than $Tat_{47-59}$, but significantly slower than r9 or R9 (SEQ ID NO:5).

TABLE 1

Michaelis-Menton kinetics: $Antennapedia_{43-58}$
(Fl-ahx-RQIKIWFQNRRMKWKK);SEQ ID NO:30).
R9 = SEQ ID NO:5.

| peptide | $K_m(\mu M)$ | $V_{max}$ |
|---|---|---|
| $Tat_{49-57}$ | 770 | 0.38 |
| $Antennapedia_{43-58}$ | 427 | 0.41 |
| R9 | 44 | 0.37 |
| r9 | 7.6 | 0.38 |

Example 14

Design and Synthesis of Peptidomimetic Analogs of $Tat_{49-57}$

Methods

General Procedure for Peptoid Polyamine Synthesis. Peptoids were synthesized manually using a fritted glass apparatus and positive nitrogen pressure for mixing the resin following the literature procedure developed by Zuckermann. See, e.g., Murphy, J. E. et al., *Proc. Natl. Acad. Sci. USA* 95, 1517–1522 (1998); Simon, R. J. et al., *Proc. Natl. Acad. Sci. USA* 89, 9367–9371 (1992); Zuckermann, R. N. et al., *J. Am. Chem. Soc.* 114, 10646–10647 (1992). Treatment of Fmoc-substituted Rink amide resin (0.2 mmol) with 20% piperidine/DMF (5 mL) for 30 min (2×) gave the free resin-bound amine which was washed with DMF (3×5 mL). The resin was treated with a solution of bromoacetic acid (2.0 mmol) in DMF (5 mL) for 30 min. This procedure was repeated. The resin was then washed (3×5 mL DMF) and treated with a solution of mono-Boc diamine (8.0 mmol) in DMF (5 mL) for 12 hrs. These two steps were repeated until an oligomer of the required length was obtained (Note: the solution of mono-Boc diamine in DMF could be recycled without appreciable loss of yield). The resin was then treated with N-Fmoc-aminohexanoic acid (2.0 mmol) and DIC (2.0 mmol) in DMF for 1 h and this was repeated. The Fmoc was then removed by treatment with 20% piperidine/DMF (5 mL) for 30 min. This step was repeated and the resin was washed with DMF (3×5 mL). The free amine resin was then treated with fluorescein isothiocyanate (0.2 mmol) and DIEA (2.0 mmol) in DMF (5 mL) for 12 hrs. The resin was then washed with DMF (3×5 mL) and dichloromethane (5×5 mL). Cleavage from the resin was achieved using 95:5 TFA/triisopropylsilane (8 mL). Removal of the solvent in vacuo gave a crude oil which was triturated with cold ether (20 mL). The crude mixture thus obtained was centrifuged, the ether was removed by decantation, and the resulting orange solid was purified by reverse-phase HPLC ($H_2O$/$CH_3CN$ in 0.1% TFA). The products were isolated by lyophilization and characterized by electrospray mass spectrometry and in selected cases by $^1H$ NMR spectroscopy.

General Procedure for Perguanidinylation of Peptoid Polyamines. A solution of peptoid amine (0.1 mmol) dissolved in deionized water (5 mL) was treated with sodium carbonate (5 equivalents per amine residue) and pyrazole-1-carboxamidine (5 equivalents per amine residue) and heated to 50° C. for 24–48 hr. The crude mixture was then acidified with TFA (0.5 mL) and directly purified by reverse-phase HPLC ($H_2O$/$CH_3CN$ in 0.1% TFA). The products were characterized by electrospray mass spectrometry and isolated by lyophilization and further purified by reverse-phase HPLC. The purity of the guanidine-substituted peptoids was >95% as determined by analytical reverse-phase HPLC ($H_2O$/$CH_3CN$ in 0.1% TFA).

Results

Utilizing the structure-function relationships that had been determined for the cellular uptake of $Tat_{47-59}$, we designed a set of polyguanidine peptoid derivatives that preserve the 1,4 backbone spacing of sidechains of arginine oligomers, but have an oligo-glycine backbone devoid of stereogenic centers. These peptoids incorporating arginine-like side chains on the amide nitrogen were selected because of their expected resistance to proteolysis, and potential ease and significantly lower cost of synthesis (Simon et al., *Proc. Natl. Acad. Sci. USA* 89:9367–9371 (1992); Zuckermann, et al., *J. Am. Chem. Soc.* 114:10646–10647 (1992). Furthermore, racemization, frequently encountered in peptide synthesis, is not a problem in peptoid synthesis; and the "sub-monomer" peptoid approach allows for facile modification of side-chain spacers. Although the preparation of an oligurea and peptoid-peptide hybrid (Hamy, et al, *Proc. Natl. Acad. Sci. USA* 94:3548–3553 (1997)) derivatives of $Tat_{49-57}$ have been previously reported, their cellular uptake was not explicitly studied.

Figure 25:
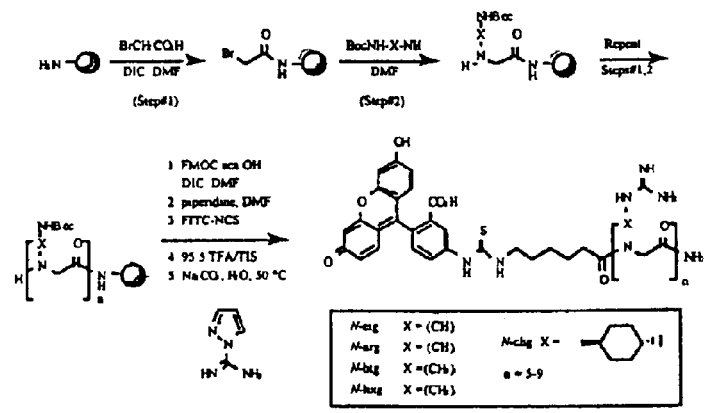
FIG. 25: Preparation of guanidine-substituted peptoids (SEQ ID NOS:39–43).

The desired peptoids were prepared using the "sub-monomer" approach (Simon et al.; Zuckermann et al.) to peptoids followed by attachment of a fluorescein moiety via an aminohexanoic acid spacer onto the amine termini. After cleavage from the solid-phase resin, the fluorescently labeled polyamine peptoids thus obtained were converted in good yields (60–70%) into polyguanidine peptoids by treatment with excess pyrazole-1-carboxamidine (Bematowicz, et al., *J. Org. Chem.* 57:2497–2502 (1992) and sodium carbonate (as shown in FIG. 25). Previously reported syntheses of peptoids containing isolated N-Arg units have relied on the synthesis of N-Arg monomers (5–7 steps) prior to peptoid synthesis and the use of specialized and expensive guanidine protecting groups (Pmc, Pbf) (Kruijtzer, et al., *Chem. Eur. J.* 4:1570–1580 (1998); Heizmann, et al. *Peptide Res.* 7:328–332 (1994). The compounds reported here represent the first examples of polyguanidinylated peptoids prepared using a perguanidinylation step. This method provides easy access to polyguanidinylated compounds from the corresponding polyamines and is especially useful for the synthesis of perguanidinylated homooligomers.

Furthermore, it eliminates the use of expensive protecting groups (Pbf, Pmc). An additional example of a perguanidinylation of a peptide substrate using a novel triflyl-substituted guanylating agent has recently been reported (Feichtinger, et al., *J. Org. Chem.* 63:8432–8439 (1998)).

Figure 26:
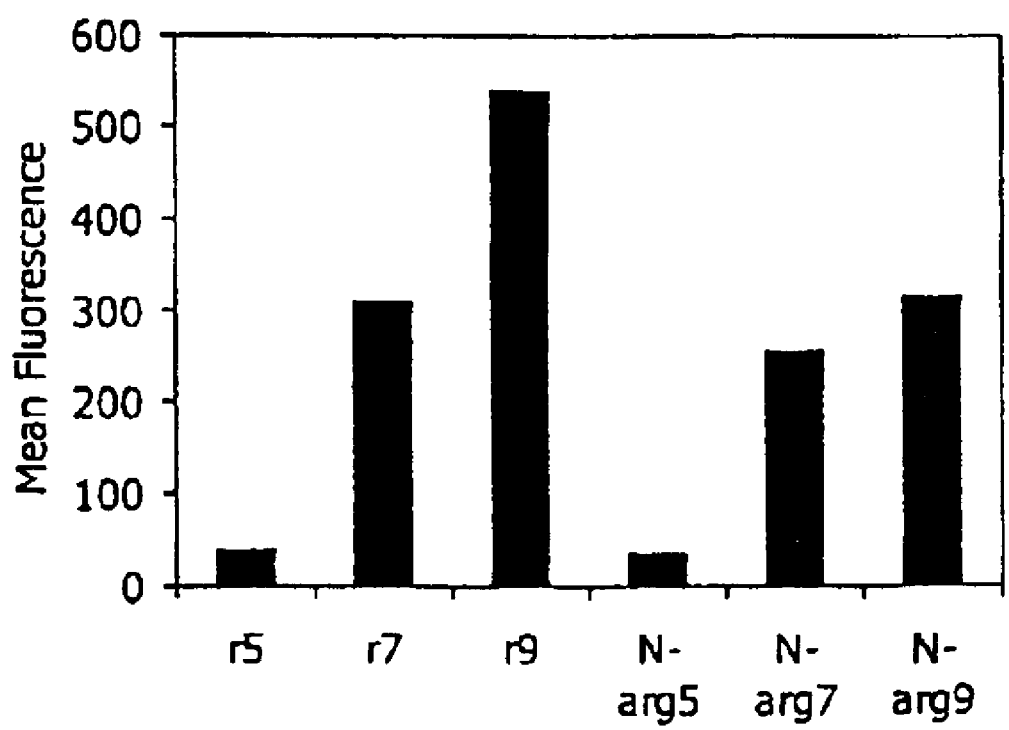
FIG. 26: FACS cellular uptake of polyguanidine peptoids (SEQ ID NOS:39, 41 and 43) and d-arginine oligomers. Jurkat cells were incubated with varying concentrations (12.5 μM shown) of peptoids and peptides for 4 min at 23° C.

The cellular uptake of fluorescently labeled polyguanidine N-arg5,7,9 (SEQ ID NOS:39, 41 and 43) peptoids was compared to the corresponding d-arginine peptides r5,7,9 (similar proteolytic properties) using Jurkat cells and FACS analysis. The amount of fluorescence measured inside the cells with N-arg5,7,9 (SEQ ID NOS:39, 41 and 43) was proportional to the number of guanidine residues: N-arg9 > N-arg7>N-arg5 (SEQ ID NOS:39, 41 and 43) (FIG. 26), analogous to that found for r5,7,9. Furthermore, the N-arg5, 7,9 (SEQ ID NOS:39, 41 and 43) peptoids showed only a slightly lower amount of cellular entry compared to the corresponding peptides, r5,7,9. The results demonstrate that the hydrogen bonding along the peptide backbone of $Tat_{49-57}$ or arginine oligomers is not a required structural element for cellular uptake and oligomeric guanidine-substituted peptoids can be utilized in place of arginine-rich peptides as molecular transporters. The addition of sodium azide inhibited internalization demonstrating that the cellular uptake of peptoids was also energy dependent.

Example 15

The Effect of Side Chain Length on Cellular Uptake

Figure 27:
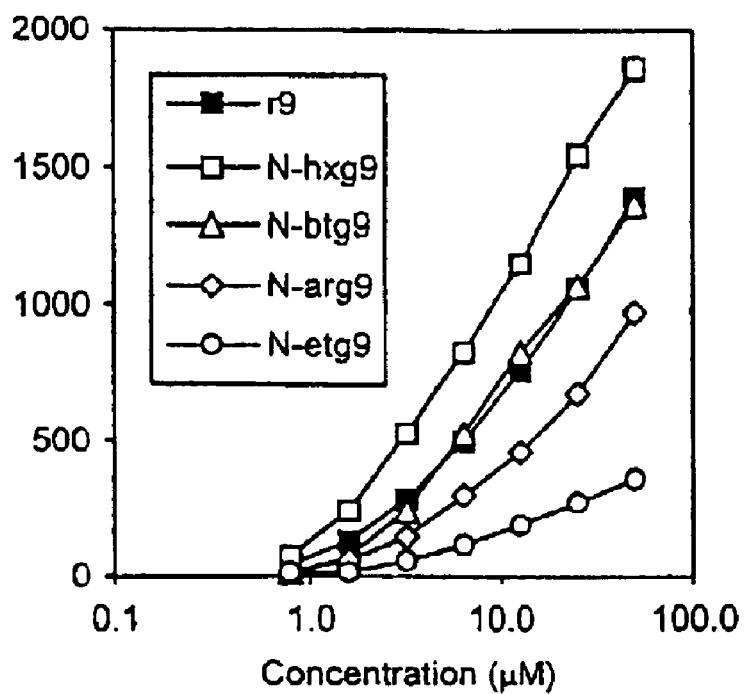
FIG. 27: FACS cellular uptake of d-arginine oligomers and polyguanidine peptoids. Jurkat cells were incubated with varying concentrations (12.5 μM shown) of fluorescently labeled peptoids and peptides for 4 min at 23° C.
Figure 28:
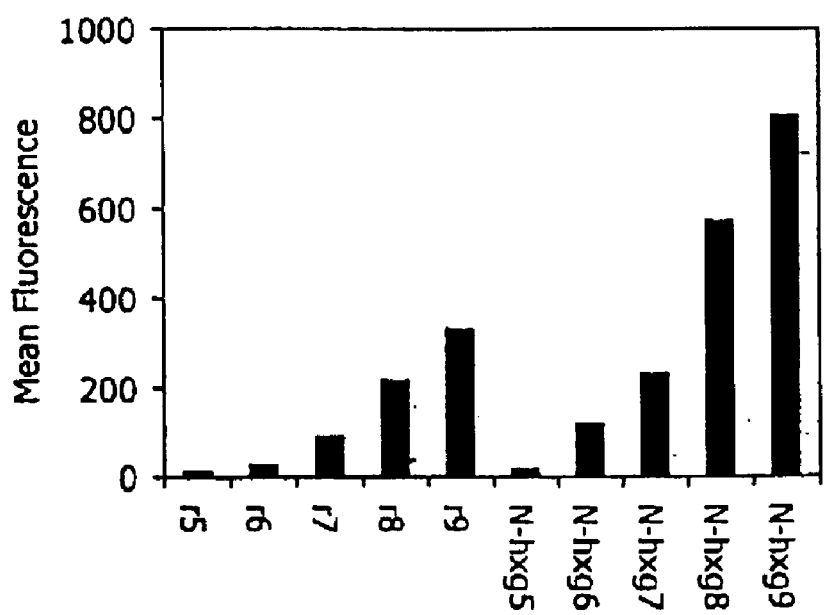
FIG. 28: FACS cellular uptake of and d-arginine oligomers and N-hxg peptoids. Jurkat cells were incubated with varying concentrations (6.3 μM shown) of fluorescently labeled peptoids and peptides for 4 min at 23° C.

After establishing that the N-arg peptoids efficiently crossed cellular membranes, the effect of side chain length (number of methylenes) on cellular uptake was investigated. For a given number of guanidine residues (5,7,9), cellular uptake was proportional to side chain length. Peptoids with longer side chains exhibited more efficient cellular uptake. A nine-mer peptoid analog with a six-methylene spacer between the guanidine head groups and the backbone (N-hxg9) exhibited remarkably higher cellular uptake than the corresponding d-arginine oligomer (r9). The relative order of uptake was N-hxg9 (6 methylene)>N-btg9 (4 methylene)>r9 (3 methylene)>N-arg9 (SEQ ID NO:43) (3 methylene)>N-etg9 (2 methylene) (FIG. 27). Of note, the N-hxg peptoids showed remarkably high cellular uptake, even greater than the corresponding d-arginine oligomers. The cellular uptake of the corresponding heptamers and pentamers also showed the same relative trend. The longer side chains embodied in the N-hxg peptoids improved the cellular uptake to such an extent that the amount of internalization was comparable to the corresponding d-arginine oligomer containing one more guanidine residue (FIG. 28). For example, the N-hxg7 peptoid showed comparable cellular uptake to r8.

Figure 29:
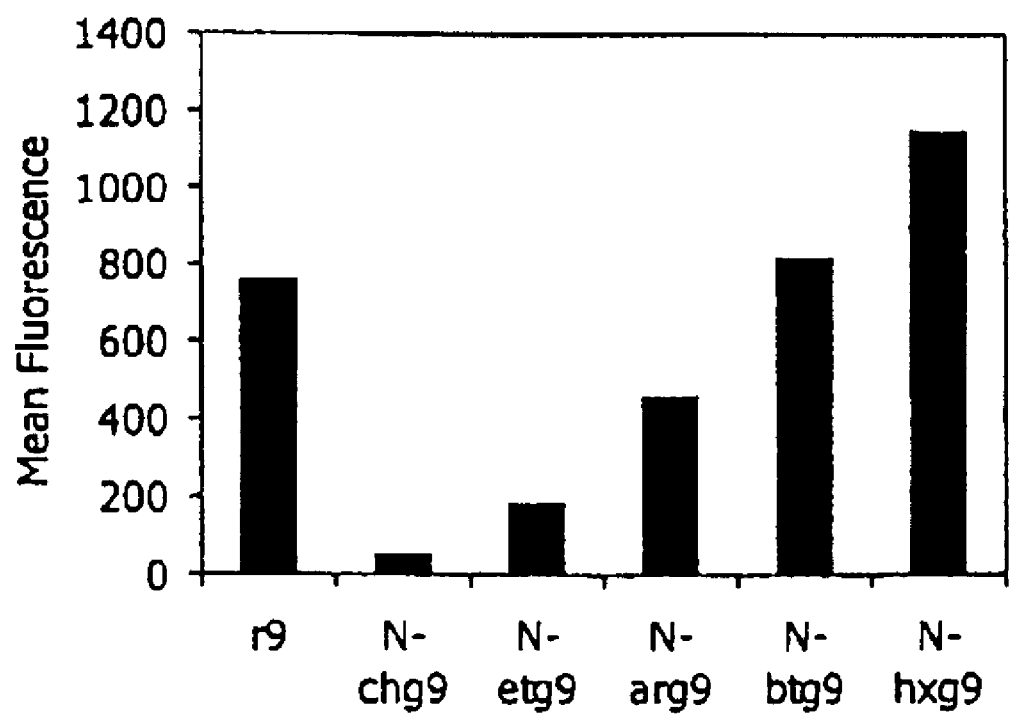
FIG. 29: FACS cellular uptake of d-arginine oligomers and N-chg peptoids. Jurkat cells were incubated with varying concentrations (12.5 μM shown) of fluorescently labeled peptoids and peptides for 4 min at 23° C.

To address whether the increase in cellular uptake was due to the increased length of the sidechains or due to their hydrophobic nature, a set of peptoids was synthesized containing cyclohexyl sidechains. These are referred to as the N-chg5, 7, 9 peptoids. These contain the same number of sidechain carbons as the N-hxg peptoids but possess different degrees of freedom. Interestingly, the N-chg peptoid showed much lower cellular uptake activity than all of the previously assayed peptoids, including the N-etg peptoids (FIG. 29). Therefore, the conformational flexibility and sterically unencumbered nature of the straight chain alkyl spacing groups is important for efficient cellular uptake.

Discussion

The nona-peptide, $Tat_{49-57}$, has been previously shown to efficiently translocate through plasma membranes. The goal of this research was to determine the structural basis for this effect and use this information to develop simpler and more effective molecular transporters. Toward this end, truncated and alanine substituted derivatives of $Tat_{49-57}$ conjugated to a fluorescein label was prepared. These derivatives exhibited greatly diminished cellular uptake compared to $Tat_{49-57}$, indicating that all of the cationic residues of $Tat_{49-57}$, are required for efficient cellular uptake. When compared with our previous studies on short oligomers of cationic oligomers, these findings suggested that an oligomer of arginine might be superior to $Tat_{49-57}$ and certainly more easily and cost effectively prepared. Comparison of short arginine oligomers with $Tat_{49-57}$ showed that members of the former were indeed more efficiently taken into cells. This was further quantified for the first time by Michaelis-Menton kinetics analysis which showed that the R9 (SEQ ID NO:5) and r9 oligomers had $K_m$ values 30-fold and 100-fold greater than that found for $Tat_{49-57}$.

Given the importance of the guanidino head group and the apparent insensitivity of the oligomer chirality revealed in our peptide studies, we designed and synthesized a novel series of polyguanidine peptoids. The peptoids N-arg5,7,9 (SEQ ID NOS:39, 41 and 43), incorporating the arginine side chain, exhibited comparable cellular uptake to the corresponding d-arginine peptides r5,7,9, indicating that the hydrogen bonding along the peptide backbone and backbone chirality are not essential for cellular uptake. This observation is consistent with molecular models of these peptoids, arginine oligomers, and $Tat_{49-57}$, all of which have a deeply embedded backbone and a guanidinium dominated surface. Molecular models further reveal that these structural characteristics are retained in varying degree in oligomers with different alkyl spacers between the peptoid backbone and guanidino head groups. Accordingly, a series of peptoids incorporating 2-(N-etg), 4-(N-btg), and 6-atom (N-hxg) spacers between the backbone and side chain were prepared and compared for cellular uptake with the-N-arg peptoids (3-atom spacers) and d-arginine oligomers. The length of the side chains had a dramatic affect on cellular entry. The amount of cellular uptake was proportional to the length of the side chain with N-hxg>N-btg>N-arg>N-etg. Cellular uptake was improved when the number of alkyl spacer units between the guanidine head group and the backbone was increased. Significantly, N-hxg9 was superior to r9, the latter being 100-fold better than $Tat_{49-57}$. This result led us to prepare peptoid derivatives containing longer octyl spacers (N-ocg) between the guanidino groups and the backbone. Issues related to solubility prevented us from testing these compounds.

Because both perguanidinylated peptides and perguanidinylated peptoids efficiently enter cells, the guanidine head group (independent of backbone) is apparently the critical structural determinant of cellular uptake. However, the presence of several (over six) guanidine moieties on a molecular scaffold is not sufficient for active transport into cells as the N-chg peptoids did not efficiently translocate into cells. Thus, in addition to the importance of the guanidine head group, there are structure/conformational requirements that are significant for cellular uptake.

In summary, this investigation identified a series of structural characteristics including sequence length, amino acid composition, and chirality that influence the ability of $Tat_{49-57}$ to enter cells. These characteristics provided the blueprint for the design of a series of novel peptoids, of which 17 members were synthesized and assayed for cellular uptake. Significantly, the N-hxg9 transporter was found to be superior in cell uptake to r9 which was comparable to N-btg9.

Hence, these peptoid transporters proved to be substantially better than Tat$_{49-57}$. This research established that the peptide backbone and hydrogen bonding along that backbone are not required for cellular uptake, that the guanidino head group is superior to other cationic subunits, and most significantly, that an extension of the alkyl chain between the backbone and the head group provides superior transporters. In addition to better uptake performance, these novel peptoids offer several advantages over Tat$_{49-57}$ including cost-effectiveness, ease of synthesis of analogs, and protease stability. These features along with their significant water solubility (>100 mg/mL) indicate that these novel peptoids could serve as effective transporters for the molecular delivery of drugs, drug candidates, and other agents into cells.

Example 16

Synthesis of Itraconazole-Transporter Conjugate

Figure 30:
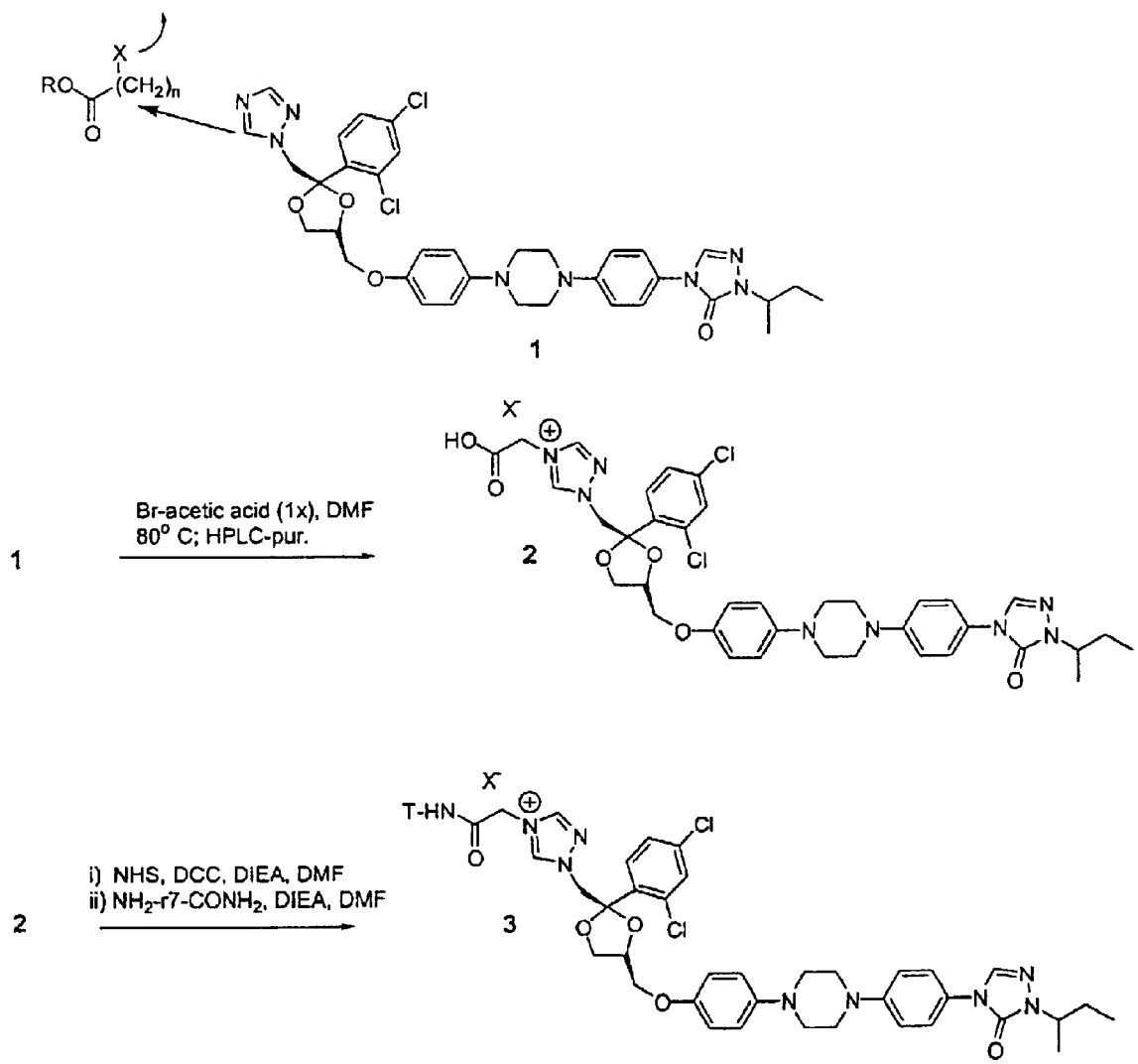
FIG. 30 shows a general strategy for attaching a delivery-enhancing transporter to a drug that includes a triazole ring structure.

This Example provides one application of a general strategy for attaching a delivery-enhancing transporter to a compound that includes a triazole structure. The scheme, using attachment of itraconazole to an arginine (r7) delivery-enhancing transporter as an example, is shown in FIG. 30. In the scheme, R is H or alkyl, n is 1 or 2, and X is a halogen.

The reaction involves making use of quaternization of a nitrogen in the triazole ring to attach an acyl group that has a halogen (e.g., Br, Fl, I) or a methyl ester. Compound 3 was isolated by HPLC. Proton NMR in D$_2$O revealed itraconazole and transporter peaks.

The methyl ester provided yields of 70% and greater, while yields obtained using the Br-propionic acid/ester pair were 40–50%. The acyl derivative is then reacted with the amine of the delivery-enhancing transporter to form the conjugate. Alternatively, the halogenated acyl group can first be attached to the transporter molecule through an amide linkage, after which the reaction with the drug compound is conducted.

Example 17

Preparation of FK506 Conjugates

Figure 31A:
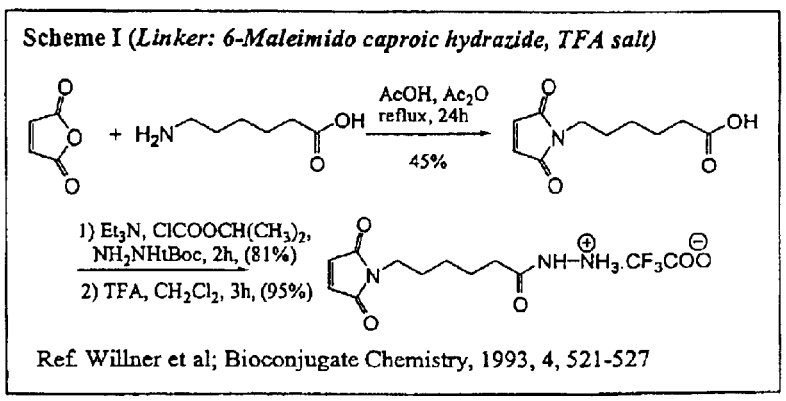
FIG. 31A and FIG. 31B show synthetic schemes for making conjugates in which FK506 is attached to a delivery-enhancing transporter (SEQ ID NOS:44 and 45).
Figure 31A:
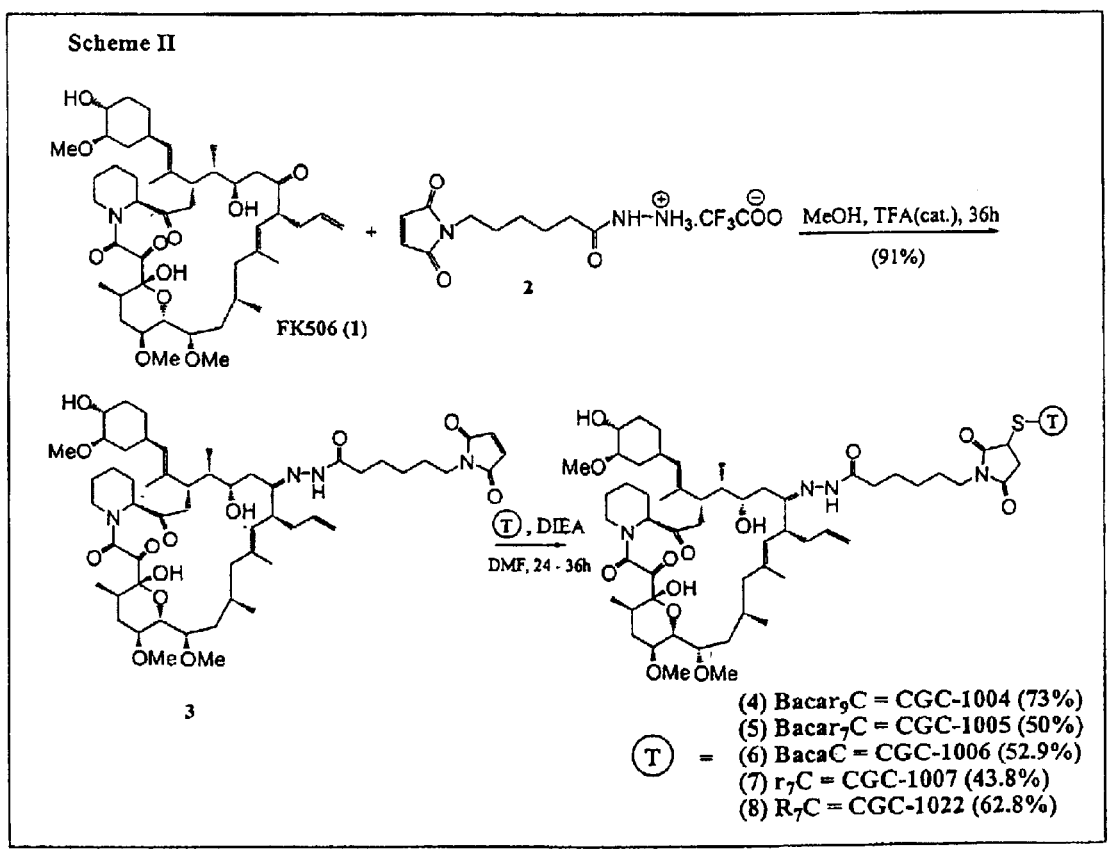
Figure 31B:
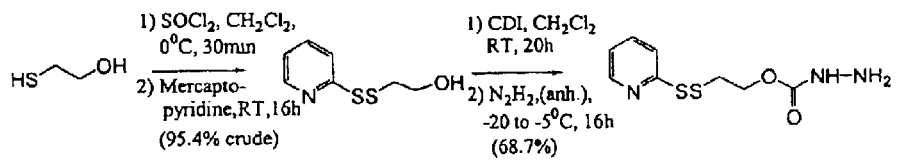
Figure 31B:
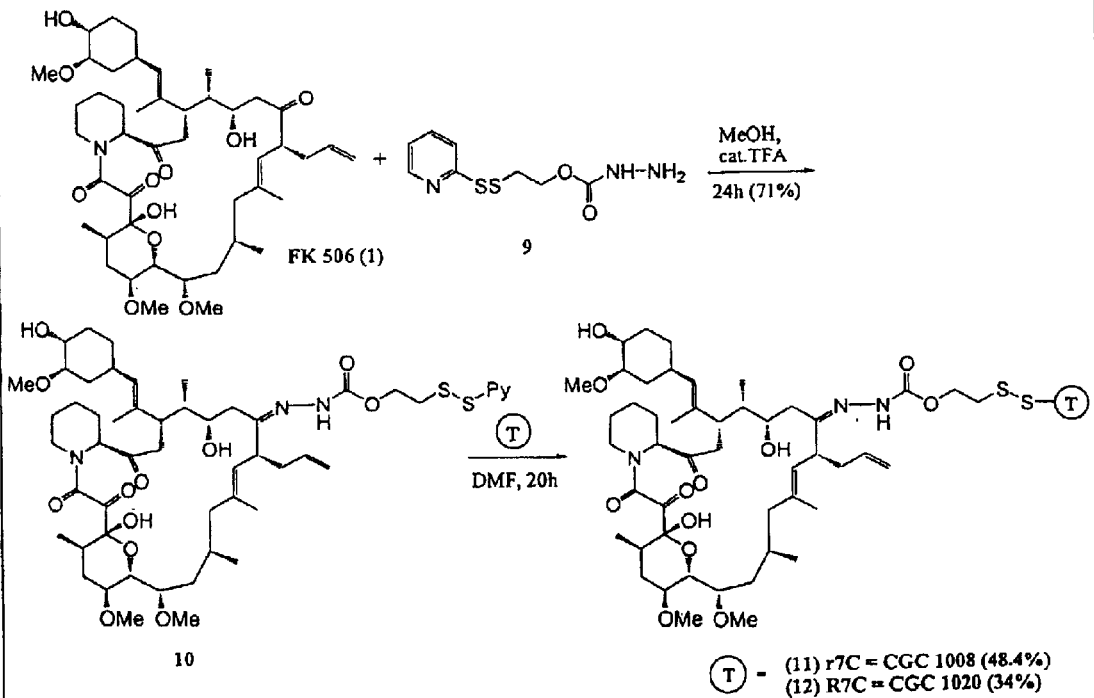

This Example describes the preparation of conjugates in which FK506 is attached to a delivery-enhancing transporter. Two different linkers were used, each of which released FK506 at physiological pH (pH 5.5 to 7.5), but had longer half-lives at more acidic pH. These schemes are diagrammed in FIGS. 31A and B.

Linker 1: 6-maleimidocaproic Hydrazide Trifluroacetate (Scheme I and II)

A solution of FK506 (1) (0.1 g, 124.4 $\mu$mol), 6-maleiimidocaproic hydrazide trifluoroacetate (2) (0.126 g, 373.2 $\mu$mol) and trifluoroacetic acid (catalytic, 1 $\mu$L) in anhydrous methanol (5 mL) was stirred at room temperature for 36 h. The reaction was monitored by thin layer chromatography that showed almost complete disappearance of the starting material. [TLC solvent system—dichloromethane (95): methanol (5), R$_f$=0.3]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (96): methanol (4) as eluent to give the hydrazone 3 (0.116 g, 92%).

A solution of the above hydrazone (3) (0.025 g, 24.7 $\mu$mol), transporter (1×, Bacar$_9$CCONH$_2$.9TFA, Bacar$_7$CCONH$_2$.7TFA, BacaCCONH$_2$, NH$_2$r7CCONH$_2$.8TFA, NH$_2$R7CCONH$_2$.8TFA (SEQ ID NO:32)) and diisopropylethylamine (1×) in anhydrous dimethylformamide (1 mL) were stirred under nitrogen at room temperature for 36 h when TLC indicated the complete disappearance of the starting hydrazone. Solvent was evaporated from the reaction mixture and the residue purified by reverse phase HPLC using trifluoroacetic acid buffered water and acetonitrile.

Yields of conjugates with various transporters:

Conjugate with Bacar$_9$CCONH$_2$.9TFA (4)-73%

Bacar$_7$CCONH$_2$.7TFA (5)-50%

BacaCCONH$_2$ (6)-52.9%

NH$_2$r$_7$CCONH$_2$.8TFA (7)-43.8%

NH$_2$R$_7$CCONH$_2$.8TFA (8)-62.8%

Structures of all the products were confirmed by 1 H-NMR spectra and TOF MS analysis.

Linker 2: 2-(2-pyridinyldithio) Ethyl Hydrazine Carboxylate (Scheme III and IV)

A solution of FK506 (1) (0.1 g, 124.4 $\mu$mol), 2-(2-pyridinyldithio) ethyl hydrazine carboxylate (9) (0.091 g, 373.2 $\mu$mol) and trifluoroacetic acid (catalytic, 1 $\mu$L) in anhydrous methanol (5 mL) was stirred at room temperature for 16 h. The reaction was monitored by thin layer chromatography that showed almost complete disappearance of the starting material. [TLC solvent system—ethyl acetate R$_f$0.5]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (97): methanol (3) as eluent to give the hydrazone 10 (0.091 g, 71%)

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of treating a skin disorder by enhancing delivery of an immunosuppressive conjugate into and across one or more layers of the skin of an animal, the method comprising,
    contacting the skin of the animal with an immunosuppressive conjugate formed from an ascomycin and a delivery-enhancing transporter,
    wherein the delivery-enhancing transporter comprises sufficient guanidino or amidino moieties to increase delivery of the conjugate into and across skin compared to delivery of the ascomycin in the absence of the delivery-enhancing transporter.

2. The method of claim 1, wherein the skin disorder is selected from the group consisting of psoriasis, eczema, atopic dermatitis, contact dermatitis, allergic dermatitis, and alopecia areata.

3. The method of claim 1, wherein the ascomycin is selected from the group consisting of FK506 and rapamycin.

4. The method of claim 1, wherein the delivery-enhancing transporter comprises a non-peptide backbone.

5. The method of claim 1, wherein the delivery-enhancing transporter comprises from 5 to 25 guanidino or amidino moieties.

6. The method of claim 5, wherein the delivery-enhancing transporter comprises between 7 and 15 guanidino moieties.

7. The method of claim 1, wherein the delivery-enhancing transporter comprises at least 6 contiguous guanidino and/or amidino moieties.

8. The method of claim 1, wherein the delivery-enhancing transporter consists essentially of 5 to 50 amino acids, at least 50 percent of which amino acids are arginines or analogs thereof.

9. The method of claim 1, wherein the delivery-enhancing transporter comprises 5 to 25 arginine residues or analogs thereof.

10. The method of claim 9, wherein the delivery-enhancing transporter comprises 8 arginine residues.

11. The method of claim 9, wherein at least one arginine is a D-arginine.

12. The method of claim 11, wherein all of the arginines are D-arginines.

13. The method of claim 8, wherein at least 70 percent of the amino acids that comprise the delivery-enhancing transporter are arginines or arginine analogs.

14. The method of claim 8, wherein the delivery-enhancing transporter comprises at least 5 contiguous arginines or arginine analogs.

15. The method of claim 1, wherein delivery of the compound into and across the skin is at least two-fold greater than that of the compound conjugated to a basic HIV tat peptide consisting of residues 49–57.

16. The method of claim 1, wherein the ascomycin is attached to the delivery enhancing transporter by a linker.

17. A method of treating a fungal infection of the skin by enhancing delivery of an anti-fungal conjugate into and across one or more layers of the skin of an animal, the method comprising,
    contacting the skin of the animal with the conjugate;
    wherein the conjugate comprises an anti-fungal agent and a delivery-enhancing transporter, and
    wherein the delivery-enhancing transporter comprises sufficient guanidino or amidino moieties to increase delivery of the conjugate into and across skin compared to delivery of the anti-fungal agent in the absence of the delivery-enhancing transporter.

18. The method of claim 17, wherein the fungal infection is selected from the group consisting of tinea corporis, tinea pedis, onychomycosis, candidiasis, and tinea versicolor.

19. The method of claim 17, wherein the delivery-enhancing transporter comprises a non-peptide backbone.

20. The method of claim 17, wherein the delivery-enhancing transporter comprises from 5 to 25 guanidino or amidino moieties.

21. The method of claim 20, wherein the delivery-enhancing transporter comprises between 7 and 15 guanidino moieties.

22. The method of claim 17, wherein the delivery-enhancing transporter comprises at least 6 contiguous guanidino and/or amidino moieties.

23. The method of claim 17, wherein the delivery-enhancing transporter consists essentially of 5 to 50 amino acids, at least 50 percent of which amino acids are arginines or analogs thereof.

24. The method of claim 17, wherein the delivery-enhancing transporter comprises 5 to 25 arginine residues or analogs thereof.

25. The method of claim 24, wherein the delivery-enhancing transporter comprises 8 arginine residues.

26. The method of claim 24, wherein at least one arginine is a D-arginine.

27. The method of claim 26, wherein all of the arginines are D-arginines.

28. The method of claim 23, wherein at least 70 percent of the amino acids that comprise the delivery-enhancing transporter are arginines or arginine analogs.

29. The method of claim 17, wherein the delivery-enhancing transporter comprises at least 5 contiguous arginines or arginine analogs.

30. The method of claim 17, wherein delivery of the compound into and across the skin is at least two-fold greater than that of the compound conjugated to a basic HIV tat peptide consisting of residues 49–57.

31. The method of claim 17, wherein the antifungal agent is attached to the delivery enhancing transporter by a linker.

* * * * *

SEQUENCE LISTING

<160> NUMBER OF SEQ ID NOS: 51

<210> SEQ ID NO 1
<211> LENGTH: 5
<212> TYPE: PRT
<213> ORGANISM: Artificial Sequence
<220> FEATURE:

```
<223> OTHER INFORMATION: Description of Artificial Sequence:Arg
      homopolymer R5, Arg oligomer

<400> SEQUENCE: 1

Arg Arg Arg Arg Arg
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Arg
      homopolymer R6, Arg oligomer

<400> SEQUENCE: 2

Arg Arg Arg Arg Arg Arg
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:Arg
      homopolymer R7, heptamer of L-Arg, hepta-L-Arg, Arg oligomer

<400> SEQUENCE: 3

Arg Arg Arg Arg Arg Arg Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:Arg
      homopolymer R8, Arg oligomer

<400> SEQUENCE: 4

Arg Arg Arg Arg Arg Arg Arg Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:Arg
      homopolymer R9, Arg oligomer

<400> SEQUENCE: 5

Arg Arg Arg Arg Arg Arg Arg Arg Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:heptamer of
      L-Arg chemical conjugate after pH dependent
      chemical release
<220> FEATURE:
<221> NAME/KEY: MOD_RES
<222> LOCATION: (1)
<223> OTHER INFORMATION: Xaa =
      2-[4-benzyl-2,5-diketopiperazinyl]-acetyl-Arg
```

```
<400> SEQUENCE: 6

Xaa Arg Arg Arg Arg Arg
 1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:unlabeled
      peptide
<220> FEATURE:
<221> NAME/KEY: MOD_RES
<222> LOCATION: (10)
<223> OTHER INFORMATION: Xaa = cysteinamine

<400> SEQUENCE: 7

Arg Arg Arg Arg Arg Arg Arg Gly Gly Xaa
 1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:analog of
      HIV-1 tat protein basic region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 8

Xaa Arg Lys Lys Arg Arg Gln Arg Arg Arg
 1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:Tat-49-56
      truncated analog of HIV-1 tat protein basic region
      Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 9

Xaa Arg Lys Lys Arg Arg Gln Arg Arg
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:Tat-49-55
      truncated analog of HIV-1 tat protein basic region
      Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 10
```

```
Xaa Arg Lys Lys Arg Arg Gln Arg
  1               5
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:Tat-50-57
      truncated analog of HIV-1 tat protein basic region
      Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 11

```
Xaa Lys Lys Arg Arg Gln Arg Arg Arg
  1               5
```

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:Tat-51-57
      truncated analog of HIV-1 tat protein basic region
      Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 12

```
Xaa Lys Arg Arg Gln Arg Arg Arg
  1               5
```

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:A-49
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 13

```
Xaa Ala Lys Lys Arg Arg Gln Arg Arg Arg
  1               5                  10
```

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:A-50
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 14

```
Xaa Arg Ala Lys Arg Arg Gln Arg Arg Arg
 1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:A-51
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 15

Xaa Arg Lys Ala Arg Arg Gln Arg Arg Arg
 1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:A-52
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 16

Xaa Arg Lys Lys Ala Arg Gln Arg Arg Arg
 1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:A-53
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 17

Xaa Arg Lys Lys Arg Ala Gln Arg Arg Arg
 1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:A-54
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)
```

-continued

```
<400> SEQUENCE: 18

Xaa Arg Lys Lys Arg Arg Ala Arg Arg Arg
 1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:A-55
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 19

Xaa Arg Lys Lys Arg Arg Gln Ala Arg Arg
 1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:A-56
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 20

Xaa Arg Lys Lys Arg Arg Gln Arg Ala Arg
 1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:A-57
      Ala-substituted analog of HIV-1 tat protein basic
      region Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 21

Xaa Arg Lys Lys Arg Arg Gln Arg Arg Ala
 1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:Tat-57-49
      retro-isomer of HIV-1 tat protein basic region
      Tat-49-57
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)
```

```
<400> SEQUENCE: 22

Xaa Arg Arg Arg Gln Arg Arg Lys Lys Arg
 1               5                   10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Arg oligomer
      R5, Arg homopolymer
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 23

Xaa Arg Arg Arg Arg Arg
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:Arg oligomer
      R6, Arg homopolymer
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 24

Xaa Arg Arg Arg Arg Arg Arg
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:Arg oligomer
      R7, Arg homopolymer
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 25

Xaa Arg Arg Arg Arg Arg Arg Arg
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:Arg oligomer
      R8, Arg homopolymer
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 26
```

-continued

```
Xaa Arg Arg Arg Arg Arg Arg Arg Arg
  1               5
```

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence:Arg oligomer
      R9, Arg homopolymer
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 27

```
Xaa Arg Arg Arg Arg Arg Arg Arg Arg Arg
  1               5                  10
```

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:HIV-1 tat
      protein basic region Tat-49-57

<400> SEQUENCE: 28

```
Arg Lys Lys Arg Arg Gln Arg Arg Arg
  1               5
```

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:Antennapedia
      homeodomain, Antennapedia-43-58

<400> SEQUENCE: 29

```
Arg Gln Ile Lys Ile Trp Phe Gln Asn Arg Arg Met Lys Trp Lys Lys
  1               5                  10                  15
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence:Antennapedia
      homeodomain, Antennapedia-43-58
<220> FEATURE:
<221> NAME/KEY: MOD_RES
<222> LOCATION: (1)
<223> OTHER INFORMATION: Xaa = fluorescein linked to amino group of
      aminohexanoic acid (Fl-ahx)

<400> SEQUENCE: 30

```
Xaa Arg Gln Ile Lys Ile Trp Phe Gln Asn Arg Arg Met Lys Trp Lys
  1               5                  10                  15

Lys
```

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety DTPA-aca-R7-CO2H

```
<220> FEATURE:
<221> NAME/KEY: MOD_RES
<222> LOCATION: (1)
<223> OTHER INFORMATION: amino acaproic acid (aca) linked to
      diethylenetriaminepentaacetic acid (DTPA)

<400> SEQUENCE: 31

Xaa Arg Arg Arg Arg Arg Arg Arg
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety NH-2-R-7CCONH-2.8TFA
<220> FEATURE:
<221> NAME/KEY: MOD_RES
<222> LOCATION: (8)
<223> OTHER INFORMATION: Xaa = cysteinaminde

<400> SEQUENCE: 32

Arg Arg Arg Arg Arg Arg Arg Xaa
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = copper-diethylenetriaminepentaacetic acid
      complex (Cu-DTPA) linked to aminocaproic acid
      (aca)
<220> FEATURE:
<221> NAME/KEY: MOD_RES
<222> LOCATION: (8)
<223> OTHER INFORMATION: Xaa = Arg bound to peptide synthesizer solid-
      phase resin

<400> SEQUENCE: 33

Xaa Arg Arg Arg Arg Arg Arg Xaa
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = diethylenetriaminepentaacetic acid
      (DTPA) linked to aminocaproic acid (aca)

<400> SEQUENCE: 34

Xaa Arg Arg Arg Arg Arg Arg Arg
  1               5

<210> SEQ ID NO 35
<211> LENGTH: 8
<212> TYPE: PRT
<213> ORGANISM: Artificial Sequence
<220> FEATURE:
```

```
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = copper-diethylenetriaminepentaacetic
      acid complex (Cu-DTPA) linked to aminocaproic acid
      (aca)

<400> SEQUENCE: 35

Xaa Arg Arg Arg Arg Arg Arg Arg
 1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = biotinylated aminocaproic acid (aca)
<220> FEATURE:
<221> NAME/KEY: MOD_RES
<222> LOCATION: (11)
<223> OTHER INFORMATION: Xaa = cysteinamide conjugated to hydrocortisone

<400> SEQUENCE: 36

Xaa Arg Arg Arg Arg Arg Arg Arg Ala Ala Xaa
 1               5                  10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = Arg conjugated to benzyl (Bz) and acetyl
      (Ac) protected C-2' derivative of taxol through
      benzyl-(para-hydroxy benzoate) carbonate

<400> SEQUENCE: 37

Xaa Arg Arg Arg Arg Arg Arg
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = Arg conjugated to benzyl (Bz) and acetyl
      (Ac) protected C-2' derivative of taxol through
      benzyl-(para-hydroxy benzoate) carbamate

<400> SEQUENCE: 38

Xaa Arg Arg Arg Arg Arg Arg
 1               5

<210> SEQ ID NO 39
<211> LENGTH: 6
```

```
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (6)
<223> OTHER INFORMATION: Xaa = argininamide

<400> SEQUENCE: 39

Xaa Arg Arg Arg Arg Xaa
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (7)
<223> OTHER INFORMATION: Xaa = argininamide

<400> SEQUENCE: 40

Xaa Arg Arg Arg Arg Arg Xaa
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (8)
<223> OTHER INFORMATION: Xaa = argininamide

<400> SEQUENCE: 41

Xaa Arg Arg Arg Arg Arg Arg Xaa
 1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = fluorescein isothiocyanate (FITC) labeled
      aminocaproic acid (aca)
```

```
<220> FEATURE:
<221> NAME/KEY: MOD_RES
<222> LOCATION: (9)
<223> OTHER INFORMATION: Xaa = argininamide

<400> SEQUENCE: 42

Xaa Arg Arg Arg Arg Arg Arg Arg Xaa
 1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = fluorescein isothiocyanate (FITC) labeled
      aminocaproic acid (aca)
<220> FEATURE:
<221> NAME/KEY: MOD_RES
<222> LOCATION: (10)
<223> OTHER INFORMATION: Xaa = argininamide

<400> SEQUENCE: 43

Xaa Arg Arg Arg Arg Arg Arg Arg Arg Xaa
 1               5                  10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (8)
<223> OTHER INFORMATION: Xaa = 6-maleimidocaproic hydrazone derivative
      of FK506 conjugated to Cys

<400> SEQUENCE: 44

Arg Arg Arg Arg Arg Arg Arg Xaa
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (8)
<223> OTHER INFORMATION: Xaa = dithioethyl hydrazone derivative of FK506
      conjugated to Cys

<400> SEQUENCE: 45

Arg Arg Arg Arg Arg Arg Arg Xaa
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:delivery
      enhancing transporter moiety conjugate
```

```
-continued

<220> FEATURE:
<221> NAME/KEY: MOD_RES
<222> LOCATION: (1)
<223> OTHER INFORMATION: Xaa = biotinylated aminocaproic acid (aca)
<220> FEATURE:
<221> NAME/KEY: MOD_RES
<222> LOCATION: (7)
<223> OTHER INFORMATION: Xaa = cysteinamide

<400> SEQUENCE: 46

Xaa Arg Arg Arg Arg Arg Xaa
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = biotinylated aminocaproic acid (aca)
<220> FEATURE:
<221> NAME/KEY: MOD_RES
<222> LOCATION: (9)
<223> OTHER INFORMATION: Xaa = cysteinamide

<400> SEQUENCE: 47

Xaa Arg Arg Arg Arg Arg Arg Arg Xaa
 1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence:delivery
      enhancing transporter moiety conjugate
<220> FEATURE:
<221> NAME/KEY: MOD_RES
<222> LOCATION: (1)
<223> OTHER INFORMATION: Xaa = biotinylated aminocaproic acid (aca)
<220> FEATURE:
<221> NAME/KEY: MOD_RES
<222> LOCATION: (11)
<223> OTHER INFORMATION: Xaa = cysteinamide

<400> SEQUENCE: 48

Xaa Arg Arg Arg Arg Arg Arg Arg Arg Arg Xaa
 1               5                  10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence:delivery-
      enhancing transporter of 7-15 arginine residues
<220> FEATURE:
<221> NAME/KEY: MOD_RES
<222> LOCATION: (8)..(15)
<223> OTHER INFORMATION: Arg at positions 8-15 may be present or absent

<400> SEQUENCE: 49

Arg Arg Arg Arg Arg Arg Arg Arg Arg Arg Arg Arg Arg Arg Arg
 1               5                  10                  15

<210> SEQ ID NO 50
<211> LENGTH: 25
```

-continued

```
<212> TYPE: PRT
<213> ORGANISM: Artificial Sequence
<220> FEATURE:
<223> OTHER INFORMATION: Description of Artificial Sequence:delivery-
      enhancing transporter polymer of poly-arginine molecules between
      6 and 25 residues in length
<220> FEATURE:
<221> NAME/KEY: MOD_RES
<222> LOCATION: (7)..(25)
<223> OTHER INFORMATION: Arg at positions 7-25 may be present or absent

<400> SEQUENCE: 50

Arg Arg Arg Arg Arg Arg Arg Arg Arg Arg Arg Arg Arg Arg Arg Arg
 1               5                   10                  15

Arg Arg Arg Arg Arg Arg Arg Arg Arg
            20                  25

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence:delivery-
      enhancing transporter of 5-25 arginine residues
<220> FEATURE:
<221> NAME/KEY: MOD_RES
<222> LOCATION: (6)..(25)
<223> OTHER INFORMATION: Arg at positions 6-25 may be present or absent

<400> SEQUENCE: 51

Arg Arg Arg Arg Arg Arg Arg Arg Arg Arg Arg Arg Arg Arg Arg Arg
 1               5                   10                  15

Arg Arg Arg Arg Arg Arg Arg Arg Arg
            20                  25
```